(12) United States Patent
Akinc et al.

(10) Patent No.: US 11,091,759 B2
(45) Date of Patent: Aug. 17, 2021

(54) METHODS AND COMPOSITIONS FOR TREATING A SERPINC1-ASSOCIATED DISORDER

(71) Applicant: Genzyme Corporation, Cambridge, MA (US)

(72) Inventors: Akin Akinc, Needham, MA (US); Benny Sorensen, Walpole, MA (US); Pushkal Garg, Newton, MA (US); Gabriel Robbie, Brookline, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 15/371,300

(22) Filed: Dec. 7, 2016

(65) Prior Publication Data

US 2017/0159053 A1    Jun. 8, 2017

Related U.S. Application Data

(60) Provisional application No. 62/429,241, filed on Dec. 2, 2016, provisional application No. 62/366,304, filed on Jul. 25, 2016, provisional application No. 62/315,228, filed on Mar. 30, 2016, provisional application No. 62/264,013, filed on Dec. 7, 2015.

(51) Int. Cl.
| | | |
|---|---|---|
| *C12N 15/11* | (2006.01) | |
| *C12N 15/113* | (2010.01) | |
| *A61K 31/713* | (2006.01) | |
| *A61K 47/54* | (2017.01) | |

(52) U.S. Cl.
CPC .......... *C12N 15/113* (2013.01); *A61K 31/713* (2013.01); *A61K 47/549* (2017.08); *C12N 2310/14* (2013.01); *C12N 2310/315* (2013.01); *C12N 2310/321* (2013.01); *C12N 2310/346* (2013.01); *C12N 2310/351* (2013.01); *C12N 2320/35* (2013.01)

(58) Field of Classification Search
CPC .................................................. C12N 15/113
See application file for complete search history.

(56) References Cited

U.S. PATENT DOCUMENTS

| | | |
|---|---|---|
| 4,517,294 A | 5/1985 | Bock et al. |
| 6,794,493 B2 | 9/2004 | Walston et al. |
| 8,071,291 B2 | 12/2011 | Bare et al. |
| 8,106,022 B2 | 1/2012 | Manoharan et al. |
| 8,741,844 B2 | 6/2014 | Borgel born Botbol et al. |
| 9,127,274 B2 | 9/2015 | Akinc et al. |
| 9,376,680 B2 | 6/2016 | Akinc et al. |
| 2005/0080032 A1 | 4/2005 | Gross et al. |
| 2007/0031844 A1 | 2/2007 | Khvorova et al. |
| 2008/0113351 A1 | 5/2008 | Naito et al. |
| 2008/0152661 A1 | 6/2008 | Rozema et al. |
| 2009/0239814 A1 | 9/2009 | Manoharan et al. |
| 2010/0112687 A1 | 5/2010 | Quay et al. |
| 2010/0267090 A1 | 10/2010 | Sato |
| 2011/0269823 A1 | 11/2011 | Nakayama et al. |
| 2013/0317081 A1 | 11/2013 | Akinc et al. |
| 2014/0350071 A1 | 11/2014 | Sehgal et al. |
| 2014/0356377 A1 | 12/2014 | Hack et al. |
| 2016/0017330 A1 | 1/2016 | Akinc et al. |
| 2016/0257954 A1 | 9/2016 | Akinc et al. |
| 2017/0159053 A1 | 6/2017 | Akinc et al. |

FOREIGN PATENT DOCUMENTS

| | | |
|---|---|---|
| WO | WO-2004/045543 A2 | 6/2004 |
| WO | WO-2006/006948 A2 | 1/2006 |
| WO | WO-2009/073809 A2 | 6/2009 |
| WO | 2009134487 A2 | 11/2009 |
| WO | WO-2010/081878 A1 | 7/2010 |
| WO | WO-2010/120526 A2 | 10/2010 |
| WO | 2010130825 A2 | 11/2010 |
| WO | WO-2010/144740 A1 | 12/2010 |
| WO | 2011104169 A1 | 9/2011 |
| WO | 2012/177784 A2 | 12/2012 |
| WO | WO-2013/159108 A2 | 10/2013 |
| WO | WO-2013/163430 A2 | 10/2013 |
| WO | WO-2015/175510 A1 | 11/2015 |
| WO | WO-2016/183009 A2 | 11/2016 |
| WO | WO-2017/100236 A1 | 6/2017 |

OTHER PUBLICATIONS

Fryar CD, Gu Q, Ogden CL, Flegal KM. Anthropometric reference data for children and adults: United States, 2011-2014. National Center for Health Statistics. Vital Health Stat 3(39). 2016. (Year: 2016).*
Scmidt, R. Eur J Clin Pharmacol (1988) 34: 15. https://doi.org/10.1007/BF01061410 (Year: 1988).*
Hong DS, Kurzrock R, Oh Y, et al. A phase 1 dose escalation, pharmacokinetic, and pharmacodynamic evaluation of eIF-4E antisense oligonucleotide LY2275796 in patients with advanced cancer. Clin Cancer Res. 2011;17(20):6582-6591. doi:10.1158/1078-0432.CCR-11-0430 (Year: 2011).*
Majlessi et al.,"Advantages of 2'-O-methyl oligoribonucleotide probes for detecting RNA targets.", Nucleic Acids Research, 1998, vol. 26, No. 9, pp. 2224-2229.
Akin Akinc: "ALN-AT3: An Invetigated RNAi Therapeutic Targeting Antithrombin for the treatment of Hemophilia", (May 15, 2014) URL:http://www.alnylam.com/web/assets/ALNY-HemophiliaProgram-WFH-May2014.pdf.
Safdar et al. "Acute and severe coagulopathy in adult mice following silencing of hepatic antithrombin and protein C production", Blood, May 23, 2013, vol. 121 No. 21 pp. 4413-4416.

(Continued)

*Primary Examiner* — Ekaterina Poliakova-Georgantas
(74) *Attorney, Agent, or Firm* — Steptoe & Johnson LLP; Z. Ying Li; David Caianiello

(57) ABSTRACT

The invention relates to iRNA, e.g., double stranded ribonucleic acid (dsRNA), compositions targeting the Serpinc1 gene, and methods of using such iRNA, e.g., dsRNA, compositions to inhibit expression of Serpinc1 and to treat subjects having a Serpinc1-associated disease, e.g., a bleeding disorder, such as a hemophilia.

38 Claims, 27 Drawing Sheets

Specification includes a Sequence Listing.

(56) References Cited

OTHER PUBLICATIONS

Akin Akinc, "An RNAi Theraoeutic Targeting Antithrombia Increases thrombin Generation and Imoprves Hemostasis" XXIV Congress of the ISTH, Jul. 2, 2013.
International Search Report & Written Opinion issued in PCT/US13/38218, dated Dec. 2, 2013.
Invitation to Pay Additional Fees, issued in PCT/US13/38218, dated Sep. 5, 2013.
International Preliminary Report on Patentability issued in PCT/US2015/030337, dated Nov. 15, 2016.
International Preliminary Report on Patentability issued in PCT/US2015/057717 dated May 2, 2017.
International Search Reporting and Written Opinion issued in PCT/US2016/065245 dated Mar. 20, 2017.
Bolliger, et al. "Heterozygous antithrombin deficiency improves in vivo haemostasis in factor VIII-deficient mice." Thromb Haemost. Jun. 2010;103(6):1233-8.
Di Micco et al. "Inhibition of antithrombin by protein SV-IV normalizes the coagulation of hemophilic blood," European Journal of Pharmacology 391 2000. 1-9.
Shetty et al., "Contribution of natural anticoagulant and fibrinolytic factors in modulating the clinical severity of haemophilia patients", British Journal of Haematology (2007) 138:541-4.
U.S. Appl. No. 13/837,129 U.S. Pat. No. 9,127,274, filed Mar. 15, 2013 Sep. 8, 2015, US 20130317081, Granted.
U.S. Appl. No. 14/806,084 U.S. Pat. No. 9,376,680, filed Jul. 22, 2015 Jun. 28, 2016, US 20160017330, Granted.
U.S. Appl. No. 15/070,358, filed Mar. 15, 2016, US 20160257954, Abandoned.
U.S. Appl. No. 15/955,873, filed Apr. 18, 2018, Pending.
PCT/US2015/030337, May 12, 2015, WO 2015/175510, Abandoned.
PCT/US2015/057717, Oct. 28, 2015, WO 2016/069694, Completed.
PCT/US2018/041400, Jul. 10, 2018, Pending.
GenBank JA674123.1 "Sequence 513 from Patent WO2011144718," of Dec. 11, 2011.
Pon et al., "Tandem oligonucleotide synthesis using linker phosphoramidites," Nucleic Acids Res. (2005) 33 (6):1940-48.
Roberts et al., "REBASE-enzymes and genes for DNA restriction and modification," Nucleic Acids Res. (2007) 35 (Database issue); D269-270.
Shetty et al., "Contribution of natural anticoagulant and fibrinolytic factors in modulating the clinical severity of haemophilia patients," Br J of Haem. (2007)138:541-44.
Waters et al., "Aptamer ARC19499 mediates a procoagulant hemostatic effect by inhibiting tissue factor pathway inhibitor," Blood (2011) 117(20): 5514-22.
Parunov et al., "Improvement of Spatial Fibrin Formation by the Anti-TFPI Aptamer BAX499: Changing Clot Size by Targeting Extrinsic Pathway Initiation," J of Throm and Haem. (2011) 9:1825-34.
Prochownik et al., "Isolation of a cDNA Clone for Human Antithrombin III," J of Biol Chem. (1983) 258(13):8389-94.
"Blood coagulation and its regulation pathway," J of Mie Pref Coll of Nurs. (2008) 12:1-6.
Journal of Japan Surgical Society (2003) 104(12):840-46.
Akinc, "ALN-AT3: An Investigational RNAi Therapeutic Targeting Antithrombin for the Treatment of Hemophilia," WHF 2014 World Congress, May 15, 2014.
Pasi et al., "A Subcutaneously Administered Investigational RNAi Therapeutic (Fitusiran, ALN-AT3) Targeting Antithrombin for Treatment of Hemophilia: Interim Weekly and Monthly Dosing Results in Patients with Hemophilia A or B," Blood (2015) 126(23):551.
Kenet et al., "Antithrombin Reduction Corrected Thrombin Generation in Samples from Hemophilia A and B Patients with Inhibitors," Blood (2015) 126(23):552.
Barros et al., "Safety Evaluation of Chronic Antithrombin Silencing in Non-Human Primate and Expanded Therapeutic Index in a Hemophilia a Mouse Model," Int J of Toxic. (2016) (35):1:79.
Sorensen et al., "A Subcutaneously Administered RNAi Therapeutic (ALN-AT3) Targeting Antithrombin for Treatment of Hemophilia: Interim Phase 1 Study Results in Healthy Volunteers and Patients with Hemophilia A or B," Blood (2014) 124(21):693.
Pasi et al., "Targeting of Antithrombin in Hemophilia A or B with RNAi Therapy," The New England Journal of Medicine (2017) 377(9):819-28.
Pasi et al., "Fitusiran, an Investigational RNAi Therapeutic Targeting Antithrombin for the Treatment of Hemophilia: Updated Results from a Phase 1 and Phase 1/2 Extension Study in Patients with Inhibitors," Blood Jan. 1, 2016 128(22):1397.
Barros et al., "Expanded Therapeutic Index of Antithrombin Silencing and Correction of Aptt in a Hemophilia A Mouse Model," Blood (2013) 122(21):3585.
Sehgal et al., "An RNAi Therapeutic Targeting Antithrombin to Rbalance the Coagulation System and Promote Hemostasis in Hemophilia," Nat Med. (2015) 21(5):492-97.
Akinc et al., "An RNAi Therapeutic Targeting Antithrombin Increases Thrombin Generation in Nonhuman Primates," 54th Annual Meeting and Exposition of the American-Society-of-Hematology (ASH), Dec. 7, 2012 (Dec. 7, 2012).
Alnylam Pharmaceuticals 2017 Press Release, "Alnylam Provides Pipeline Update on Fitusiran and Givosiran Investigational RNAi Therapeutic Programs," [retrieved on Jul. 30, 2020].
Sanofi 2020 Press Release, "Sanofi announces positive long-term efficacy and safety data for fitusiran from interim analysis of Phase 2 extension study in people with hemophilia A and B, with or without inhibitors," [retrieved on Jul. 30, 2020].
Ragni et al., "Fitusiran, an Investigational RNAi Therapeutic Targeting Antithrombin for the Treatment of Hemophilia: Updated Results from a Phase 1 and Phase 1 and 2 Extension Study in Patients without Inhibitors," Blood (2016) 128(22):2572.
Ragni et al., "Fitusiran, an Investigational RNAi Therapeutic Targeting Antithrombin for the Treatment of Hemophilia: Results from Phase 1 and Phase 2 Extension Studies in Patients without Inhibitors," Dec. 4, 2016.
Sanofi, Feb. 5, 2021 Press Release, "Sanofi presents amended protocols in fitusiran clinical studies at EAHAD 2021.".
Negrier et al., "Fitusiran, an siRNA Therapeutic Targeting Antithrombin for the Treatment of Haemophilia: Proposed Revisions to Dose and Regimen as a Risk Mitigation for Vascular Thrombosis," Feb. 5, 2021.
Sanofi, Dec. 10, 2020 Press Release, "Sanofi to resume dosing in fitusiran clinical studies in the U.S.".
Pipe et al., "Presentation of the Long-term Durability, Safety and Efficacy of Fitusiran Prophylaxis in People with Hemophilia A or B, with or without inhibitors—Results from the Phase 2 Study," Dec. 7, 2020.
Pasi et al., "A Subcutaneously Administered Investigational RNAi Therapeutic (Fitusiran) Targeting Antithrombin for Treatment of Hemophilia: Interim Weekly and Monthly Dosing Results in Patients with Hemophilia A or B," World Federation of Hemophilia (WFH) 2016 World Congress; Orlando, FL, USA; Jul. 25, 2016.
Pasi et al., "Fitusiran, an Investigational RNAi Therapeutic Targeting Antithrombin for the Treatment of Hemophilia Updated Results from Phase 1 and Phase 2 Extension Studies in Patients with Inhibitors," 60th American Society of Hemophilia Meeting and Exposition; San Diego, CA, USA; Dec. 3, 2016.
Pasi et al., "Fitusiran, an Investigational RNAi Therapeutic Targeting Antithrombin for the Treatment of Hemophilia nterim Results from a Phase 2 Extension Study in Patients with Hemophilia A or B with and Without Inhibitors," International Society on Thrombosis and Haemostasis (ISTH) 2017 Congress; Berlin, Germany; Jul. 10, 2017.

\* cited by examiner

ABR, annualized bleeding rate; SEM, standard error of the mean
†Number of patients with time spent in quartile; ‡For each patient, the ABR in each quartile is calculated by 365.24*(number of bleed events/number of days in quartile)
**P-value < 0.05

| Dose | Patient | Period† | Pre-study‡ ABR | Onset ABR | Observation period | | | |
|---|---|---|---|---|---|---|---|---|
| | | | | | All Bleeds, n | ABR | Spontaneous bleeds, n | AsBR |
| 225 mcg/kg | C1-1 | PPx | 2 | 13 | 1 | 4 | 1 | 4 |
| | C1-2 | PPx | 0 | 0 | 1 | 4 | 0 | 0 |
| | C1-3 | PPx | 0 | 50 | 4 | 17 | 0 | 0 |
| 450 mcg/kg | C2-1 | PPx | 4 | 25 | 4 | 17 | 3 | 13 |
| | C2-2 | OD | 38 | 13 | 0 | 0 | 0 | 0 |
| | C2-3 | PPx | 4 | 0 | 1 | 4 | 0 | 0 |
| 900 mcg/kg | C3-1 | PPx | 0 | 0 | 0 | 0 | 0 | 0 |
| | C3-2 | OD | 20 | 25 | 3 | 13 | 0 | 0 |
| | C3-3 | OD | 32 | 25 | 0 | 0 | 0 | 0 |
| 1800 mcg/kg | C4-1 | PPx | 0 | 25 | 0 | 0 | 0 | 0 |
| | C4-2 | OD | 24 | 0 | 0 | 0 | 0 | 0 |
| | C4-3 | PPx | 0 | 25 | 0 | 0 | 0 | 0 |
| 80 mg** | C5-1 | PPx | 12 | 13 | 2 | 9 | 1 | 4 |
| | C5-2 | PPx | 16 | 0 | 0 | 0 | 0 | 0 |
| | C5-3 | PPx | 6 | 13 | 2 | 9 | 0 | 0 |
| | C5-5 | PPx | 6 | 13 | 0 | 0 | 0 | 0 |
| | C5-6 | PPx | 0 | 13 | 0 | 0 | 0 | 0 |

PPx: Prophylaxis, OD: On-Demand; ABR, annualized bleeding rate; AsBR, annualized spontaneous bleeding rate
†Post hoc analysis of treated bleed events during Onset (Day 0-28) and Observation periods (Day 29 to last study visit or last dose+56 days, whichever is earlier ‡ Pre-study ABR derived from medical records.
**Patient C5-4 withdrawn, excluded from analysis

Figure 12

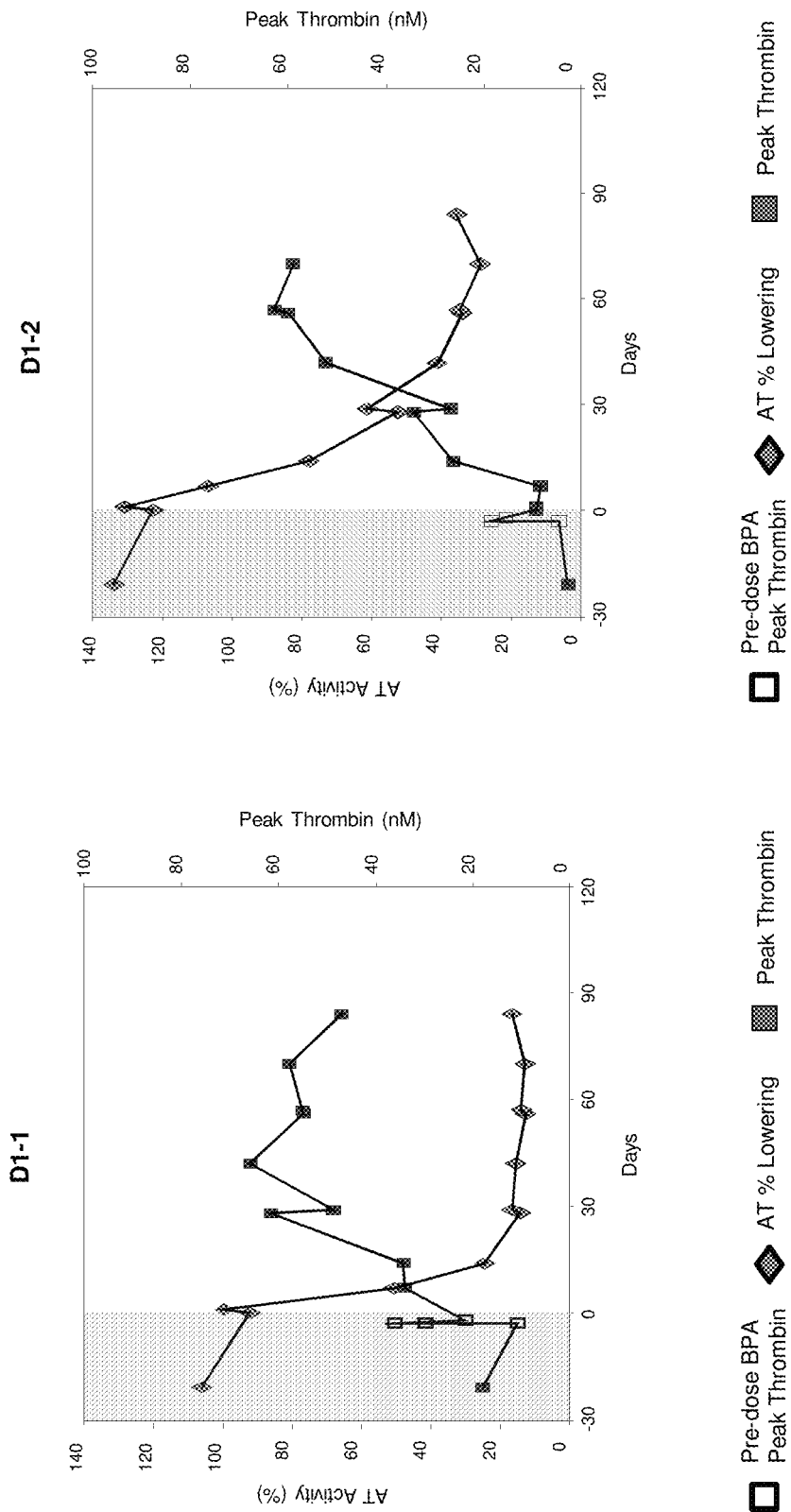

| Patient | Dose | Pre-study ABR‡ | Onset ABR | Observation Period ||||
|---|---|---|---|---|---|---|---|
| | | | | Days in Obs Period | All Bleeds, n | ABR | Spontaneous Bleeds, n | AsBR |

| Patient | Dose | Pre-study ABR‡ | Onset ABR | Days in Obs Period | All Bleeds, n | ABR | Spontaneous Bleeds, n | AsBR |
|---|---|---|---|---|---|---|---|---|
| D1-1^ | 50 mg | 40 | 13 | 191 | 3 | 5.7 | 2 | 3.8 |
| D1-2^ | 50 mg | 26 | 13 | 180 | 5 | 10.1 | 3 | 6.1 |
| D1-3 | 50 mg | 0 | 0 | 84 | 0 | 0 | 0 | 0 |
| D1-4^ | 50 mg | 52 | 38 | 162 | 11 | 25 | 9 | 20 |
| D1-5^ | 50 mg | 80 | 38 | 160 | 20 | 46 | 12 | 27 |
| D1-6^ | 50 mg | 16 | 13 | 156 | 0 | 0 | 0 | 0 |
| D2-1 | 80 mg | 48 | 0 | 48 | 1 | 7.6 | 0 | 0 |
| D2-2 | 80 mg | 48 | 0 | 41 | 0 | 0 | 0 | 0 |
| D2-3 | 80 mg | 8 | 0 | 72 | 0 | 0 | 0 | 0 |
| D2-4^ | 80 mg | 48 | 13 | 56 | 0 | 0 | 0 | 0 |
| D2-5 | 80 mg | 36 | 0 | 69 | 0 | 0 | 0 | 0 |
| D2-6 | 80 mg | 20 | 0 | 69 | 1 | 5.3 | 0 | 0 |
| D2-7^ | 80 mg | 14 | 0 | 55 | 0 | 0 | 0 | 0 |
| D2-8 | 80 mg | 20 | 13 | 55 | 2 | 13.3 | 2 | 13.3 |
| D2-9 | 80 mg | 12 | 0 | 13 | 0 | 0 | 0 | 0 |
| D2-10 | 80 mg | 44 | 0 | 13 | 0 | 0 | 0 | 0 |

OLE, open-label extension; ABR, annualized bleeding rate; AsBR, annualized spontaneous bleed rate
†Post hoc analysis of treated bleed events during Onset (Day 0-28) and Observation periods (Day 29 to last study visit or last dose+56 days, whichever is earlier); ‡Pre-study ABR derived from medical records; ^Patients transitioned to Phase 2 OLE as of data cut-off;

Figure 17A

| Patient | Prior Tx | Pre-study ABR[‡] | Original Phase 1 Dose | Current Dose (qM) | Observation Period | | | | |
|---|---|---|---|---|---|---|---|---|---|
| | | | | | Days | All Bleeds, n | ABR | Spontaneous Bleeds, n | AsBR |
| B2-4 | OD | 26 | 45 mcg/kg qW | 50 mg | 162 | 4 | 9.0 | 2 | 4.5 |
| B2-5 | OD | 22 | 45 mcg/kg qW | 50 mg | 162 | 0 | 0 | 0 | 0 |
| B3-1 | PPx | 4 | 75 mcg/kg qW | 50 mg | 63 | 0 | 0 | 0 | 0 |
| B3-3 | PPx | 4 | 75 mcg/kg qW | 50 mg | 167 | 0 | 0 | 0 | 0 |
| C1-1 | PPx | 2 | 225 mcg/kg qM | 50 mg | 335 | 4 | 4.4 | 3 | 3.3 |
| C1-2 | PPx | 0 | 225 mcg/kg qM | 50 mg | 189 | 1 | 2.0 | 0 | 0 |
| C1-3 | PPx | 0 | 225 mcg/kg qM | 50 mg | 148 | 2 | 4.9 | 0 | 0 |
| C2-2 | OD | 38 | 450 mcg/kg qM | 50 mg | 174 | 0 | 0 | 0 | 0 |
| C3-1^ | PPx | 0 | 900 mcg/kg qM | 80 mg | 373 | 0 | 0 | 0 | 0 |
| C3-2 | OD | 20 | 900 mcg/kg qM | 80 mg | 133 | 13 | 35.7 | 0 | 0 |
| C3-3 | OD | 32 | 900 mcg/kg qM | 80 mg | 162 | 0 | 0 | 0 | 0 |
| C4-1^ | PPx | 0 | 1800 mcg/kg qM | 80 mg | 329 | 0 | 0 | 0 | 0 |
| C4-2 | OD | 24 | 1800 mcg/kg qM | 80 mg | 169 | 0 | 0 | 0 | 0 |
| C4-3 | PPx | 0 | 1800 mcg/kg qM | 80 mg | 170 | 1 | 2.1 | 1 | 2.1 |
| C5-5^ | PPx | 6 | 80 mg qM | 80 mg | 261 | 3 | 4.2 | 1 | 1.4 |
| C5-6^ | PPx | 0 | 80 mg qM | 80 mg | 224 | 2 | 3.3 | 1 | 1.6 |

OLE, open-label extension; qW, weekly; qM, monthly; ABR, annualized bleeding rate; AsBR, annualized spontaneous bleeding rate
^Post hoc analysis of treated bleed events during observation period (Day 29 to last study visit or last dose+56 days, whichever is earlier); ‡Pre-study ABR derived from medical records
^Patients C3-1, C4-1, C5-5, and C5-6 had no treatment interruption and therefore continuous observation period from Phase 1

Figure 20A

METHODS AND COMPOSITIONS FOR TREATING A SERPINC1-ASSOCIATED DISORDER

RELATED APPLICATIONS

This application claims the benefit of priority to U.S. Provisional Patent Application No. 62/264,013, filed on Dec. 7, 2015, to U.S. Provisional Patent Application No. 62/315,228, filed on Mar. 30, 2016, to U.S. Provisional Patent Application No. 62/366,304, filed on Jul. 25, 2016, and to U.S. Provisional Patent Application No. 62/429,241, filed on Dec. 2, 2016. The entire contents of each of the foregoing patent applications are hereby incorporated herein by reference.

This application is related to U.S. Provisional Patent Application No. 61/992,057, filed on May 12, 2014, U.S. Provisional Patent Application No. 62/089,018, filed Dec. 8, 2014, U.S. Provisional Patent Application No. 62/102,281, filed Jan. 12, 2015, and PCT Patent Application No. PCT/US2015/030337, filed on May 12, 2015. The entire contents of each of the foregoing patent applications are hereby incorporated herein by reference.

In addition, this application is related to U.S. Provisional Patent Application No. 61/638,952, filed on Apr. 26, 2012, U.S. Provisional Patent Application No. 61/669,249, filed on Jul. 9, 2012, U.S. Provisional Patent Application No. 61/734,573, filed on Dec. 7, 2012, U.S. patent application Ser. No. 13/837,129, filed on Mar. 15, 2013, now U.S. Pat. No. 9,127,274, U.S. patent application Ser. No. 14/806,084, filed on Jul. 22, 2015, now U.S. Pat. No. 9,376,680, U.S. patent application Ser. No. 15/070,358, filed on Mar. 15, 2016, and PCT Patent Application No. PCT/US2013/038218, filed on Apr. 25, 2013. This application is also related to PCT Patent Application No. PCT/US2012/065601, filed on Nov. 16, 2012. The entire contents of each of the foregoing patent applications are hereby incorporated herein by reference.

SEQUENCE LISTING

The instant application contains a Sequence Listing which has been submitted electronically in ASCII format and is hereby incorporated by reference in its entirety. Said ASCII copy, created on Dec. 6, 2016, is named 121301-05205_SL.TXT and is 21,185 bytes in size.

BACKGROUND OF THE INVENTION

Serpinc1 is a member of the serine proteinase inhibitor (serpin) superfamily. Serpinc1 is a plasma protease inhibitor that inhibits thrombin as well as other activated serine proteases of the coagulation system, such as factors X, IX, XI, XII and VII and, thus, regulates the blood coagulation cascade. The anticoagulant activity of Serpinc1 is enhanced by the presence of heparin and other related glycosaminoglycans which catalyze the formation of thrombin:antithrombin (TAT) complexes.

Bleeding disorders, either inherited or acquired, are conditions in which there is inadequate blood clotting. For example, hemophilia is a group of hereditary genetic bleeding disorders that impair the body's ability to control blood clotting or coagulation. Hemophilia A is a recessive X-linked genetic disorder involving a lack of functional clotting Factor VIII and represents 80% of hemophilia cases. Hemophilia B is a recessive X-linked genetic disorder involving a lack of functional clotting Factor IX. It comprises approximately 20% of haemophilia cases. Hemophilia C is an autosomal genetic disorder involving a lack of functional clotting Factor XI. Hemophilia C is not completely recessive, as heterozygous individuals also show increased bleeding.

Although at present there is no cure for hemophilia, it can be controlled with regular infusions of the deficient clotting factor, e.g., factor VIII in hemophilia A. However, some hemophiliacs develop antibodies (inhibitors) against the replacement factors given to them and, thus, become refractory to replacement coagulation factor. Accordingly, bleeds in such subjects cannot be properly controlled.

The development of high-titer inhibitors to, for example, factor VIII and other coagulation factors is the most serious complication of hemophilia therapy and makes treatment of bleeds very challenging. Currently, the only strategies to stop bleeds in such subjects are the use of "bypassing agents" such as factor eight inhibitor bypass activity (FEIBA) and activated recombinant factor VII (rFVIIa), plasmapheresis, continuous factor replacement, and immune tolerance therapy, none of which are completely effective. Accordingly, there is a need in the art for alternative treatments for subjects having a bleeding disorder, such as hemophilia.

SUMMARY OF THE INVENTION

The present invention provides methods for treating a subject having a disorder that would benefit from inhibiting or reducing the expression of a Serpinc1 gene, e.g., a bleeding disorder, such as hemophilia, using iRNA compositions which effect the RNA-induced silencing complex (RISC)-mediated cleavage of RNA transcripts of a Serpinc1 gene for inhibiting the expression of a Serpinc1 gene.

The present invention is based, at least in part, on the surprising discovery that very low doses (e.g., doses at least about 30 times lower than doses taught in the art) of a GalNAc linked double stranded RNAi agent comprising particular chemical modifications shows an exceptional potency to inhibit expression of Serpinc1, as well as an exceptional duration of inhibition of Serpinc1 expression. Specifically, low doses of RNAi agents including a GalNAc ligand and a sense strand and an antisense strand in which substantially all of the nucleotides are modified, such as RNAi agents including one or more motifs of three identical modifications on three consecutive nucleotides, including one such motif at or near the cleavage site of the agents, six phosphorothioate linkages, and a GalNAc ligand are shown herein to be exceptionally effective and durable in silencing the activity of the Serpinc1 gene.

Accordingly, in one aspect the present invention provides methods of preventing at least one symptom in a subject having a disorder that would benefit from reduction in Serpinc1 expression. The methods include administering to the subject a dose of about 0.200 mg/kg to about 1.825 mg/kg of a double stranded RNAi agent which comprises a sense strand and an antisense strand forming a double stranded region, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5, wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand, e.g., a ligand is attached at the 3'-terminus of the sense strand.

In another aspect, the present invention provides methods of treating a subject having a disorder that would benefit from reduction in Serpinc1 expression. The methods include administering to the subject a dose of about 0.200 mg/kg to about 1.825 mg/kg of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5, wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In one embodiment, all of the nucleotides of the sense strand and all of the nucleotides of the antisense strand are modified nucleotides.

In another embodiment, the sense strand and the antisense strand comprise a region of complementarity which comprises at least 15 contiguous nucleotides differing by no more than 3 nucleotides from any one of the sequences listed in any one of Tables 2 and 3.

In some embodiments, the modified nucleotides are independently selected from the group consisting of a 2'-O-methyl modified nucleotide, a 2'-fluoro modified nucleotide, a nucleotide comprising a 5'-phosphorothioate group, and a terminal nucleotide linked to a cholesteryl derivative or a dodecanoic acid bisdecylamide group. In further embodiments, the modified nucleotide is selected from the group consisting of a 2'-deoxy-2'-fluoro modified nucleotide, a 2'-deoxy-modified nucleotide, a locked nucleotide, an unlocked nucleotide a conformationally restricted nucleotide, a contrained ethyl nucleotide, an abasic nucleotide, a 2'-amino-modified nucleotide, a 2'-alkyl-modified nucleotide, a 2'-O-allyl modified nucleotide, a 2'-C-allyl modified nucleotide, a 2'-hydroxyl modified nucleotide, a morpholino nucleotide, a phosphoramidate, and a non-natural base comprising nucleotide.

In another embodiment of the double stranded RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

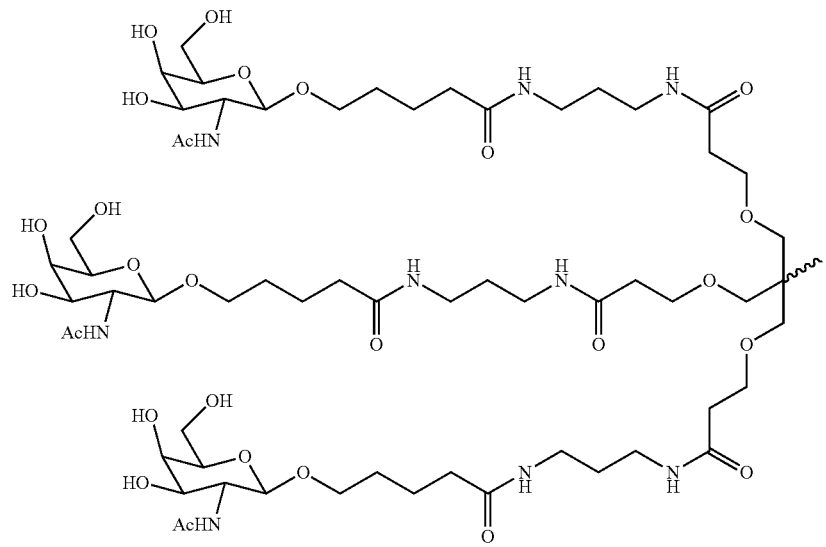

In another aspect the present invention provides methods of preventing at least one symptom in a subject having a disorder that would benefit from reduction in Serpinc1 expression. The methods include administering to the subject a dose of about 0.200 mg/kg to about 1.825 mg/kg of a double stranded RNAi agent, wherein the double stranded RNAi agent comprises a sense strand complementary to an antisense strand, wherein the antisense strand comprises a region of complementary to part of an mRNA encoding Serpinc1, wherein each strand is about 14 to about 30 nucleotides in length, wherein the double stranded RNAi agent is represented by formula (IIIe):

```
sense:        5'-N_a-Y Y Y-N_a-3'          (IIIe)
antisense:    3'n_p'-N_a'-Y'Y'Y'-N_a'-5'
``` wherein:

$n_p'$ is a 2 nucleotide overhang and each nucleotide within $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand and the antisense strand each independently comprise two phosphorothioate linkages at the 5'-terminus; and wherein the sense strand is conjugated to at least one ligand, wherein the ligand is one or more GalNAc derivatives attached through a monovalent, a bivalent, or a trivalent branched linker, thereby preventing at least one symptom in the subject having a disorder that would benefit from reduction in Serpinc1 expression.

In another aspect, the present invention provides methods of treating a subject having a disorder that would benefit from reduction in Serpinc1 expression. The methods include administering to the subject a dose of about 0.200 mg/kg to about 1.825 mg/kg of a double stranded RNAi agent, wherein the double stranded RNAi agent comprises a sense strand complementary to an antisense strand, wherein the antisense strand comprises a region of complementary to part of an mRNA encoding Serpinc1, wherein each strand is about 14 to about 30 nucleotides in length, wherein the double stranded RNAi agent is represented by formula (IIIe):

```
sense:        5'-N_a-Y Y Y-N_a-3'          (IIIe)
antisense:    3'n_p'-N_a'-Y'Y'Y'-N_a'-5'
``` wherein:

$n_p'$ is a 2 nucleotide overhang and each nucleotide within $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand and the antisense strand each independently comprise two phosphorothioate linkages at the 5'-terminus; and wherein the sense strand is conjugated to at least one ligand, wherein the ligand is one or more GalNAc derivatives attached through a monovalent, a bivalent or a trivalent branched linker, thereby preventing at least one symptom in the subject having a disorder that would benefit from reduction in Serpinc1 expression.

In one embodiment, the double stranded RNAi agent is administered to the subject in a single dose or in two or more doses, e.g., in 3, 4, 5, or 6 doses.

In one embodiment, the double stranded RNAi agent is administered to the subject once a month, once every six weeks, once every 2 months, once a quarter, or as needed.

The double stranded RNAi agent may be administered to the subject as, e.g., a monthly dose of about 0.200 to about 1.825 mg/kg, 0.200 to about 1.800 mg/kg, about 0.200 to about 1.700 mg/kg, about 0.200 to about 1.600 mg/kg, about 0.200 to about 1.500 mg/kg, about 0.200 to about 1.400 mg/kg, about 0.200 to about 1.400 mg/kg, about 0.200 to about 1.200 mg/kg, about 0.200 to about 1.100 mg/kg, about 0.200 to about 1.000 mg/kg, about 0.200 to about 0.900 mg/kg, about 0.200 to about 0.800 mg/kg, about 0.200 to about 0.700 mg/kg, about 0.200 to about 0.600 mg/kg, about 0.200 to about 0.500 mg/kg, about 0.200 to about 0.400 mg/kg, about 0.225 to about 1.825 mg/kg, about 0.225 to about 1.800 mg/kg, about 0.225 to about 1.700 mg/kg, about 0.225 to about 1.600 mg/kg, about 0.225 to about 1.500 mg/kg, about 0.225 to about 1.400 mg/kg, about 0.225 to about 1.400 mg/kg, about 0.225 to about 1.200 mg/kg, about 0.225 to about 1.100 mg/kg, about 0.225 to about 1.000 mg/kg, about 0.225 to about 0.900 mg/kg, about 0.225 to about 0.800 mg/kg, about 0.225 to about 0.700 mg/kg, about 0.225 to about 0.600 mg/kg, about 0.225 to about 0.500 mg/kg, about 0.225 to about 0.400 mg/kg, about 0.250 to about 1.825 mg/kg, about 0.250 to about 1.800 mg/kg, about 0.250 to about 1.700 mg/kg, about 0.250 to about 1.600 mg/kg, about 0.250 to about 1.500 mg/kg, about 0.250 to about 1.400 mg/kg, about 0.250 to about 1.400 mg/kg, about 0.250 to about 1.200 mg/kg, about 0.250 to about 1.100 mg/kg, about 0.250 to about 1.000 mg/kg, about 0.250 to about 0.900 mg/kg, about 0.250 to about 0.800 mg/kg, about 0.250 to about 0.700 mg/kg, about 0.250 to about 0.600 mg/kg, about 0.250 to about 0.500 mg/kg, about 0.250 to about 0.400 mg/kg, about 0.425 to about 1.825 mg/kg, about 0.425 to about 1.800 mg/kg, about 0.425 to about 1.700 mg/kg, about 0.425 to about 1.600 mg/kg, about 0.425 to about 1.500 mg/kg, about 0.425 to about 1.400 mg/kg, about 0.425 to about 1.400 mg/kg, about 0.425 to about 1.200 mg/kg, about 0.425 to about 1.100 mg/kg, about 0.425 to about 1.000 mg/kg, about 0.425 to about 0.900 mg/kg, about 0.425 to about 0.800 mg/kg, about 0.425 to about 0.700 mg/kg, about 0.425 to about 0.600 mg/kg, about 0.425 to about 0.500 mg/kg, about 0.450 to about 1.825 mg/kg, about 0.450 to about 1.800 mg/kg, about 0.450 to about 1.700 mg/kg, about 0.450 to about 1.600 mg/kg, about 0.450 to about 1.500 mg/kg, about 0.450 to about 1.400 mg/kg, about 0.450 to about 1.400 mg/kg, about 0.450 to about 1.200 mg/kg, about 0.450 to about 1.100 mg/kg, about 0.450 to about 1.000 mg/kg, about 0.450 to about 0.900 mg/kg, about 0.450 to about 0.800 mg/kg, about 0.450 to about 0.700 mg/kg, about 0.450 to about 0.600 mg/kg, about 0.450 to about 0.500 mg/kg, about 0.475 to about 1.825 mg/kg, about 0.475 to about 1.800 mg/kg, about 0.475 to about 1.700 mg/kg, about 0.475 to about 1.600 mg/kg, about 0.475 to about 1.500 mg/kg, about 0.475 to about 1.400 mg/kg, about 0.475 to about 1.400 mg/kg, about 0.475 to about 1.200 mg/kg, about 0.475 to about 1.100 mg/kg, about 0.475 to about 1.000 mg/kg, about 0.475 to about 0.900 mg/kg, about 0.475 to about 0.800 mg/kg, about 0.475 to about 0.700 mg/kg, about 0.475 to about 0.600 mg/kg, about 0.475 to about 0.500 mg/kg, about 0.875 to about 1.825 mg/kg, about 0.875 to about 1.800 mg/kg, about 0.875 to about 1.700 mg/kg, about 0.875 to about 1.600 mg/kg, about 0.875 to about 1.500 mg/kg, about 0.875 to about 1.400 mg/kg, about 0.875 to about 1.400 mg/kg, about 0.875 to about 1.200 mg/kg, about 0.875 to about 1.100 mg/kg, about 0.875 to about 1.000 mg/kg, about 0.875 to about 0.900 mg/kg, about 0.900 to about 1.825 mg/kg, about 0.900 to about 1.800 mg/kg, about 0.900 to about 1.700 mg/kg, about 0.900 to about 1.600 mg/kg, about 0.900 to about 1.500 mg/kg, about 0.900 to about 1.400 mg/kg, about 0.900 to about 1.400 mg/kg, about 0.900 to about 1.200 mg/kg, about 0.900 to about 1.100 mg/kg, about 0.900 to about 1.000 mg/kg, about 0.925 to about 1.825 mg/kg, about 0.925 to about 1.800 mg/kg, about 0.925 to about 1.700 mg/kg, about 0.925 to about 1.600 mg/kg, about 0.925 to about 1.500 mg/kg, about 0.925 to about 1.400 mg/kg, about 0.925 to about 1.400 mg/kg, about 0.925 to about 1.200 mg/kg, about 0.925 to about 1.100 mg/kg, or about 0.925 to about 1.000 mg/kg, as e.g., a monthly dose for one, two, three, four, five, six, seven, eight months, or more.

The subject may be a human, such as a human having a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the administration of the double stranded RNAi agent to the subject causes an increase in blood clotting and/or a decrease in Serpinc1 protein accumulation.

In one embodiment, the methods further comprise measuring thrombin levels in the subject.

The double stranded RNAi agent may be administered subcutaneously or intravenously.

In one embodiment, substantially all of the nucleotides of the antisense strand and substantially all of the nucleotides of the sense strand of the RNAi agent comprise a modification selected from the group consisting of a 2'-O-methyl modification and a 2'-fluoro modification. In one embodiment, all of the nucleotides of the sense strand and all of the nucleotides of the antisense of the RNAi agent strand are modified nucleotides.

In one embodiment, the YYY motif occurs at or near the cleavage site of the sense strand.

In one embodiment, the Y'Y'Y' motif occurs at the 11, 12 and 13 positions of the antisense strand from the 5'-end.

The double stranded region may be 15-30 nucleotide pairs in length, 17-23 nucleotide pairs in length, 17-25 nucleotide pairs in length, 23-27 nucleotide pairs in length, 19-21 nucleotide pairs in length, or 21-23 nucleotide pairs in length.

Each strand may have 15-30 nucleotides, or 19-30 nucleotides.

In one embodiment, the sense strand has a total of 21 nucleotides and the antisense strand has a total of 23 nucleotides.

In one embodiment, the ligand is

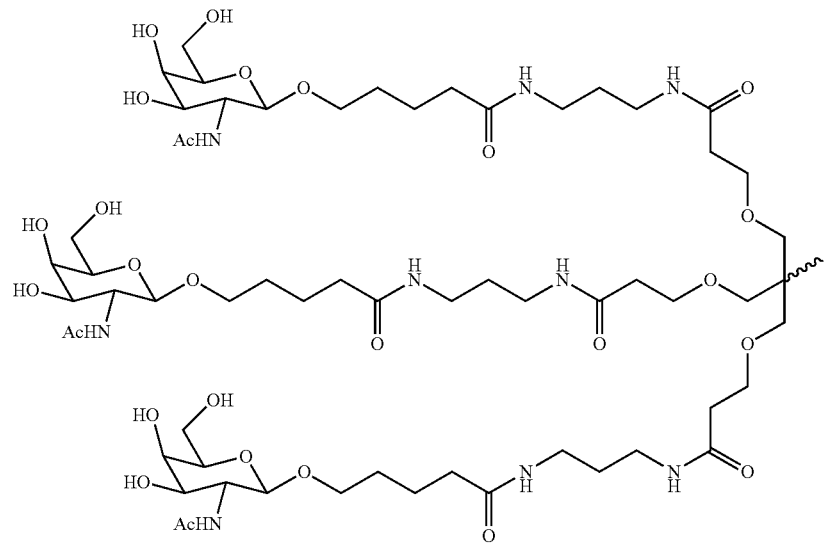

In one embodiment, the ligand is attached to the 3' end of the sense strand.

In one embodiment, the RNAi agent is conjugated to the ligand as shown in the following schematic

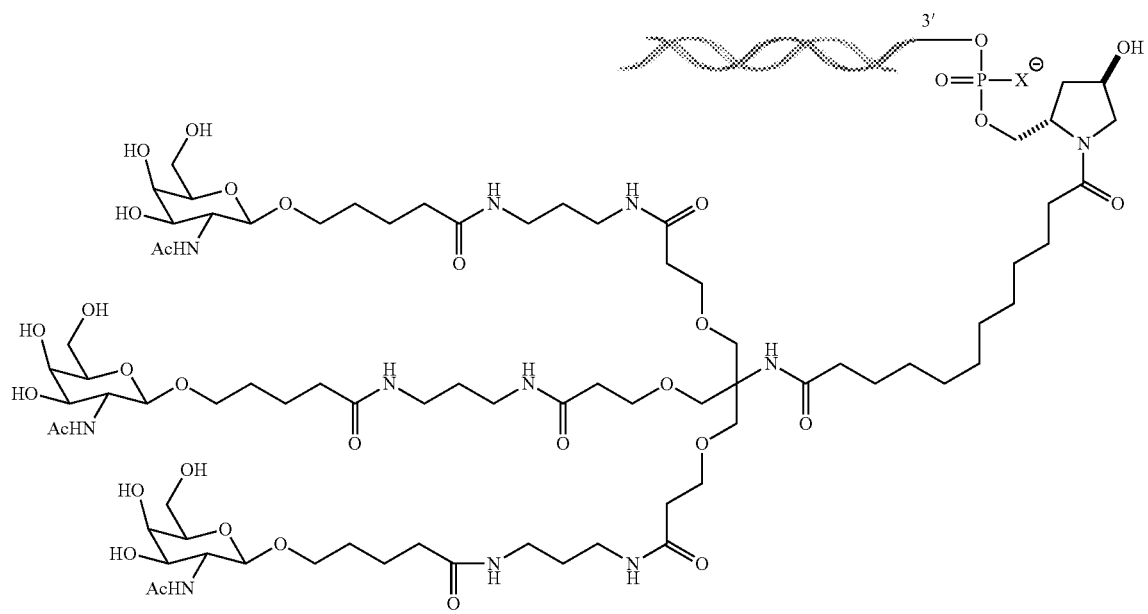

wherein X is O or S.

In one embodiment, the base pair at the 1 position of the 5'-end of the antisense strand of the duplex is an AU base pair.

In one embodiment, the RNAi agent is AD-57213 ((Sense (5' to 3'): GfsgsUfuAfaCfaCfCfAfuUfuAfcUfuCfaAf (SEQ ID NO:13); Antisense (5' to 3'): usUfsgAfaGfuAfaAfuggUfgUfuAfaCfcsasg (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage)).

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In one aspect, the present invention provides methods of preventing at least one symptom in a subject having a disorder that would benefit from reduction in Serpinc1 expression. The methods include administering to the subject a dose of about 0.200 mg/kg to about 1.825 mg/kg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In another aspect the present invention provides methods of treating a subject having a disorder that would benefit from reduction in Serpinc1 expression. The methods include administering to the subject a dose of about 0.200 mg/kg to about 1.825 mg/kg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

The double stranded RNAi agent may be administered to the subject in two or more doses.

In one embodiment, the double stranded RNAi agent is administered to the subject once a month. In another embodiment, the double stranded RNAi agent is administered to the subject once every six weeks. In one embodiment, the double stranded RNAi agent is administered to the subject once every 2 months. In yet another embodiment, the double stranded RNAi agent is administered to the subject once a quarter.

The double stranded RNAi agent may be administered to the subject as, e.g., a monthly dose of about 0.200 to about 1.825 mg/kg, 0.200 to about 1.800 mg/kg, about 0.200 to about 1.700 mg/kg, about 0.200 to about 1.600 mg/kg, about 0.200 to about 1.500 mg/kg, about 0.200 to about 1.400 mg/kg, about 0.200 to about 1.400 mg/kg, about 0.200 to about 1.200 mg/kg, about 0.200 to about 1.100 mg/kg, about 0.200 to about 1.000 mg/kg, about 0.200 to about 0.900 mg/kg, about 0.200 to about 0.800 mg/kg, about 0.200 to about 0.700 mg/kg, about 0.200 to about 0.600 mg/kg, about 0.200 to about 0.500 mg/kg, about 0.200 to about 0.400 mg/kg, about 0.225 to about 1.825 mg/kg, about 0.225 to about 1.800 mg/kg, about 0.225 to about 1.700 mg/kg, about 0.225 to about 1.600 mg/kg, about 0.225 to about 1.500 mg/kg, about 0.225 to about 1.400 mg/kg, about 0.225 to about 1.400 mg/kg, about 0.225 to about 1.200 mg/kg, about 0.225 to about 1.100 mg/kg, about 0.225 to about 1.000 mg/kg, about 0.225 to about 0.900 mg/kg, about 0.225 to about 0.800 mg/kg, about 0.225 to about 0.700 mg/kg, about 0.225 to about 0.600 mg/kg, about 0.225 to about 0.500 mg/kg, about 0.225 to about 0.400 mg/kg, about 0.250 to about 1.825 mg/kg, about 0.250 to about 1.800 mg/kg, about 0.250 to about 1.700 mg/kg, about 0.250 to about 1.600 mg/kg, about 0.250 to about 1.500 mg/kg, about 0.250 to about 1.400 mg/kg, about 0.250 to about 1.400 mg/kg, about 0.250 to about 1.200 mg/kg, about 0.250 to about 1.100 mg/kg, about 0.250 to about 1.000 mg/kg, about 0.250 to about 0.900 mg/kg, about 0.250 to about 0.800 mg/kg, about 0.250 to about 0.700 mg/kg, about 0.250 to about 0.600 mg/kg, about 0.250 to about 0.500 mg/kg, about 0.250 to about 0.400 mg/kg, about 0.425 to about 1.825 mg/kg, about 0.425 to about 1.800 mg/kg, about 0.425 to about 1.700 mg/kg, about 0.425 to about 1.600 mg/kg, about 0.425 to about 1.500 mg/kg, about 0.425 to about 1.400 mg/kg, about 0.425 to about 1.400 mg/kg, about 0.425 to about 1.200 mg/kg, about 0.425 to about 1.100 mg/kg, about 0.425 to about 1.000 mg/kg, about 0.425 to about 0.900 mg/kg, about 0.425 to about 0.800 mg/kg, about 0.425 to about 0.700 mg/kg, about 0.425 to about 0.600 mg/kg, about 0.425 to about 0.500 mg/kg, about 0.450 to about 1.825 mg/kg, about 0.450 to about 1.800 mg/kg, about 0.450 to about 1.700 mg/kg, about 0.450 to about 1.600 mg/kg, about 0.450 to about 1.500 mg/kg, about 0.450 to about 1.400 mg/kg, about 0.450 to about 1.400 mg/kg, about 0.450 to about 1.200 mg/kg, about 0.450 to about 1.100 mg/kg, about 0.450 to about 1.000 mg/kg, about 0.450 to about 0.900 mg/kg, about 0.450 to about 0.800 mg/kg, about 0.450 to about 0.700 mg/kg, about 0.450 to about 0.600 mg/kg, about 0.450 to about 0.500 mg/kg, about 0.475 to about 1.825 mg/kg, about 0.475 to about 1.800 mg/kg, about 0.475 to about 1.700 mg/kg, about 0.475 to about 1.600 mg/kg, about 0.475 to about 1.500 mg/kg, about 0.475 to about 1.400 mg/kg, about 0.475 to about 1.400 mg/kg, about 0.475 to about 1.200 mg/kg, about 0.475 to about 1.100 mg/kg, about 0.475 to about 1.000 mg/kg, about 0.475 to about 0.900 mg/kg, about 0.475 to about 0.800 mg/kg, about 0.475 to about 0.700 mg/kg, about 0.475 to about 0.600 mg/kg, about 0.475 to about 0.500 mg/kg, about 0.875 to about 1.825 mg/kg, about 0.875 to about 1.800 mg/kg, about 0.875 to about 1.700 mg/kg, about 0.875 to about 1.600 mg/kg, about 0.875 to about 1.500 mg/kg, about 0.875 to about 1.400 mg/kg, about 0.875 to about 1.400 mg/kg, about 0.875 to about 1.200 mg/kg, about 0.875 to about 1.100 mg/kg, about 0.875 to about 1.000 mg/kg, about 0.875 to about 0.900 mg/kg, about 0.900 to about 1.825 mg/kg, about 0.900 to about 1.800 mg/kg, about 0.900 to about 1.700 mg/kg, about 0.900 to about 1.600 mg/kg, about 0.900 to about 1.500 mg/kg, about 0.900 to about 1.400 mg/kg, about 0.900 to about 1.400 mg/kg, about 0.900 to about 1.200 mg/kg, about 0.900 to about 1.100 mg/kg, about 0.900 to about 1.000 mg/kg, about 0.925 to about 1.825 mg/kg, about 0.925 to about 1.800 mg/kg, about 0.925 to about 1.700 mg/kg, about 0.925 to about 1.600 mg/kg, about 0.925 to about 1.500 mg/kg, about 0.925 to about 1.400 mg/kg, about 0.925 to about 1.400 mg/kg, about 0.925 to about 1.200 mg/kg, about 0.925 to about 1.100 mg/kg, or about 0.925 to about 1.000 mg/kg.

In some embodiments, the dose of the double stranded RNAi agent is administered to the subject as a monthly dose of about 0.200 mg/kg to about 0.250 mg/kg; or as a monthly dose of about 0.425 mg/kg to about 0.475 mg/kg; or as a monthly dose of about 0.875 mg/kg to about 0.925 mg/kg; or as a monthly dose of about 1.775 mg/kg to about 1.825 mg/kg.

In one embodiment, the double stranded RNAi agent is administered to the subject as a monthly dose of 0.225 mg/kg.

In another embodiment, the double stranded RNAi agent is administered to the subject as a monthly dose of 0.450 mg/kg.

In yet another embodiment, the double stranded RNAi agent is administered to the subject as a monthly dose of 0.900 mg/kg.

In one embodiment, the double stranded RNAi agent is administered to the subject as a monthly dose of 1.800 mg/kg.

In one embodiment, the double stranded RNAi agent is administered to the subject subcutaneously.

In one embodiment, administration of the dose of the double stranded RNAi agent to the subject lowers Serpinc1 activity in the subject by about 70% to about 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40% in the subject.

In yet another embodiment, administration of the dose of the double stranded RNAi agent to the subject decreases the annual bleed rate (ABR) of the subject by about 80 to about 95% as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the double stranded RNAi agent is administered to the subject subcutaneously.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity may be at least 17 nucleotides in length or 19 nucleotides in length.

In one embodiment, the region of complementarity is between 19 and 21 nucleotides in length. In another embodiment, the region of complementarity is between 21 and 23 nucleotides in length.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

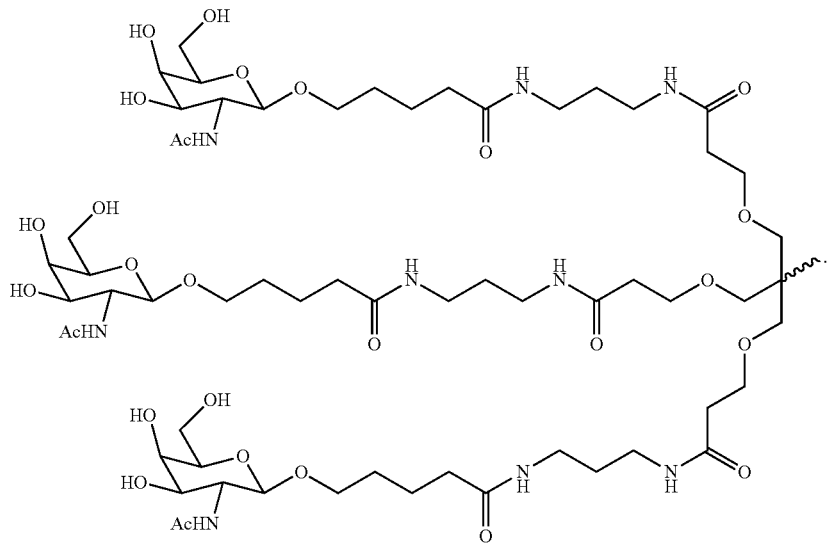 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand as shown in the following schematic

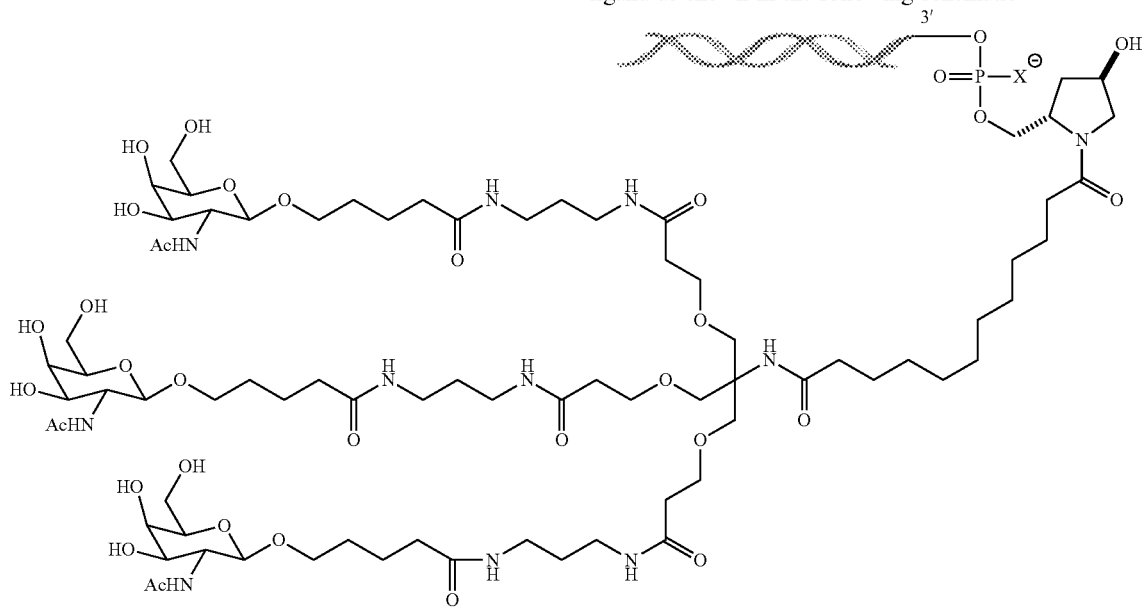

and, wherein X is O or S.

In one embodiment, the X is O.

In one embodiment, the region of complementarity consists of the nucleotide sequence of

5'-UUGAAGUAAAUGGUGUUAACCAG-3'. (SEQ ID NO: 15)

In one embodiment, the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGU-GUUAACCAG-3' (SEQ ID NO: 15).

In one embodiment, the sense strand comprises 5'-GfsgsUfuAfaCfaCfCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one aspect, the present invention provides methods of preventing at least one symptom in a subject having a disorder that would benefit from reduction in Serpinc1 expression. The methods include administering to the subject a fixed dose of about 25 mg to about 100 mg of a double stranded RNAi agent which comprises a sense strand and an antisense strand forming a double stranded region, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5, wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In another aspect, the present invention provides methods of treating a subject having a disorder that would benefit from reduction in Serpinc1 expression. The methods include administering to the subject a fixed dose of about 25 mg to about 100 mg of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5, wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In one embodiment, all of the nucleotides of the sense strand and all of the nucleotides of the antisense strand are modified nucleotides.

In another embodiment, the sense strand and the antisense strand comprise a region of complementarity which comprises at least 15 contiguous nucleotides differing by no more than 3 nucleotides from any one of the sequences listed in any one of Tables 2 and 3.

In some embodiments, the modified nucleotides are independently selected from the group consisting of a 2'-O-methyl modified nucleotide, a 2'-fluoro modified nucleotide, a nucleotide comprising a 5'-phosphorothioate group, and a terminal nucleotide linked to a cholesteryl derivative or a dodecanoic acid bisdecylamide group. In further embodiments, the modified nucleotide is selected from the group consisting of a 2'-deoxy-2'-fluoro modified nucleotide, a 2'-deoxy-modified nucleotide, a locked nucleotide, an unlocked nucleotide a conformationally restricted nucleotide, a constrained ethyl nucleotide, an abasic nucleotide, a 2'-amino-modified nucleotide, a 2'-alkyl-modified nucleotide, a 2'-O-allyl modified nucleotide, a 2'-C-allyl modified nucleotide, a 2'-hydroxyl modified nucleotide, a morpholino nucleotide, a phosphoramidate, and a non-natural base comprising nucleotide.

In another embodiment of the double stranded RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In another aspect, the present invention provides methods of preventing at least one symptom in a subject having a disorder that would benefit from reduction in Serpinc1 expression. The methods include administering to the subject a fixed dose of about 25 mg to about 100 mg of a double stranded RNAi agent, wherein the double stranded RNAi agent comprises a sense strand complementary to an antisense strand, wherein the antisense strand comprises a region of complementary to part of an mRNA encoding Serpinc1, wherein each strand is about 14 to about 30 nucleotides in length, wherein the double stranded RNAi agent is represented by formula (IIIe):

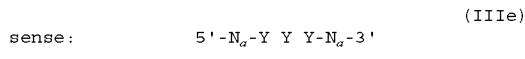

sense:      5'-$N_a$-Y Y Y-$N_a$-3' antisense:  3' $n_p$'-$N_a$'-Y'Y'Y'-$N_a$'-5' wherein:

$n_p$' is a 2 nucleotide overhang and each nucleotide within $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand and the antisense strand each independently comprise two phosphorothioate linkages at the 5'-terminus; and wherein the sense strand is conjugated to at least one ligand, wherein the ligand is one or more GalNAc derivatives attached through a monovilant, a bivalent or a trivalent branched linker, thereby preventing at least one symptom in the subject having a disorder that would benefit from reduction in Serpinc1 expression.

In another aspect, the present invention provides methods of treating a subject having a disorder that would benefit from reduction in Serpinc1 expression. The methods include administering to the subject a fixed dose of about 25 mg to about 100 mg of a double stranded RNAi agent, wherein the double stranded RNAi agent comprises a sense strand complementary to an antisense strand, wherein the antisense strand comprises a region of complementary to part of an mRNA encoding Serpinc1, wherein each strand is about 14 to about 30 nucleotides in length, wherein the double stranded RNAi agent is represented by formula (IIIe):

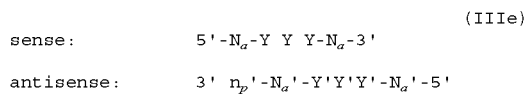

wherein:

$n_p'$ is a 2 nucleotide overhang and each nucleotide within $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand and the antisense strand each independently comprise two phosphorothioate linkages at the 5'-terminus; and wherein the sense strand is conjugated to at least one ligand, wherein the ligand is one or more GalNAc derivatives attached through a monovalent, a bivalent or a trivalent branched linker, thereby preventing at least one symptom in the subject having a disorder that would benefit from reduction in Serpinc1 expression.

In one embodiment, the double stranded RNAi agent is administered to the subject in a single dose or in two or more doses, e.g., in 3, 4, 5, or 6 doses.

In one embodiment, the double stranded RNAi agent is administered to the subject once a month, once every five weeks, once every six weeks, once every seven weeks, once every 2 months, once a quarter, or as needed.

The double stranded RNAi agent may be administered to the subject as, e.g., a fixed dose of between about 25 mg to about 100 mg, e.g., between about 25 mg to about 95 mg, between about 25 mg to about 90 mg, between about 25 mg to about 85 mg, between about 25 mg to about 80 mg, between about 25 mg to about 75 mg, between about 25 mg to about 70 mg, between about 25 mg to about 65 mg, between about 25 mg to about 60 mg, between about 25 mg to about 50 mg, between about 50 mg to about 100 mg, between about 50 mg to about 95 mg, between about 50 mg to about 90 mg, between about 50 mg to about 85 mg, between about 50 mg to about 80 mg, between about 30 mg to about 100 mg, between about 30 mg to about 90 mg, between about 30 mg to about 80 mg, between about 40 mg to about 100 mg, between about 40 mg to about 90 mg, between about 40 mg to about 80 mg, between about 60 mg to about 100 mg, between about 60 mg to about 90 mg, between about 25 mg to about 55 mg, between about 25 mg to about 65 mg, between about 30 mg to about 95 mg, between about 30 mg to about 85 mg, between about 30 mg to about 75 mg, between about 30 mg to about 65 mg, between about 30 mg to about 55 mg, between about 40 mg to about 95 mg, between about 40 mg to about 85 mg, between about 40 mg to about 75 mg, between about 40 mg to about 65 mg, between about 40 mg to about 55 mg, or between about 45 mg to about 95 mg as e.g., a fixed dose for one, two, three, four, five, six, seven, eight months, or more.

In some embodiments, the double stranded RNAi agent may be administered to the subject as a fixed dose of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

The subject may be a human, such as a human having a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the administration of the double stranded RNAi agent to the subject causes an increase in blood clotting and/or a decrease in Serpinc1 protein accumulation.

In one embodiment, the methods further comprise measuring thrombin levels in the subject.

The double stranded RNAi agent may be administered subcutaneously or intravenously.

In one embodiment, substantially all of the nucleotides of the antisense strand and substantially all of the nucleotides of the sense strand of the RNAi agent comprise a modification selected from the group consisting of a 2'-O-methyl modification and a 2'-fluoro modification. In one embodiment, all of the nucleotides of the sense strand and all of the nucleotides of the antisense of the RNAi agent strand are modified nucleotides.

In one embodiment, the YYY motif occurs at or near the cleavage site of the sense strand.

In one embodiment, the Y'Y'Y' motif occurs at the 11, 12 and 13 positions of the antisense strand from the 5'-end.

The double stranded region may be 15-30 nucleotide pairs in length, 17-23 nucleotide pairs in length, 17-25 nucleotide pairs in length, 23-27 nucleotide pairs in length, 19-21 nucleotide pairs in length, or 21-23 nucleotide pairs in length.

Each strand may have 15-30 nucleotides, or 19-30 nucleotides.

In one embodiment, the sense strand has a total of 21 nucleotides and the antisense strand has a total of 23 nucleotides.

In one embodiment, the ligand is

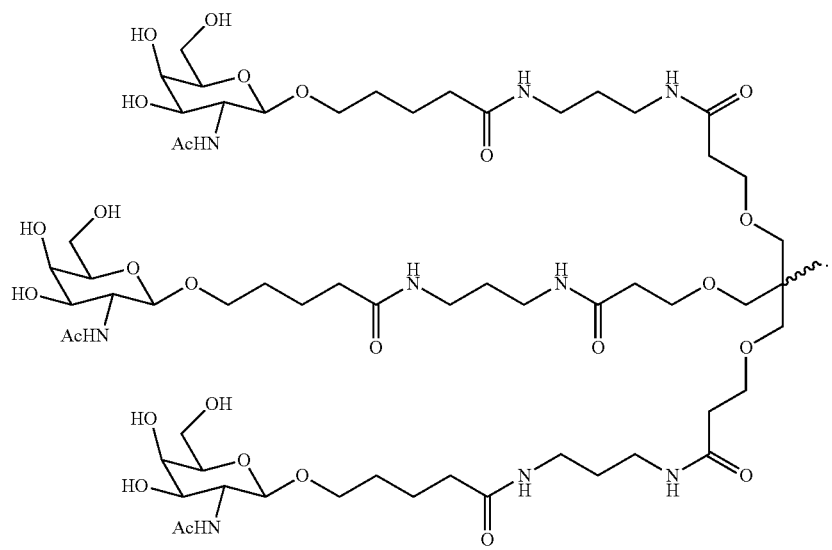 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ligand is attached to the 3' end of the sense strand.

In one embodiment, the RNAi agent is conjugated to the ligand as shown in the following schematic

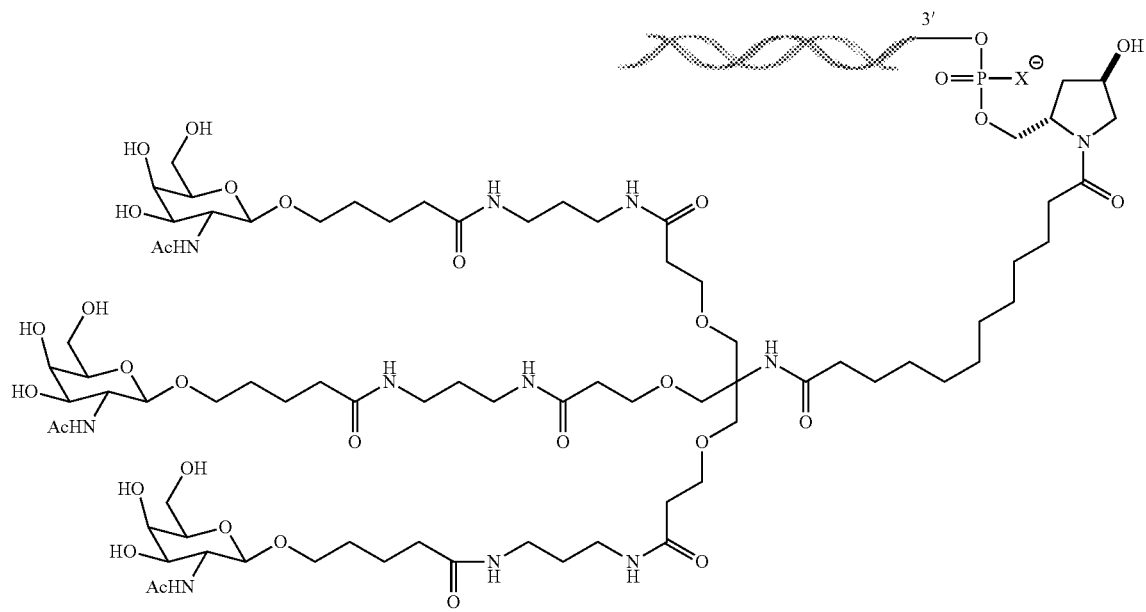

wherein X is O or S.

In one embodiment, the base pair at the 1 position of the 5'-end of the antisense strand of the duplex is an AU base pair.

In one embodiment, the RNAi agent is AD-57213 ((Sense (5' to 3'): GfsgsUfuAfaCfaCfCfAfuUfuAfcUfuCfaAf (SEQ ID NO:13); Antisense (5' to 3'): usUfsgAfaGfuAfaAfug-gUfgUfuAfaCfcsasg (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage)).

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In one aspect, the present invention provides methods of preventing at least one symptom in a subject having a disorder that would benefit from reduction in Serpinc1 expression. The methods include administering to the subject a fixed dose of about 25 mg to about 100 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In another aspect the present invention provides methods of treating a subject having a disorder that would benefit from reduction in Serpinc1 expression. The methods include administering to the subject a fixed dose of about 25 mg to about 100 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

The double stranded RNAi agent may be administered to the subject in two or more doses.

In some embodiments, the double stranded RNAi agent is administered to the subject once a month, once every five weeks, once every six weeks, once every seven weeks, once every 2 months, once a quarter, or as needed.

In one embodiment, the double stranded RNAi agent is administered to the subject once a month. In another embodiment, the double stranded RNAi agent is administered to the subject once every six weeks. In one embodiment, the double stranded RNAi agent is administered to the subject once every 2 months. In yet another embodiment, the double stranded RNAi agent is administered to the subject once a quarter.

The double stranded RNAi agent may be administered to the subject as, e.g., a fixed dose of between about 25 mg to about 100 mg, e.g., between about 25 mg to about 95 mg, between about 25 mg to about 90 mg, between about 25 mg to about 85 mg, between about 25 mg to about 80 mg, between about 25 mg to about 75 mg, between about 25 mg to about 70 mg, between about 25 mg to about 65 mg, between about 25 mg to about 60 mg, between about 25 mg to about 50 mg, between about 50 mg to about 100 mg, between about 50 mg to about 95 mg, between about 50 mg to about 90 mg, between about 50 mg to about 85 mg, between about 50 mg to about 80 mg, between about 30 mg to about 100 mg, between about 30 mg to about 90 mg, between about 30 mg to about 80 mg, between about 30 mg to about 40 mg to about 100 mg, between about 40 mg to about 90 mg, between about 40 mg to about 80 mg, between about 60 mg to about 100 mg, between about 60 mg to about 90 mg, between about 25 mg to about 55 mg, between about 25 mg to about 65 mg, between about 30 mg to about 95 mg, between about 30 mg to about 85 mg, between about 30 mg to about 75 mg, between about 30 mg to about 65 mg, between about 30 mg to about 55 mg, between about 40 mg to about 95 mg, between about 40 mg to about 85 mg, between about 40 mg to about 75 mg, between about 40 mg to about 65 mg, between about 40 mg to about 55 mg, or between about 45 mg to about 95 mg.

In some embodiments, the double stranded RNAi agent may be administered as a fixed dose of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments, the double stranded RNAi agent is administered to the subject as a fixed dose of about 25 mg; or as a fixed dose of about 50 mg; or as a fixed dose of about 80 mg; or as a fixed dose of about 100 mg.

In one embodiment, the double stranded RNAi agent is administered to the subject subcutaneously.

In one embodiment, administration of the dose of the double stranded RNAi agent to the subject lowers Serpinc1 activity in the subject by about 70% to about 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40% in the subject.

In yet another embodiment, administration of the dose of the double stranded RNAi agent to the subject decreases the annual bleed rate (ABR) of the subject by about 80 to about 95% as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the double stranded RNAi agent is administered to the subject subcutaneously.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity may be at least 17 nucleotides in length or 19 nucleotides in length.

In one embodiment, the region of complementarity is between 19 and 21 nucleotides in length. In another embodiment, the region of complementarity is between 21 and 23 nucleotides in length.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

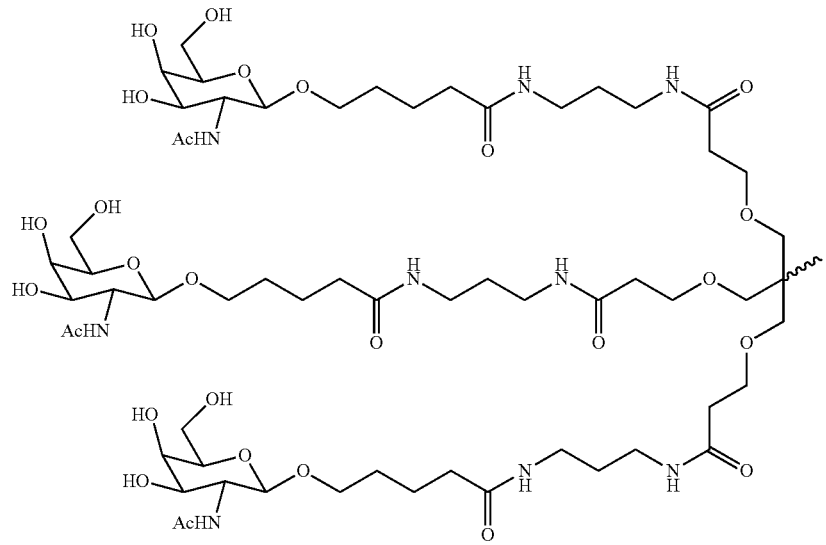

In one embodiment, the RNAi agent is conjugated to the ligand as shown in the following schematic

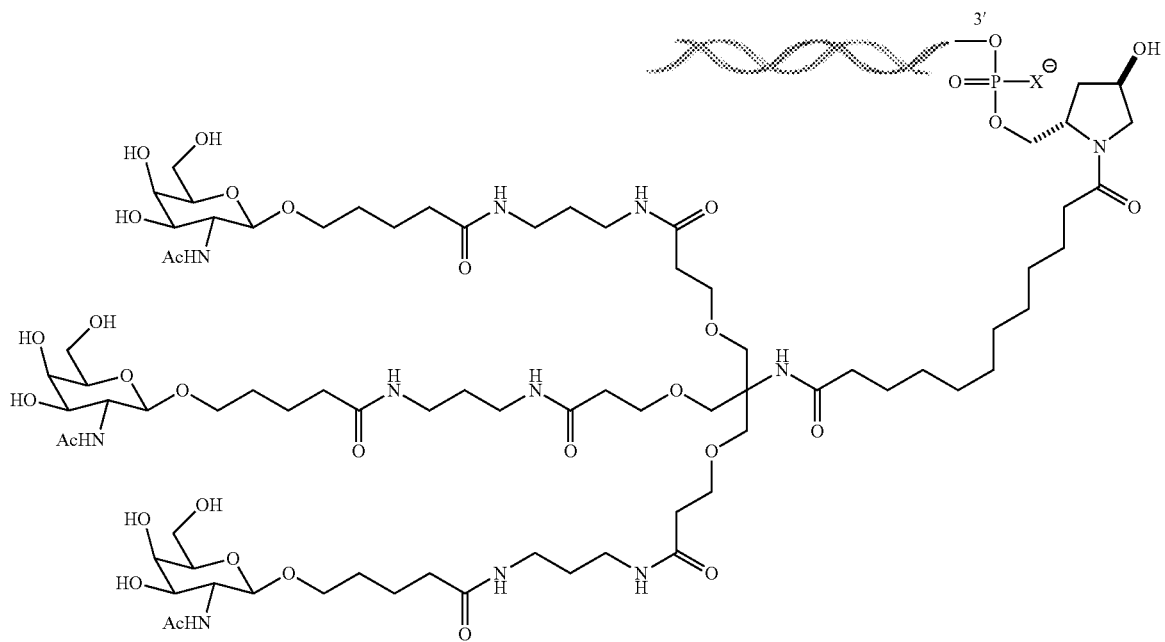

and, wherein X is O or S.

In one embodiment, the X is O.

In one embodiment, the region of complementarity consists of the nucleotide sequence of

```
                                        (SEQ ID NO: 15)
5'-UUGAAGUAAAUGGUGUUAACCAG-3'.
```

In one embodiment, the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15).

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic tion thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

In one aspect, the present invention provides methods of preventing at least one symptom in a subject having a disorder that would benefit from reduction in Serpinc1 expression. The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a disorder that would benefit

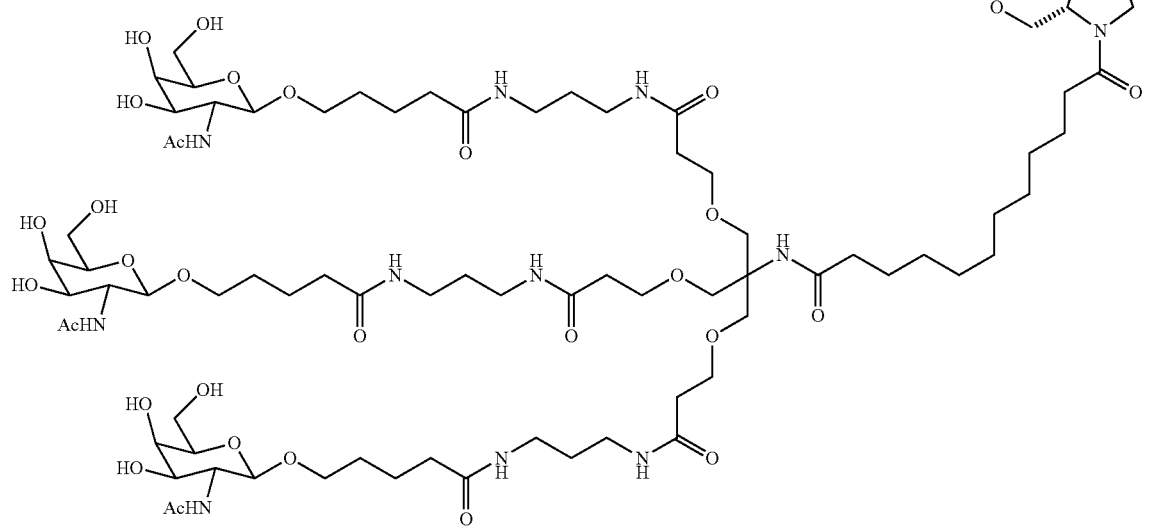

wherein X is O or S.

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof.

from reduction in Serpinc1 expression. The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one aspect, the present invention provides methods of preventing at least one symptom in a subject having a disorder that would benefit from reduction in Serpinc1 expression. The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a disorder that would benefit from reduction in Serpinc1 expression. The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one embodiment, administration of the dose of the double stranded RNAi agent to the subject lowers Serpinc1 activity in the subject by about 70% to about 95%, about 70% to about 80%, about 80% to about 90%, about 90% to about 95%, or by more than 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40%, 45%, 50%, 55%, or greater than about 60% in the subject.

In yet another embodiment, administration of the dose of the double stranded RNAi agent to the subject decreases the annual bleed rate (ABR) of the subject by about 80% to about 95%, about 80% to about 85%, about 85% to about 90%, or about 90% to about 95%, as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the double stranded RNAi agent is administered to the subject subcutaneously.

In one embodiment, the double stranded RNAi agent is administered to the subject chronically.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity may be at least 17 nucleotides in length or 19 nucleotides in length.

In one embodiment, the region of complementarity is between 19 and 21 nucleotides in length. In another embodiment, the region of complementarity is between 21 and 23 nucleotides in length.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

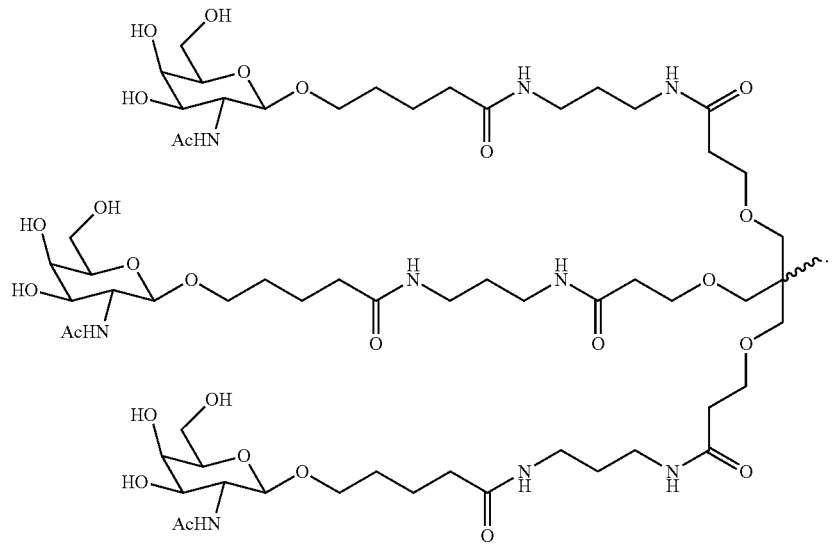 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand as shown in the following schematic In one embodiment, the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGU-GUUAACCAG-3' (SEQ ID NO: 15).

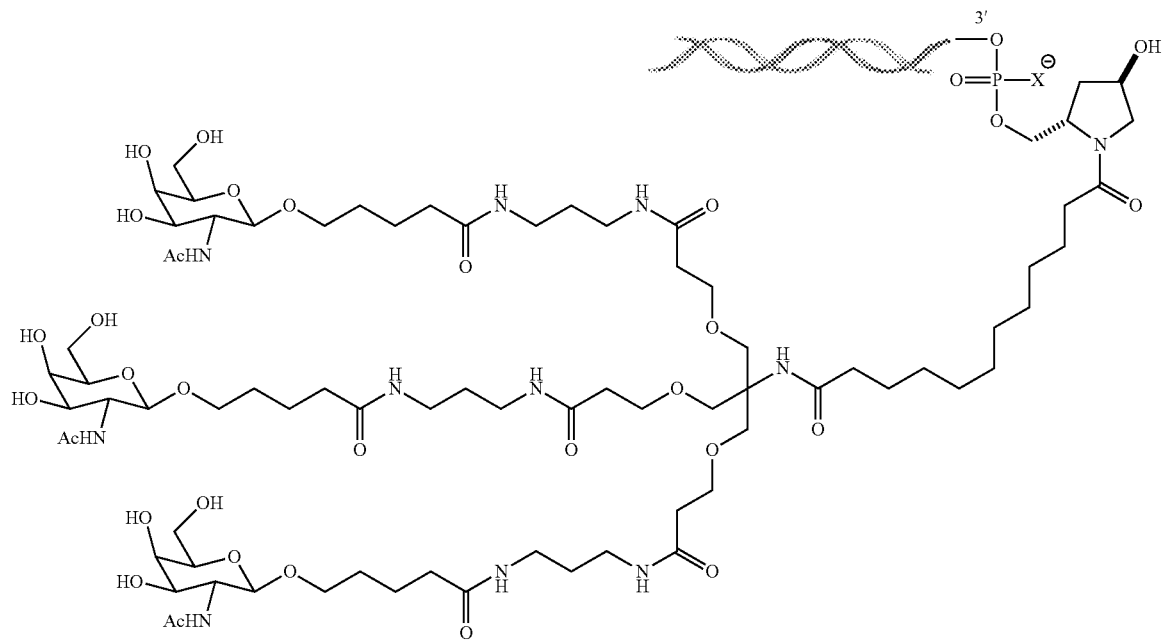

and, wherein X is O or S.

In one embodiment, the X is O.

In one embodiment, the region of complementarity consists of the nucleotide sequence of

```
                                    (SEQ ID NO: 15)
5'-UUGAAGUAAAUGGUGUUAACCAG-3'.
```

In one embodiment, the sense strand comprises 5'-GfsgsUfuAfaCfaCfCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least

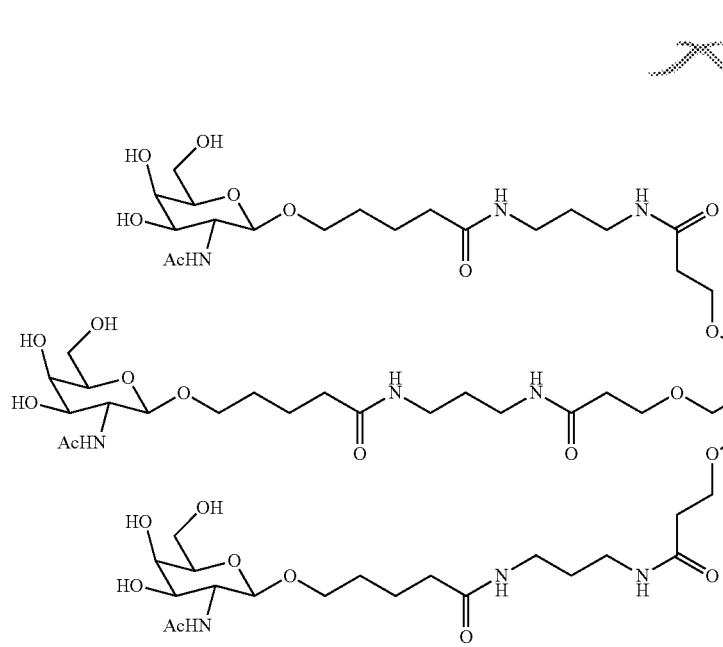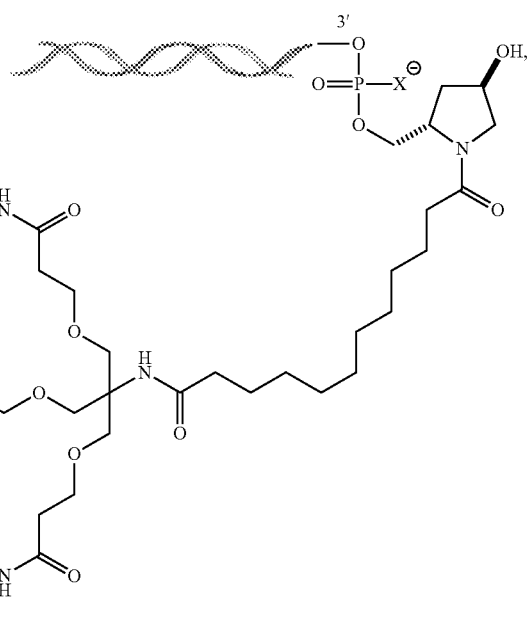

wherein X is O or S.

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

In one aspect, the present invention provides methods of preventing at least one symptom in a subject having a disorder that would benefit from reduction in Serpinc1 expression. The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi one symptom in the subject having a disorder that would benefit from reduction in Serpinc1 expression.

In another aspect, the present invention provides methods of treating a subject having a disorder that would benefit from reduction in Serpinc1 expression. The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACAC-CAUUUACUUCAA-3' (SEQ ID NO: 16), and an antisense strand comprising the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one aspect, the present invention provides methods of preventing at least one symptom in a subject having a disorder that would benefit from reduction in Serpinc1 expression. The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a disorder that would benefit from reduction in Serpinc1 expression. The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACAC-CAUUUACUUCAA-3' (SEQ ID NO: 16), and an antisense strand comprising the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one embodiment, administration of the dose of the double stranded RNAi agent to the subject lowers Serpinc1 activity in the subject by about 70% to about 95%, about 70% to about 80%, about 80% to about 90%, about 90% to about 95%, or by more than 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40%, 45%, 50%, 55%, or greater than about 60% in the subject.

In yet another embodiment, administration of the dose of the double stranded RNAi agent to the subject decreases the annual bleed rate (ABR) of the subject by about 80% to about 95%, about 80% to about 85%, about 85% to about 90%, or about 90% to about 95%, as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the double stranded RNAi agent is administered to the subject subcutaneously.

In one embodiment, the double stranded RNAi agent is administered to the subject chronically.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

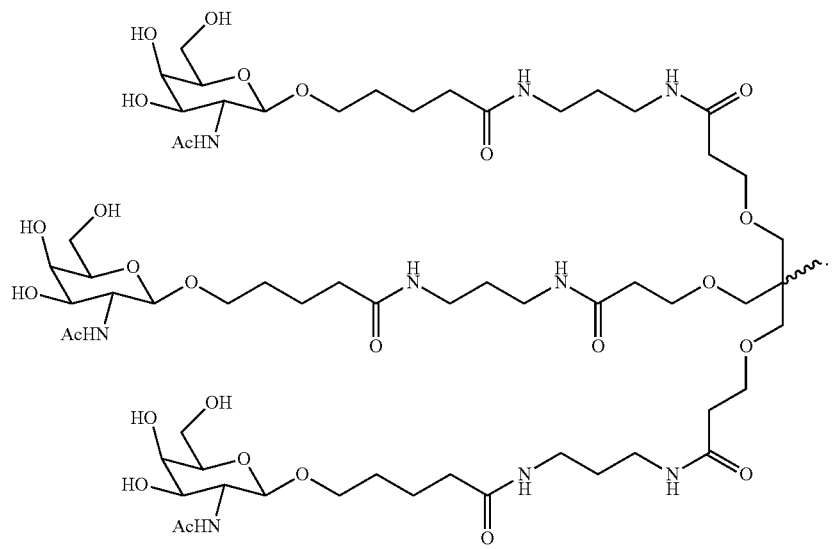 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand as shown in the following schematic

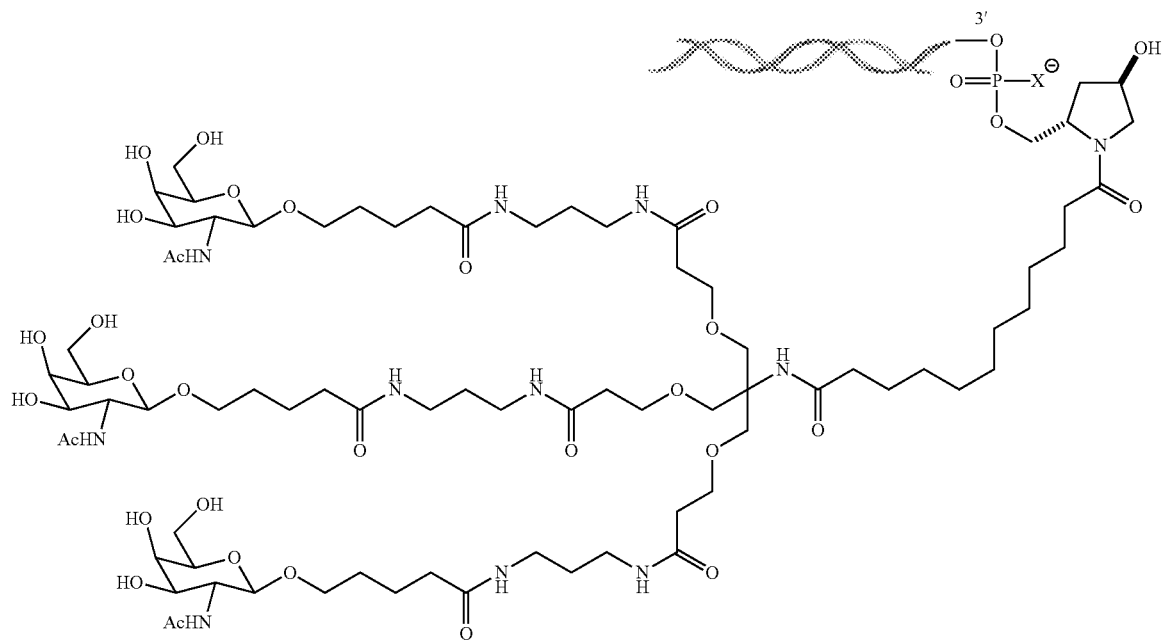

and, wherein X is O or S.

In one embodiment, the X is O.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic

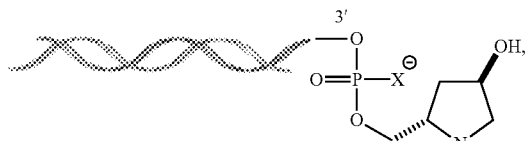
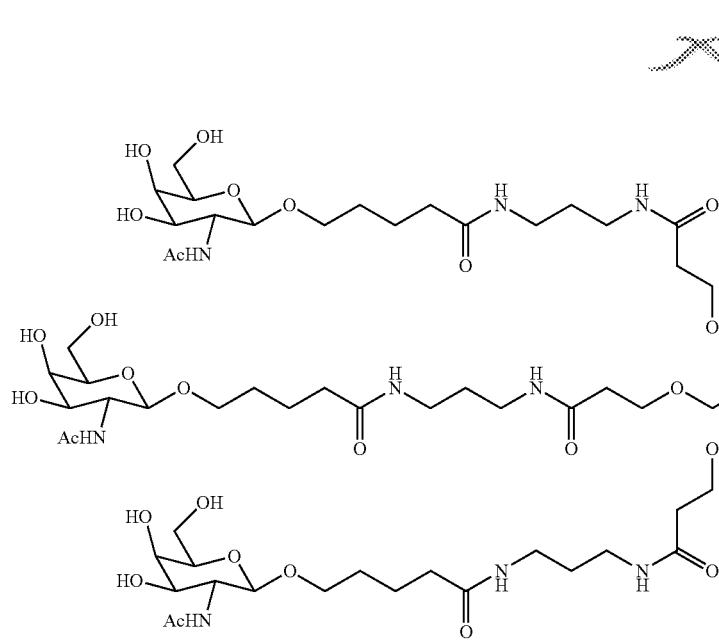

wherein X is O or S.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

In one aspect, the present invention provides methods of preventing at least one symptom in a subject having a hemophilia, e.g., hemophilia A (with or without inhibitors), hemophilia B (with or without inhibitors), or hemophilia C (with or without inhibitors). The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a hemophilia, e.g., hemophilia A (with or without inhibitors), hemophilia B (with or without inhibitors), or hemophilia C (with or without inhibitors). The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one aspect, the present invention provides methods of preventing at least one symptom in a subject having a hemophilia, e.g., hemophilia A (with or without inhibitors), hemophilia B (with or without inhibitors), or hemophilia C (with or without inhibitors). The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a hemophilia, e.g., hemophilia A (with or without inhibitors), hemophilia B (with or without inhibitors), or hemophilia C (with or without inhibitors). The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, thereby treating the subject having a disorder that would benefit from reduction in Serpinc1 expression.

In one aspect, the present invention provides methods of preventing at least one symptom in a subject having a hemophilia, e.g., hemophilia A (with or without inhibitors), hemophilia B (with or without inhibitors), or hemophilia C (with or without inhibitors). The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GfsgsUfuAfaCfaCfCfAfuUfuAfcUfuCfaAf-3' (SEQ ID NO:13) and an antisense strand comprising the nucleotide sequence of 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a hemophilia, e.g., hemophilia A (with or without inhibitors), hemophilia B (with or without inhibitors), or hemophilia C (with or without inhibitors). The methods include administering to the subject a fixed dose of about 50 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GfsgsUfuAfaCfaCfCfAfuUfuAfcUfuCfaAf-3' (SEQ ID NO:13) and an antisense strand comprising the nucleotide sequence of 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage, and wherein the sense strand is conjugated to a ligand attached at the 3'-terminus, thereby treating the subject having a disorder that would benefit from reduction in Serpinc1 expression.

In one aspect, the present invention provides methods of preventing at least one symptom in a subject having a hemophilia, e.g., hemophilia A (with or without inhibitors), hemophilia B (with or without inhibitors), or hemophilia C (with or without inhibitors). The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GfsgsUfuAfaCfaCfCfAfuUfuAfcUfuCfaAf-3' (SEQ ID NO:13) and an antisense strand comprising the nucleotide sequence of 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage, and wherein the sense strand is conjugated to a ligand attached at the 3'-terminus, thereby preventing at least one symptom in the subject having a disorder that would benefit from reduction in Serpinc1 expression.

In another aspect, the present invention provides methods of treating a subject having a hemophilia, e.g., hemophilia A (with or without inhibitors), hemophilia B (with or without inhibitors), or hemophilia C (with or without inhibitors). The methods include administering to the subject a fixed dose of about 80 mg of a double stranded ribonucleic acid (RNAi) agent, wherein the fixed dose of the double stranded RNAi agent is administered to the subject about once per month, wherein the double stranded RNAi agent comprises a sense strand comprising the nucleotide sequence of 5'-GfsgsUfuAfaCfaCfCfAfuUfuAfcUfuCfaAf-3' (SEQ ID NO:13) and an antisense strand comprising the nucleotide sequence of 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage, and wherein the sense strand is conjugated to a ligand attached at the 3'-terminus, thereby treating the subject having a disorder that would benefit from reduction in Serpinc1 expression.

In one embodiment, administration of the dose of the double stranded RNAi agent to the subject lowers Serpinc1 activity in the subject by about 70% to about 95%, about 70% to about 80%, about 80% to about 90%, about 90% to about 95%, or by more than 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40%, 45%, 50%, 55%, or greater than about 60% in the subject.

In yet another embodiment, administration of the dose of the double stranded RNAi agent to the subject decreases the annual bleed rate (ABR) of the subject by about 80% to about 95%, about 80% to about 85%, about 85% to about 90%, or about 90% to about 95%, as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

In one embodiment, the double stranded RNAi agent is administered to the subject subcutaneously.

In one embodiment, the double stranded RNAi agent is administered to the subject chronically.

In certain embodiments, the ligand is

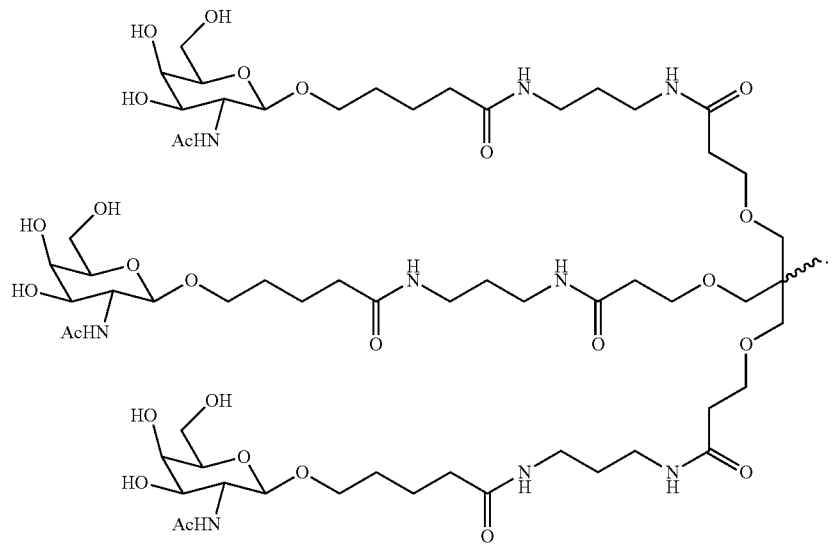 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand as shown in the following schematic

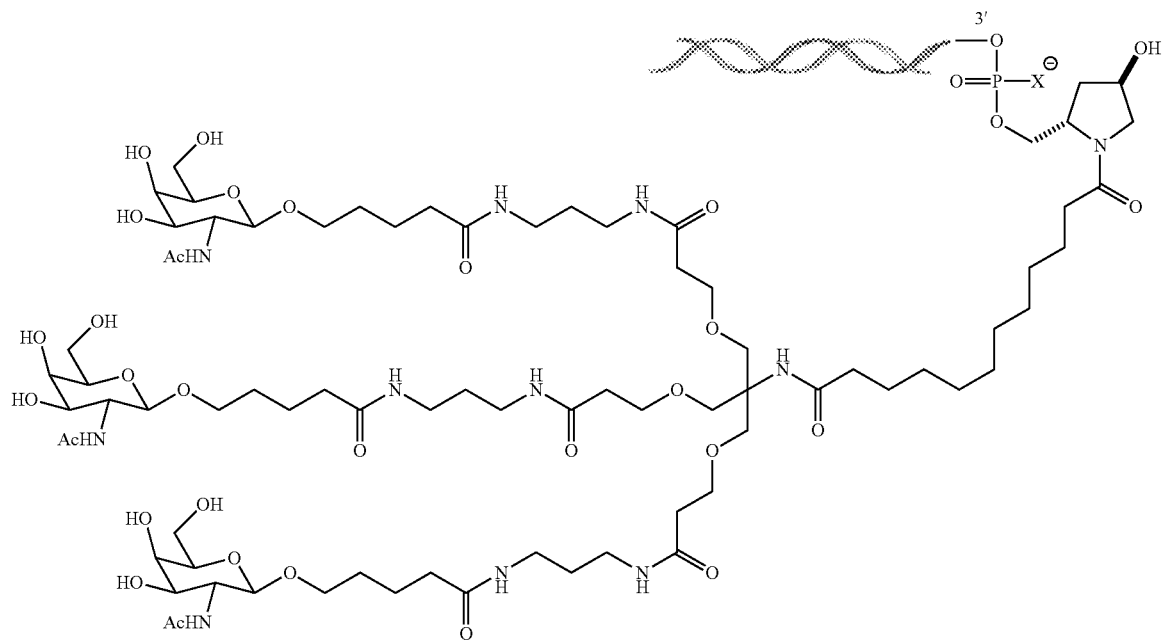

and, wherein X is O or S.

In one embodiment, the X is O.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic

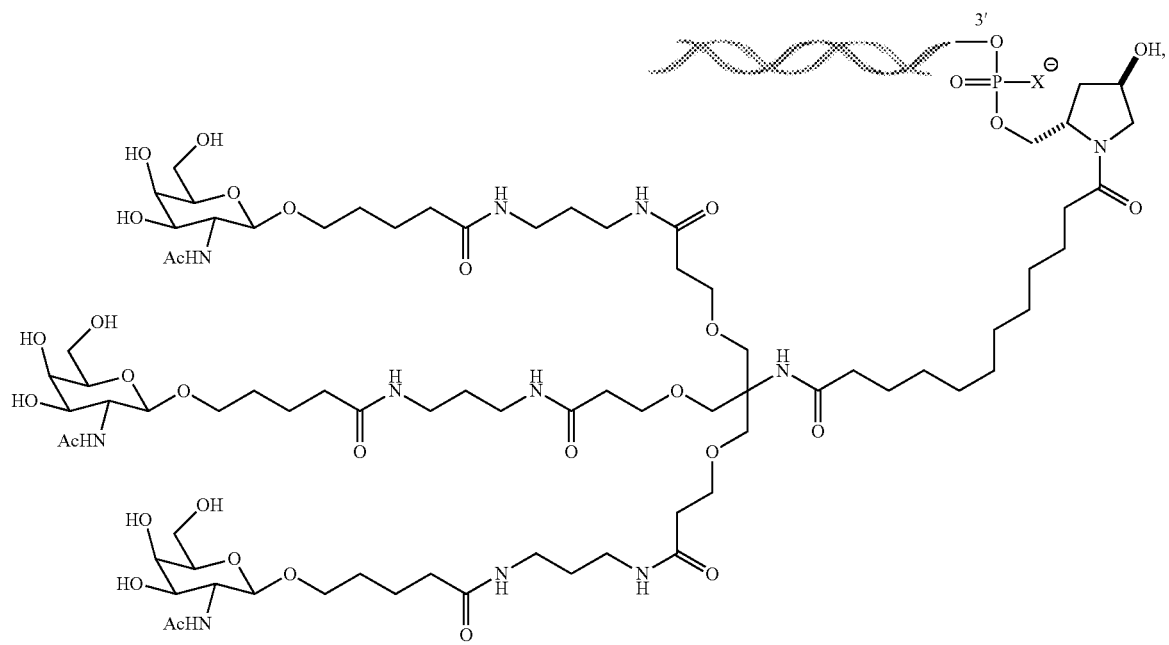

wherein X is O or S.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

In one aspect, the present invention provides methods of preventing at least one symptom in a subject having a disorder that would benefit from reduction in Serpinc1 expression. The methods include administering to the subject a fixed dose of about 40 mg to about 90 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In another aspect the present invention provides methods of treating a subject having a disorder that would benefit from reduction in Serpinc1 expression. The methods include administering to the subject a fixed dose of about 40 mg to about 90 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

The double stranded RNAi agent may be administered to the subject in two or more doses.

In some embodiments, the double stranded RNAi agent is administered to the subject once a month, once every five weeks, once every six weeks, once every seven weeks, once every 2 months, once a quarter, or as needed.

In one embodiment, the double stranded RNAi agent is administered to the subject once a month. In another embodiment, the double stranded RNAi agent is administered to the subject once every six weeks. In one embodiment, the double stranded RNAi agent is administered to the subject once every 2 months. In yet another embodiment, the double stranded RNAi agent is administered to the subject once a quarter.

The double stranded RNAi agent may be administered to the subject as, e.g., a fixed dose of between about 50 mg to about 90 mg, between about 50 mg to about 85 mg, between about 50 mg to about 80 mg, between about 40 mg to about 80 mg, between about 60 mg to about 90 mg, between about 25 mg to about 55 mg, between about 25 mg to about 65 mg, between about 40 mg to about 85 mg, between about 40 mg to about 75 mg, between about 40 mg to about 65 mg, or between about 40 mg to about 55 mg.

In some embodiments, the double stranded RNAi agent may be administered as a fixed dose of about 40 mg, about 45 mg, about 50 mg, about 55 mg, about 60 mg, about 65 mg, about 70 mg, about 75 mg, about 80 mg, about 85 mg, or about 90 mg.

In some embodiments, the double stranded RNAi agent is administered to the subject as a fixed dose of about 40 mg;

or as a fixed dose of about 50 mg; or as a fixed dose of about 80 mg; or as a fixed dose of about 90 mg.

In one embodiment, the double stranded RNAi agent is administered to the subject subcutaneously.

In one embodiment, administration of the dose of the double stranded RNAi agent to the subject lowers Serpinc1 activity in the subject by about 70% to about 95%.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40% in the subject.

In yet another embodiment, administration of the dose of the double stranded RNAi agent to the subject decreases the annual bleed rate (ABR) of the subject by about 80 to about 95% as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the subject is a human.

The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In one embodiment, the double stranded RNAi agent is administered to the subject subcutaneously.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity may be at least 17 nucleotides in length or 19 nucleotides in length.

In one embodiment, the region of complementarity is between 19 and 21 nucleotides in length. In another embodiment, the region of complementarity is between 21 and 23 nucleotides in length.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

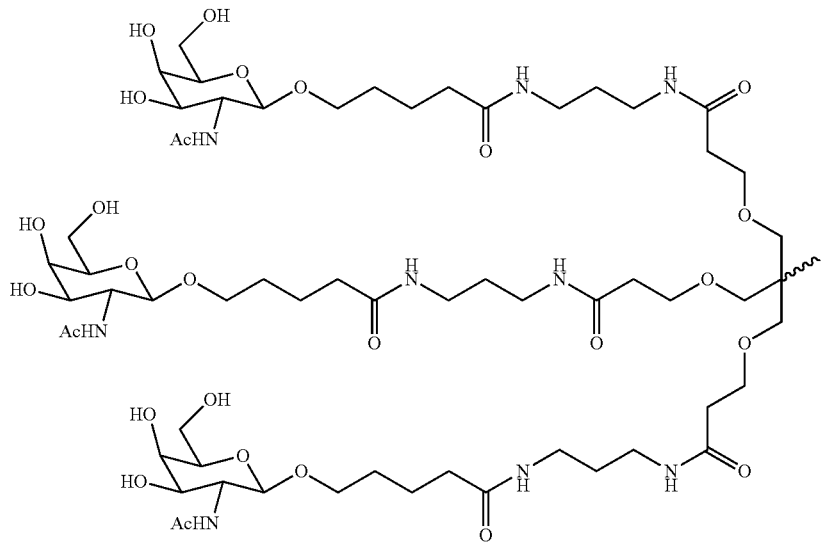

In one embodiment, the RNAi agent is conjugated to the ligand as shown in the following schematic

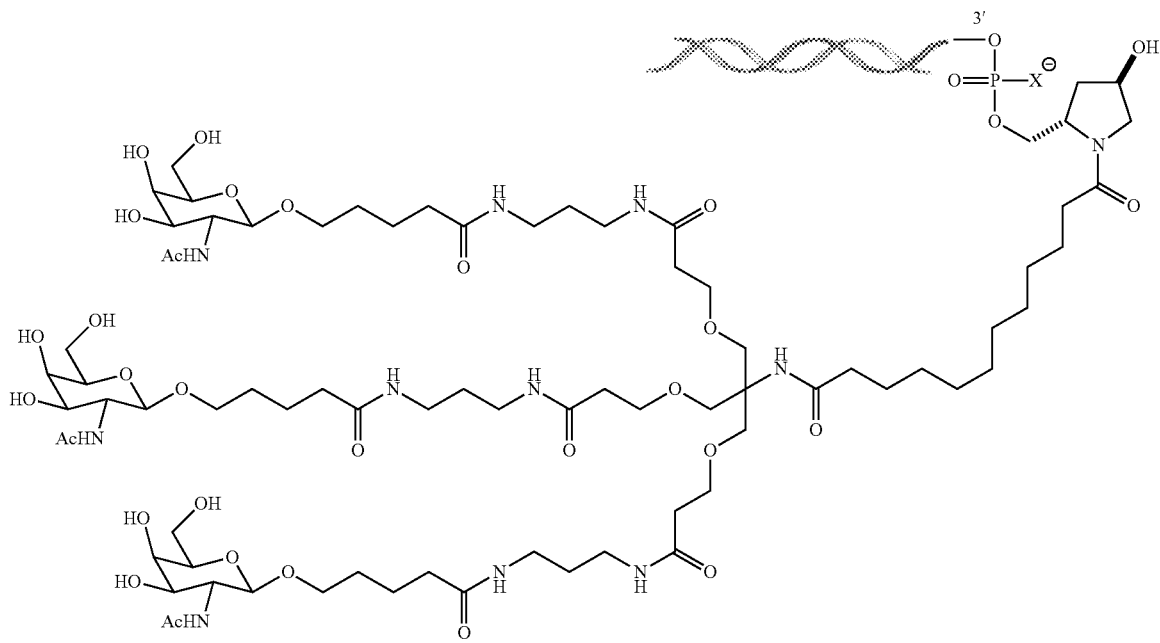

and, wherein X is O or S.

In one embodiment, the X is O.

In one embodiment, the region of complementarity consists of the nucleotide sequence of

```
                                    (SEQ ID NO: 15)
   5'-UUGAAGUAAAUGGUGUUAACCAG-3'.
```

In one embodiment, the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGUGUUAACCAG-3' (SEQ ID NO: 15).

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic

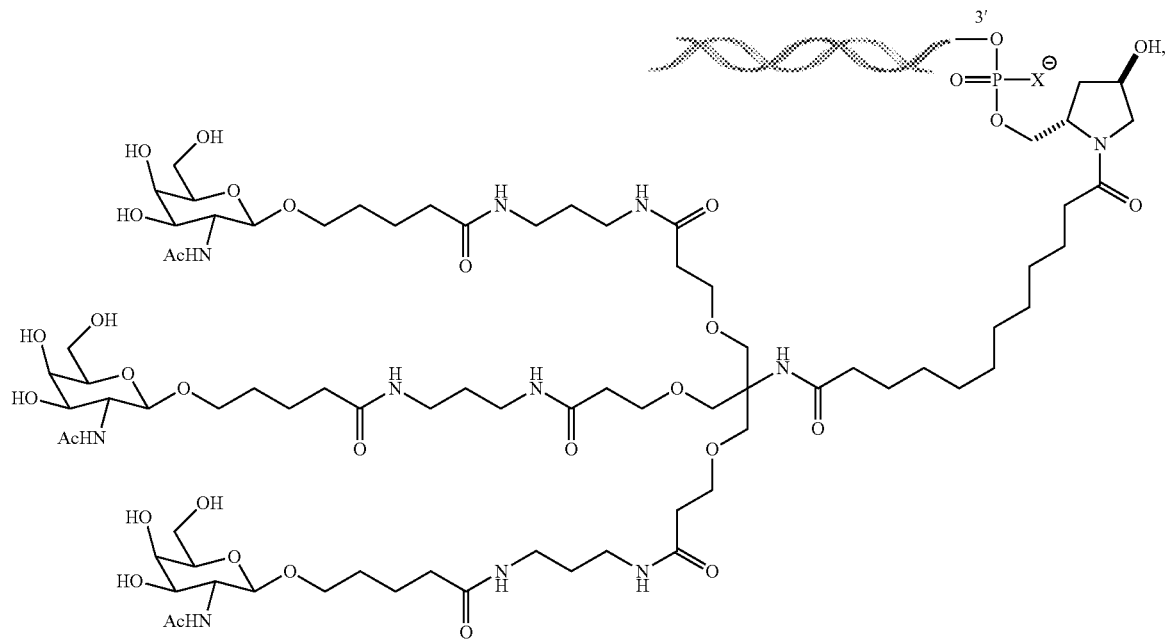

wherein X is O or S.

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

In one aspect, the present invention provides methods of inhibiting expression of Serpinc1 in a subject. The methods include administering to the subject a fixed dose of about 40 mg to about 90 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

In another aspect the present invention provides methods of inhibiting expression of Serpinc1 in a subject. The methods include administering to the subject a fixed dose of about 40 mg to about 90 mg of a double stranded ribonucleic acid (RNAi) agent, wherein the double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the double stranded RNAi agent comprises a ligand, e.g., the sense strand of the double stranded RNAi agent is conjugated to a ligand attached at the 3'-terminus of the sense strand.

The double stranded RNAi agent may be administered to the subject in two or more doses.

In some embodiments, the double stranded RNAi agent is administered to the subject once a month, once every five weeks, once every six weeks, once every seven weeks, once every 2 months, once a quarter, or as needed.

In one embodiment, the double stranded RNAi agent is administered to the subject once a month. In another embodiment, the double stranded RNAi agent is administered to the subject once every six weeks. In one embodiment, the double stranded RNAi agent is administered to the subject once every 2 months. In yet another embodiment, the double stranded RNAi agent is administered to the subject once a quarter.

The double stranded RNAi agent may be administered to the subject as, e.g., a fixed dose of between about 50 mg to about 90 mg, between about 50 mg to about 85 mg, between about 50 mg to about 80 mg, between about 40 mg to about 80 mg, between about 60 mg to about 90 mg, between about 25 mg to about 55 mg, between about 25 mg to about 65 mg, between about 40 mg to about 85 mg, between about 40 mg to about 75 mg, between about 40 mg to about 65 mg, or between about 40 mg to about 55 mg.

In some embodiments, the double stranded RNAi agent may be administered as a fixed dose of about 40 mg, about 45 mg, about 50 mg, about 55 mg, about 60 mg, about 65 mg, about 70 mg, about 75 mg, about 80 mg, about 85 mg, or about 90 mg.

In some embodiments, the double stranded RNAi agent is administered to the subject as a fixed dose of about 40 mg; or as a fixed dose of about 50 mg; or as a fixed dose of about 80 mg; or as a fixed dose of about 90 mg.

In one embodiment, the double stranded RNAi agent is administered to the subject subcutaneously.

In one embodiment, administration of the dose of the double stranded RNAi agent to the subject lowers Serpinc1 activity in the subject by about 70% to about 95%.

In one embodiment, the subject is a human.

In one embodiment, the subject has having a disorder that would benefit from reduction in Serpinc1 expression. The disorder may be a bleeding disorder, such as an acquired bleeding disorder or an inherited bleeding disorder, e.g., a hemophilia, e.g., hemophilia A, hemophilia B, or hemophilia C.

In one embodiment, the subject has hemophilia A and is an inhibitor subject. In another embodiment, the subject has hemophilia B and is an inhibitor subject. In yet another embodiment, the subject has hemophilia C and is an inhibitor subject.

In another embodiment, administration of the dose of the double stranded RNAi agent to the subject increases peak thrombin levels in the subject to within the range of peak thrombin levels in a subject that does not have a disorder that would benefit from reduction in Serpinc1 expression.

In one embodiment, administration of the dose of the double stranded RNAi agent to the subject is sufficient to achieve peak thrombin generation levels in the subject to about the same level achieved by administration to the subject of Factor VIII.

In another embodiment, administration of the dose of the double stranded RNAi agent to the subject is sufficient to achieve peak thrombin generation levels of greater than about 40% in the subject.

In yet another embodiment, administration of the dose of the double stranded RNAi agent to the subject decreases the annual bleed rate (ABR) of the subject by about 80 to about 95% as compared to the median historical on-demand ABR of subjects having a disorder that would benefit from reduction in Serpinc1 expression that are not administered the double stranded RNAi agent.

In one embodiment, double stranded RNAi agent is administered with a buffer solution, such as a buffer solution comprising acetate, citrate, prolamine, carbonate, or phosphate or any combination thereof. In one embodiment, the buffer solution is phosphate buffered saline (PBS).

In one embodiment, the double stranded RNAi agent is administered to the subject subcutaneously.

In one embodiment, all of the nucleotides of the sense strand and all of the nucleotides of the antisense strand are modified nucleotides.

In one embodiment, the modified nucleotides are independently selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity may be at least 17 nucleotides in length or 19 nucleotides in length.

In one embodiment, the region of complementarity is between 19 and 21 nucleotides in length. In another embodiment, the region of complementarity is between 21 and 23 nucleotides in length.

In one embodiment, each strand is no more than 30 nucleotides in length.

At least one strand of the double stranded RNAi agent may comprise a 3' overhang of at least 1 nucleotide or a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

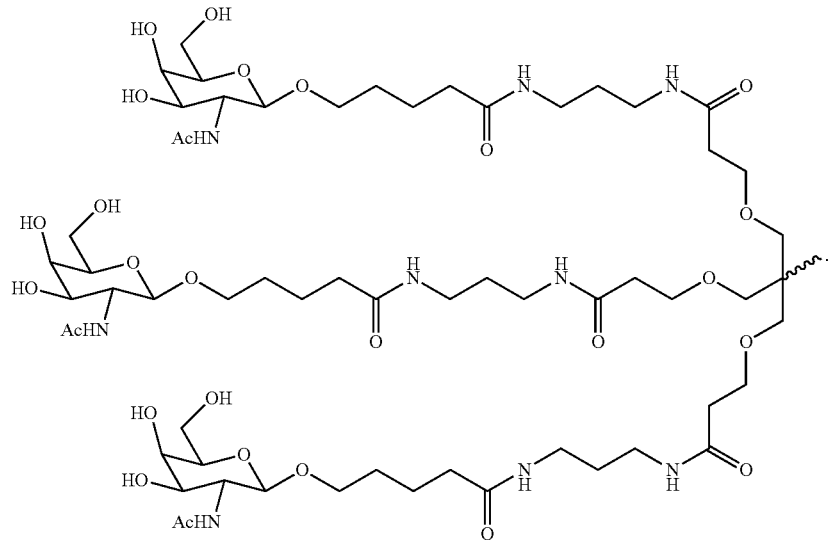 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand as shown in the following schematic

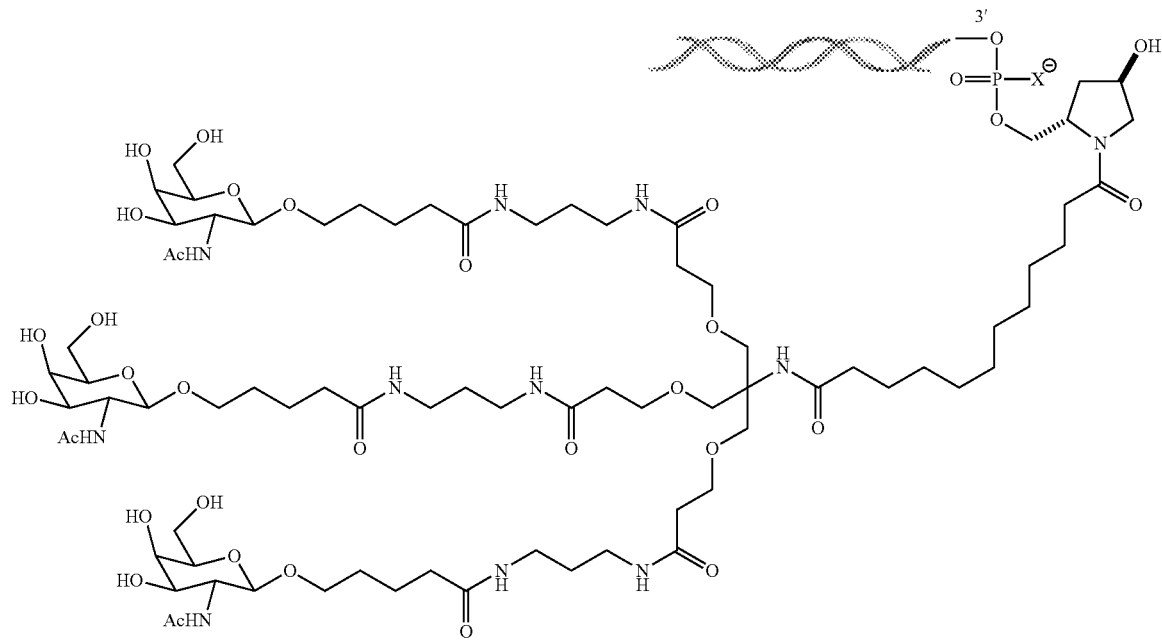

and, wherein X is O or S.

In one embodiment, the X is O.

In one embodiment, the region of complementarity consists of the nucleotide sequence of

5'-UUGAAGUAAAUGGUGUUAACCAG-3'. (SEQ ID NO: 15)

In one embodiment, the double stranded RNAi agent comprises a sense strand comprising the nucleotide sequence of 5'-GGUUAACACCAUUUACUUCAA-3' (SEQ ID NO: 16), and an antisense strand comprising the nucleotide sequence of 5'-UUGAAGUAAAUGGU-GUUAACCAG-3' (SEQ ID NO: 15).

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

In one embodiment, the sense strand comprises 5'-GfsgsUfuAfaCfaCfCfAfuUfuAfcUfuCfaAf-3' (SEQ ID NO:13) and the antisense strand comprises 5'-usUfsgAf-aGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage; and wherein the sense strand is conjugated to the ligand as shown in the following schematic

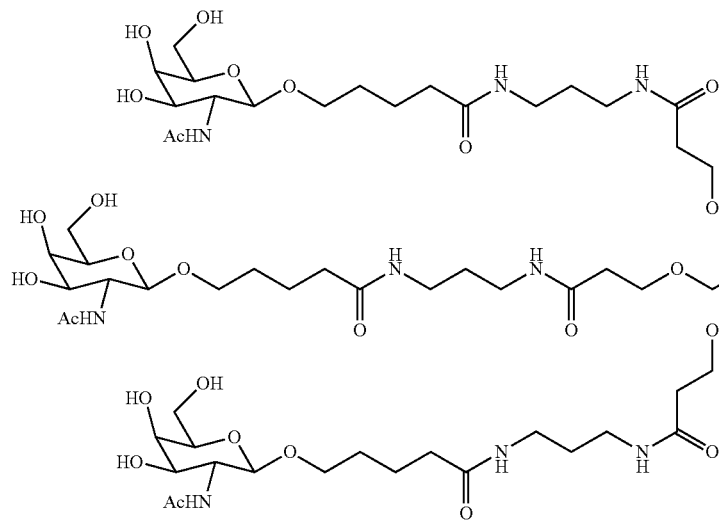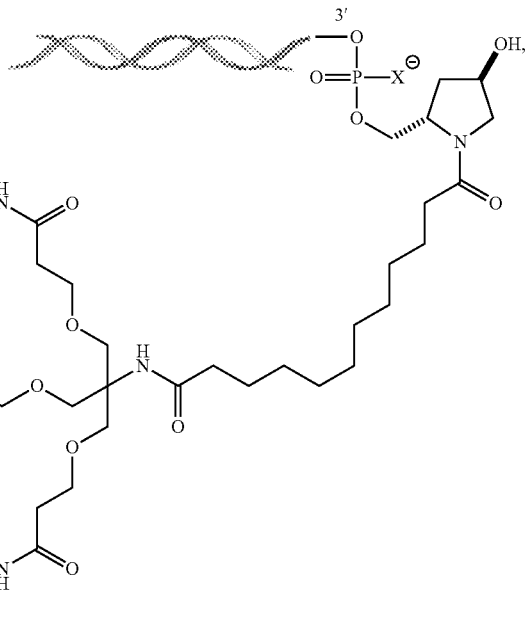

wherein X is O or S.

In one embodiment, the agent is administered as a pharmaceutical composition. In one embodiment, the RNAi agent is administered in an unbuffered solution, such as saline or water.

In another embodiment, the siRNA is administered with a buffer solution, such as a buffer solution comprising acetate, citrate, prolamine, carbonate, or phosphate or any combination thereof. In one embodiment, the buffer solution is phosphate buffered saline (PBS).

In a further aspect, the present invention provides kits for performing the methods of the invention. The kits may include an RNAi agent of the invention, and instructions for use, and optionally, means for administering the RNAi agent to the subject.

BRIEF DESCRIPTION OF THE DRAWINGS

FIG. 12 is a table showing the bleed event data for the subjects enrolled in Part C of the Phase I clinical trial of AD-57213.

FIG. 14A is a graph depicting the relative AT activity in relation to the percent peak thrombin generation achieved with Factor VIII as determined in an inhibitor subject administered a fixed monthly 50 mg dose of AD-57213.

FIG. 14B is a graph depicting the relative AT activity in relation to the percent peak thrombin generation achieved with Factor VIII as determined in an inhibitor subject administered a fixed monthly 50 mg dose of AD-57213.

FIG. 17A is a table showing the bleed event data for the subjects enrolled in Part D of the Phase I clinical trial of AD-57213.

FIG. 20A is a table showing the bleed event data for the subjects enrolled in the Phase II OLE clinical trial of AD-57213.

DETAILED DESCRIPTION OF THE INVENTION

Figure 1B:
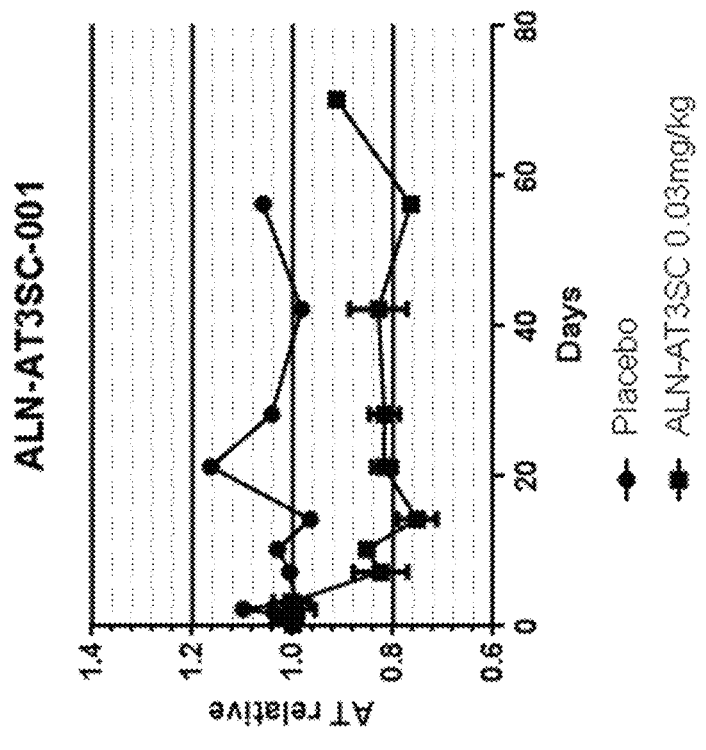
FIG. 1B is a graph depicting the effects of a single subcutaneous 0.03 mg/kg dose of AD-57213 on plasma thrombin generation levels in one healthy human subject.
Figure 1A:
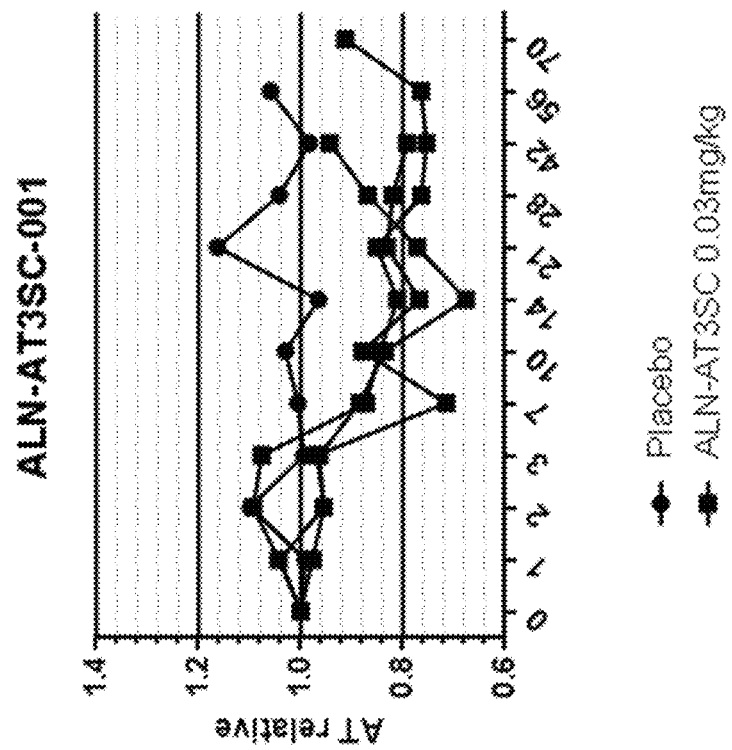
FIG. 1A is a graph depicting the effects of a single subcutaneous 0.03 mg/kg dose of AD-57213 on plasma thrombin generation levels in one healthy human subject.
Figure 1D:
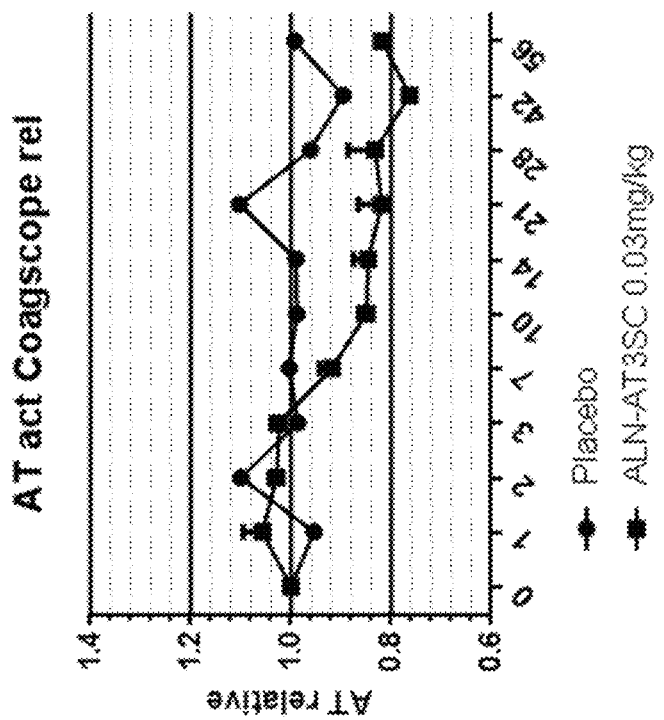
FIG. 1D is a graph depicting the effects of a single subcutaneous 0.03 mg/kg dose of AD-57213 on plasma thrombin generation levels in one healthy human subject.
Figure 1C:
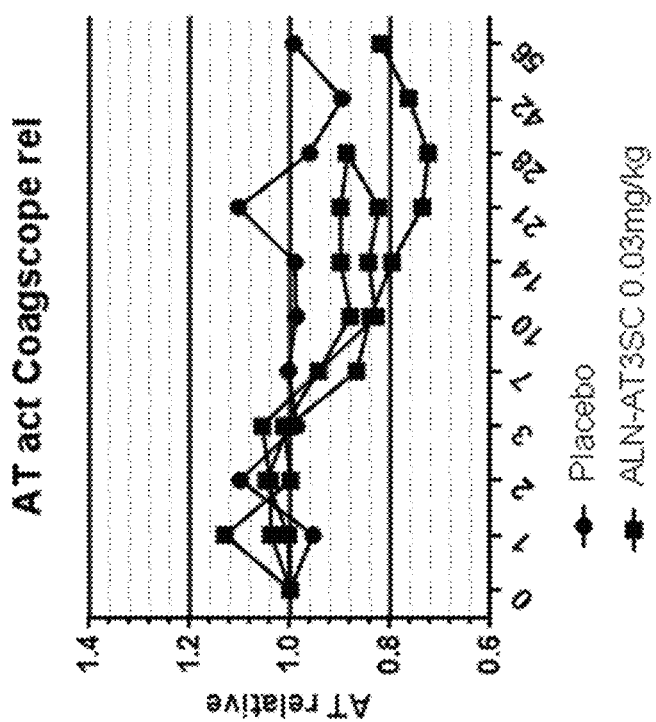
FIG. 1C is a graph depicting the effects of a single subcutaneous 0.03 mg/kg dose of AD-57213 on plasma thrombin generation levels in one healthy human subject.
Figure 2B:
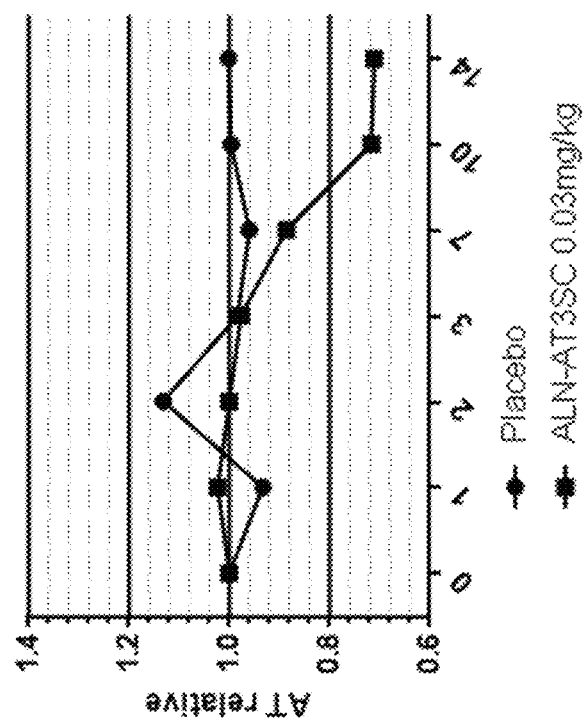
FIG. 2B is a graph depicting the effects of a single subcutaneous 0.03 mg/kg dose of AD-57213 on plasma AT (Serpinc1) protein levels in one healthy human subject.
Figure 2A:
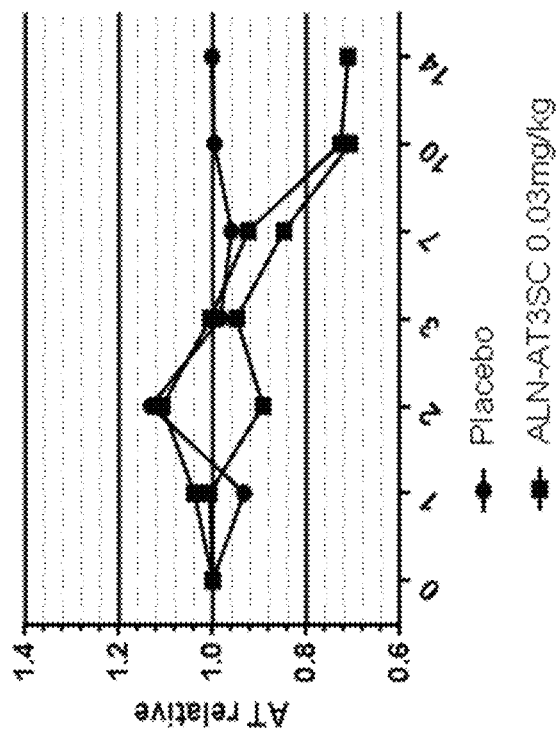
FIG. 2A is a graph depicting the effects of a single subcutaneous 0.03 mg/kg dose of AD-57213 on plasma AT (Serpinc1) protein levels in one healthy human subject.

The present invention is based, at least in part, on the surprising discovery that very low doses (e.g., doses at least about 30 times lower than doses taught in the art) of a GalNAc linked double stranded RNAi agent comprising particular chemical modifications shows an exceptional potency to inhibit expression of Serpinc1, as well as an exceptional duration of inhibition of Serpinc1 expression. Specifically, low doses of RNAi agents including a GalNAc ligand wherein substantially all of the nucleotides are modified nucleotides, such as an RNAi agent including one or more motifs of three identical modifications on three consecutive nucleotides, including one such motif at or near the cleavage site of the agents, six phosphorothioate linkages, and a GalNAc ligand are shown herein to be exceptionally effective and durable in silencing the activity of the Serpinc1 gene.

Accordingly, the present invention provides methods for preventing at least one symptom, e.g., bleeding, in a subject having a disorder that would benefit from inhibiting or reducing the expression of a Serpinc1 gene, e.g., a Serpinc1-associated disease, such as a hemophilia (e.g., hemophilia A, hemophilia B, or Hemophilia C), using iRNA compositions which effect the RNA-induced silencing complex (RISC)-mediated cleavage of RNA transcripts of a Serpinc1 gene. The present invention further provides methods of treating a subject having a disorder that would benefit from inhibiting or reducing the expression of a Serpinc1 gene, e.g., a bleeding disorder, such as hemophilia (e.g., hemophilia A, hemophilia B, or Hemophilia C), using iRNA compositions which effect the RNA-induced silencing complex (RISC)-mediated cleavage of RNA transcripts of a Serpinc1 gene.

The iRNA agents for use in the methods of the invention generally include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an Serpinc1 gene.

In other embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of a Serpinc1 gene. In some embodiments, the sense and antisense strands form a duplex of 18-30 contiguous nucleotides.

In some embodiments, the iRNA agents for use in the methods of the invention include an RNA strand (the antisense strand) which can be up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of a Serpinc1 gene. In some embodiments, such iRNA agents having longer length antisense strands may include a second RNA strand (the sense strand) of 20-60 nucleotides in length wherein the sense and antisense strands form a duplex of 18-30 contiguous nucleotides.

The following detailed description discloses how to make and use compositions containing iRNAs to inhibit the expression of a Serpinc1 gene, as well as compositions, uses, and methods for treating subjects having diseases and disorders that would benefit from inhibition and/or reduction of the expression of this gene.

I. DEFINITIONS

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Serpinc1" refers to a particular polypeptide expressed in a cell. Serpinc1 is also known as serpin peptidase inhibitor, clade C (antithrombin; AT), member 1; antithrombin III; AT3; antithrombin; and heparin cofactor 1. The sequence of a human Serpinc1 mRNA transcript can be found at, for example, GenBank Accession No. GI:254588059 (NM_000488; SEQ ID NO:1). The sequence of rhesus Serpinc1 mRNA can be found at, for example, GenBank Accession No. GI:157167169 (NM_001104583; SEQ ID NO:2). The sequence of mouse Serpinc1 mRNA can be found at, for example, GenBank Accession No. GI:237874216 (NM_080844; SEQ ID NO:3). The sequence of rat Serpinc1 mRNA can be found at, for example, GenBank Accession No. GI:58865629 (NM_001012027; SEQ ID NO:4).

The term "Serpinc1" as used herein also refers to a particular polypeptide expressed in a cell by naturally occurring DNA sequence variations of the Serpinc1 gene, such as a single nucleotide polymorphism in the Serpinc1 gene. Numerous SNPs within the Serpinc1 gene have been identified and may be found at, for example, NCBI dbSNP (see, e.g., www.ncbi.nlm.nih.gov/snp). Non-limiting examples of SNPs within the Serpinc1 gene may be found at, NCBI dbSNP Accession Nos. rs677; rs5877; rs5878; rs5879; rs941988; rs941989; rs1799876; rs19637711; rs2008946; and rs2227586.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In one embodiment, the subject is a human, such as a human being treated or assessed for a disease, disorder or condition that would benefit from reduction in Serpinc1 expression; a human at risk for a disease, disorder or condition that would benefit from reduction in Serpinc1 expression; a human having a disease, disorder or condition that would benefit from reduction in Serpinc1 expression; and/or human being treated for a disease, disorder or condition that would benefit from reduction in Serpinc1 expression as described herein.

As used herein, the terms "treating" or "treatment" refer to a beneficial or desired result including, but not limited to, alleviation or amelioration of one or more symptoms, diminishing the extent of bleeding, stabilized (i.e., not worsening) state of bleeding, amelioration or palliation of the bleeding, whether detectable or undetectable. "Treatment" can also mean prolonging survival as compared to expected survival in the absence of treatment. In the methods of the invention, treatment includes on demand treatment and control of bleeding episodes, perioperative management of bleeding and routine prophylaxis to reduce the frequency of bleeding episodes.

The term "lower" in the context of the level of a Serpinc1 in a subject or a disease marker or symptom refers to a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more and is preferably down to a level accepted as within the range of normal for an individual without such disorder.

As used herein, "prevention" or "preventing," when used in reference to a disease, disorder or condition thereof, that would benefit from a reduction in expression of a Sertpinc1 gene, refers to a reduction in the likelihood that a subject will develop a symptom associated with a such a disease, disorder, or condition, e.g., a symptom such as a bleed. The likelihood of developing a bleed is reduced, for example, when an individual having one or more risk factors for a bleed either fails to develop a bleed or develops a bleed with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "bleeding disorder" is a disease or disorder that results in poor blood clotting and/or excessive bleeding. A bleeding disorder may be an inherited disorder, such as a hemophilia or von Willebrand's disease, or an acquired disorder, associated with, for example, disseminated intravascular coagulation, pregnancy-associated eclampsia, vitamin K deficiency, an autoimmune disorder, inflammatory bowel disease, ulcerative colitis, a dermatologic disorder (e.g., psoriasis, pemphigus), a respiratory disease (e.g., asthma, chronic obstructive pulmonary disease), an allergic drug reaction, e.g., the result of medications, such as aspirin, heparin, and warfarin, diabetes, acute hepatitis B infection, acute hepatitis C infection, a malignancy or solid tumor (e.g., prostate, lung, colon, pancreas, stomach, bile duct, head and neck, cervix, breast, melanoma, kidney, and/or a hematologic malignancy). In one embodiment, an inherited bleeding disorder is a hemophilia, e.g., hemophilia A, B, or C. In one embodiment, a subject having an inherited bleeding disorder, e.g., a hemophilia, has developed inhibitors, e.g., alloantibody inhibitors, to replacement coagulation therapies and is referred to herein as an "inhibitor subject." In one embodiment, the inhibitor subject has hemophilia A. In another embodiment, the inhibitor subject has hemophilia B. In yet another embodiment, the inhibitor subject has hemophilia C.

"Therapeutically effective amount," as used herein, is intended to include the amount of an RNAi agent that, when administered to a subject having a bleeding disorder and bleeding, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a bleeding disorder but not bleeding, e.g., a subject having a bleeding disorder and scheduled for surgery (e.g., perioperative treatment), is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

As used herein, "target sequence" refers to a contiguous portion of the nucleotide sequence of an mRNA molecule formed during the transcription of a Serpinc1 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a Serpinc1 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Serpinc1 in a cell, e.g., a cell within a subject, such as a mammalian subject.

In one embodiment, an RNAi agent of the invention includes a single stranded RNA that interacts with a target RNA sequence, e.g., a Serpinc1 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a Serpinc1 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, an "iRNA" for use in the compositions, uses, and methods of the invention is a double stranded RNA and is referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a Serpinc1 gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides.

As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA of 24-30 nucleotides that interacts with a target RNA sequence, e.g., a Serpinc1 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 10-30 nucleotides, 10-25 nucleotides, 10-20 nucleotides or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3' end of the antisense strand of the duplex. In certain embodiments, an extended overhang is present on the 5' end of the antisense strand of the duplex. In certain embodiments, one or more of the nucleotides in the extended overhang is replaced with a nucleoside thiophosphate.

"Blunt" or "blunt end" means that there are no unpaired nucleotides at that end of the double stranded RNAi agent, i.e., no nucleotide overhang. A "blunt ended" RNAi agent is a dsRNA that is double stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a Serpinc1 mRNA. As used herein, the term "region of complementarity" refers to the region on the antisense strand that is substantially complementary to a sequence, for example a target sequence, e.g., a Serpinc1 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., 5 0 37 Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Serpinc1). For example, a polynucleotide is complementary to at least a part of a Serpinc1 mRNA if the sequence is substantially complementary to a non-interrupted portion of an mRNA encoding Serpinc1.

Accordingly, in some embodiments, the antisense strand polynucleotides disclosed herein are fully complementary to the target Serpinc1 sequence. In other embodiments, the antisense strand polynucleotides disclosed herein are substantially complementary to the target Serpinc1 sequence and comprise a contiguous nucleotide sequence which is at least about 80% complementary over its entire length to the equivalent region of the nucleotide sequence of SEQ ID NO:1, or a fragment of SEQ ID NO:1, such as about 85%, about 86%, about 87%, about 88%, about 89%, about 90%, about % 91%, about 92%, about 93%, about 94%, about 95%, about 96%, about 97%, about 98%, or about 99% complementary.

In one embodiment, an RNAi agent of the invention includes a sense strand that is substantially complementary to an antisense polynucleotide which, in turn, is complementary to a target Serpinc1 sequence, and wherein the sense strand polynucleotide comprises a contiguous nucleotide sequence which is at least about 80% complementary over its entire length to the equivalent region of the nucleotide sequence of SEQ ID NO:5, or a fragment of any one of SEQ ID NO:5, such as about 85%, about 86%, about 87%, about 88%, about 89%, about 90%, about % 91%, about 92%, about 93%, about 94%, about 95%, about 96%, about 97%, about 98%, or about 99% complementary.

In one aspect of the invention, an agent for use in the methods and compositions of the invention is a single-stranded antisense RNA molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

The term "inhibiting," as used herein, is used interchangeably with "reducing," "silencing," "downregulating," "suppressing" and other similar terms, and includes any level of inhibition.

The phrase "inhibiting expression of a Serpinc1," as used herein, includes inhibition of expression of any Serpinc1 gene (such as, e.g., a mouse Serpinc1 gene, a rat Serpinc1 gene, a monkey Serpinc1 gene, or a human Serpinc1 gene) as well as variants or mutants of a Serpinc1 gene that encode a Serpinc1 protein.

"Inhibiting expression of a Serpinc1 gene" includes any level of inhibition of a Serpinc1 gene, e.g., at least partial suppression of the expression of a Serpinc1 gene, such as an inhibition by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a Serpinc1 gene may be assessed based on the level of any variable associated with Serpinc1 gene expression, e.g., Serpinc1 mRNA level, Serpinc1 protein level, or, for example, thrombin:antithrombin complex levels as a measure of thrombin generation potential, bleeding time, prothrombin time (PT), platelet count, and/or activated partial thromboplastin time (aPTT). Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of a Serpinc1 gene, is assessed by a reduction of the amount of Serpinc1 mRNA which can be isolated from or detected in a first cell or group of cells in which a Serpinc1 gene is transcribed and which has or have been treated such that the expression of a Serpinc1 gene is inhibited, as compared to a second cell or group of cells substantially identical to the first cell or group of cells but which has or have not been so treated (control cells). The degree of inhibition may be expressed in terms of $$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

II. METHODS OF THE INVENTION

The present invention provides therapeutic and prophylactic methods which include administering to a subject having a Serpinc1-associated disease, e.g., a bleeding disorder, e.g., a hemophilia (e.g., hemophilia A, hemophilia B, or hemophilia C), an iRNA agent or a pharmaceutical composition comprising an iRNA agent of the invention. In some aspects of the invention, the methods further include administering to the subject an additional therapeutic agent.

In certain embodiments of the invention, for example, when a double stranded RNAi agent includes one or more motifs of three identical modifications on three consecutive nucleotides, including one such motif at or near the cleavage site of the agent, six phosphorothioate linkages, and a GalNAc ligand, such an agent is administered at a dose of about 0.200 to about 1.825 mg/kg, 0.200 to about 1.800 mg/kg, about 0.200 to about 1.700 mg/kg, about 0.200 to about 1.600 mg/kg, about 0.200 to about 1.500 mg/kg, about 0.200 to about 1.400 mg/kg, about 0.200 to about 1.400 mg/kg, about 0.200 to about 1.200 mg/kg, about 0.200 to about 1.100 mg/kg, about 0.200 to about 1.000 mg/kg, about 0.200 to about 0.900 mg/kg, about 0.200 to about 0.800 mg/kg, about 0.200 to about 0.700 mg/kg, about 0.200 to about 0.600 mg/kg, about 0.200 to about 0.500 mg/kg, about 0.200 to about 0.400 mg/kg, about 0.225 to about 1.825 mg/kg, about 0.225 to about 1.800 mg/kg, about 0.225 to about 1.700 mg/kg, about 0.225 to about 1.600 mg/kg, about 0.225 to about 1.500 mg/kg, about 0.225 to about 1.400 mg/kg, about 0.225 to about 1.400 mg/kg, about 0.225 to about 1.200 mg/kg, about 0.225 to about 1.100 mg/kg, about 0.225 to about 1.000 mg/kg, about 0.225 to about 0.900 mg/kg, about 0.225 to about 0.800 mg/kg, about 0.225 to about 0.700 mg/kg, about 0.225 to about 0.600 mg/kg, about 0.225 to about 0.500 mg/kg, about 0.225 to about 0.400 mg/kg, about 0.250 to about 1.825 mg/kg, about 0.250 to about 1.800 mg/kg, about 0.250 to about 1.700 mg/kg, about 0.250 to about 1.600 mg/kg, about 0.250 to about 1.500 mg/kg, about 0.250 to about 1.400 mg/kg, about 0.250 to about 1.400 mg/kg, about 0.250 to about 1.200 mg/kg, about 0.250 to about 1.100 mg/kg, about 0.250 to about 1.000 mg/kg, about 0.250 to about 0.900 mg/kg, about 0.250 to about 0.800 mg/kg, about 0.250 to about 0.700 mg/kg, about 0.250 to about 0.600 mg/kg, about 0.250 to about 0.500 mg/kg, about 0.250 to about 0.400 mg/kg, about 0.425 to about 1.825 mg/kg, about 0.425 to about 1.800 mg/kg, about 0.425 to about 1.700 mg/kg, about 0.425 to about 1.600 mg/kg, about 0.425 to about 1.500 mg/kg, about 0.425 to about 1.400 mg/kg, about 0.425 to about 1.400 mg/kg, about 0.425 to about 1.200 mg/kg, about 0.425 to about 1.100 mg/kg, about 0.425 to about 1.000 mg/kg, about 0.425 to about 0.900 mg/kg, about 0.425 to about 0.800 mg/kg, about 0.425 to about 0.700 mg/kg, about 0.425 to about 0.600 mg/kg, about 0.425 to about 0.500 mg/kg, about 0.450 to about 1.825 mg/kg, about 0.450 to about 1.800 mg/kg, about 0.450 to about 1.700 mg/kg, about 0.450 to about 1.600 mg/kg, about 0.450 to about 1.500 mg/kg, about 0.450 to about 1.400 mg/kg, about 0.450 to about 1.400 mg/kg, about 0.450 to about 1.200 mg/kg, about 0.450 to about 1.100 mg/kg, about 0.450 to about 1.000 mg/kg, about 0.450 to about 0.900 mg/kg, about 0.450 to about 0.800 mg/kg, about 0.450 to about 0.700 mg/kg, about 0.450 to about 0.600 mg/kg, about 0.450 to about 0.500 mg/kg, about 0.475 to about 1.825 mg/kg, about 0.475 to about 1.800 mg/kg, about 0.475 to about 1.700 mg/kg, about 0.475 to about 1.600 mg/kg, about 0.475 to about 1.500 mg/kg, about 0.475 to about 1.400 mg/kg, about 0.475 to about 1.400 mg/kg, about 0.475 to about 1.200 mg/kg, about 0.475 to about 1.100 mg/kg, about 0.475 to about 1.000 mg/kg, about 0.475 to about 0.900 mg/kg, about 0.475 to about 0.800 mg/kg, about 0.475 to about 0.700 mg/kg, about 0.475 to about 0.600 mg/kg, about 0.475 to about 0.500 mg/kg, about 0.875 to about 1.825 mg/kg, about 0.875 to about 1.800 mg/kg, about 0.875 to about 1.700 mg/kg, about 0.875 to about 1.600 mg/kg, about 0.875 to about 1.500 mg/kg, about 0.875 to about 1.400 mg/kg, about 0.875 to about 1.400 mg/kg, about 0.875 to about 1.200 mg/kg, about 0.875 to about 1.100 mg/kg, about 0.875 to about 1.000 mg/kg, about 0.875 to about 0.900 mg/kg, about 0.900 to about 1.825 mg/kg, about 0.900 to about 1.800 mg/kg, about 0.900 to about 1.700 mg/kg, about 0.900 to about 1.600 mg/kg, about 0.900 to about 1.500 mg/kg, about 0.900 to about 1.400 mg/kg, about 0.900 to about 1.400 mg/kg, about 0.900 to about 1.200 mg/kg, about 0.900 to about 1.100 mg/kg, about 0.900 to about 1.000 mg/kg, about 0.925 to about 1.825 mg/kg, about 0.925 to about 1.800 mg/kg, about 0.925 to about 1.700 mg/kg, about 0.925 to about 1.600 mg/kg, about 0.925 to about 1.500 mg/kg, about 0.925 to about 1.400 mg/kg, about 0.925 to about 1.400 mg/kg, about 0.925 to about 1.200 mg/kg, about 0.925 to about 1.100 mg/kg, or about 0.925 to about 1.000 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, about 0.5 mg/kg, 0.525 mg/kg, 0.55 mg/kg, 0.575 mg/kg, about 0.6 mg/kg, 0.625 mg/kg, 0.65 mg/kg, 0.675 mg/kg, about 0.7 mg/kg, 0.725 mg/kg, 0.75 mg/kg, 0.775 mg/kg, about 0.8 mg/kg, 0.925 mg/kg, 0.95 mg/kg, 0.975 mg/kg, about 1.0 mg/kg, 1.025 mg/kg, 1.05 mg/kg, 1.075 mg/kg, about 1.1 mg/kg, 1.125 mg/kg, 1.15 mg/kg, 1.175 mg/kg, about 1.2 mg/kg, 1.225 mg/kg, 1.25 mg/kg, 1.275 mg/kg, about 1.3 mg/kg, 1.325 mg/kg, 1.35 mg/kg, 1.375 mg/kg, about 1.4 mg/kg, 1.425 mg/kg, 1.45 mg/kg, 1.475 mg/kg, about 1.5 mg/kg, 1.525 mg/kg, 1.55 mg/kg, 1.575 mg/kg, about 1.6 mg/kg, 1.625 mg/kg, 1.65 mg/kg, 1.675 mg/kg, about 1.7 mg/kg, 1.725 mg/kg, 1.75 mg/kg, 1.775 mg/kg, or about 1.8 mg/kg. Values intermediate to the foregoing recited values are also intended to be part of this invention.

Accordingly, in one aspect, the invention provides methods of preventing at least one symptom in a subject having a disorder that would benefit from reduction in Serpinc1 expression, e.g., a bleeding disorder, e.g., a hemophilia. The methods include administering to the subject a prophylactically effective dose, e.g., a dose of about 0.200 mg/kg to about 1.825 mg/kg, of the iRNA agent, e.g., dsRNA, of the invention, (e.g., a pharmaceutical composition comprising a dsRNA of the invention), thereby preventing at least one symptom in the subject having a disorder that would benefit from reduction in Serpinc1 expression.

In another aspect, the present invention provides methods of treating a subject having a disorder that would benefit from reduction in Serpinc1 expression, e.g., a bleeding disorder, e.g., a hemophilia, which include administering to the subject, e.g., a human, a therapeutically effective dose, e.g., a dose of about 0.200 mg/kg to about 1.800 mg/kg, of an iRNA agent targeting a Serpinc1 gene or a pharmaceutical composition comprising an iRNA agent targeting a Serpinc1 gene, thereby treating the subject having a disorder that would benefit from reduction in Serpinc1 expression.

In another aspect, the invention provides uses of a prophylactically effective dose, e.g., a dose of about 0.200 mg/kg to about 1.825 mg/kg, of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia.

In a further aspect, the present invention provides uses of a prophylactically effective dose, e.g., a dose of about 0.200 mg/kg to about 1.825 mg/kg of an iRNA agent of the invention in the manufacture of a medicament for preventing at least one symptom in a subject suffering from a disorder that would benefit from a reduction and/or inhibition of Serpinc1 expression, such as a bleeding disorder, e.g., a hemophilia.

In another aspect, the present invention provides uses of a therapeutically effective dose, e.g., a dose of about 0.200 mg/kg to about 1.825 mg/kg, of an iRNA agent of the invention for treating a subject, e.g., a subject that would benefit from a reduction and/or inhibition of Serpinc1 expression.

In yet another aspect, the present invention provides use of an iRNA agent, e.g., a dsRNA, of the invention targeting a Serpinc1 gene or a pharmaceutical composition comprising a therapeutically effective dose, e.g., a dose of about 0.200 mg/kg to about 1.825 mg/kg, of an iRNA agent targeting a Serpinc1 gene in the manufacture of a medicament for treating a subject, e.g., a subject that would benefit from a reduction and/or inhibition of Serpinc1 expression, such as a subject having a bleeding disorder, e.g., a hemophilia.

In some embodiments of the invention, for example, when a double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, such an agent is administered at a dose of about 0.200 to about 1.825 mg/kg, e.g., as a dose of about 0.200 mg/kg to about 0.250 mg/kg; or as a dose of about 0.425 mg/kg to about 0.475 mg/kg; or as a dose of about 0.875 mg/kg to about 0.925 mg/kg; or as a dose of about 1.775 mg/kg to about 1.825 mg/kg.

Accordingly, in one aspect, the invention provides methods of preventing at least one symptom in a subject having a disorder that would benefit from reduction in Serpinc1 expression, e.g., a bleeding disorder, e.g., a hemophilia. The methods include administering to the subject a prophylactically effective dose, e.g., a dose of about 0.200 mg/kg to about 1.825 mg/kg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus (e.g., a pharmaceutical composition comprising the RNAi agent), thereby preventing at least one symptom in the subject having a disorder that would benefit from reduction in Serpinc1 expression.

In another aspect, the present invention provides methods of treating a subject having a disorder that would benefit from reduction in Serpinc1 expression, e.g., a bleeding disorder, e.g., a hemophilia, which include administering to the subject, e.g., a human, a therapeutically effective dose, e.g., a dose of about 0.200 mg/kg to about 1.825 mg/kg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus or a pharmaceutical composition comprising the iRNA agent targeting a Serpinc1 gene, thereby treating the subject having a disorder that would benefit from reduction in Serpinc1 expression.

In another aspect, the invention provides uses of a prophylactically effective dose, e.g., a dose of about 0.200 mg/kg to about 1.825 mg/kg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus for preventing at least one symptom in a subject suffering from a disorder that would benefit from a reduction and/or inhibition of Serpinc1 expression, such as a bleeding disorder, e.g., a hemophilia.

In a further aspect, the present invention provides uses of a prophylactically effective dose, e.g., a dose of about 0.200 mg/kg to about 1.825 mg/kg of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus in the manufacture of a medicament for preventing at least one symptom in a subject suffering from a disorder that would benefit from a reduction and/or inhibition of Serpinc1 expression, such as a bleeding disorder, e.g., a hemophilia.

In another aspect, the present invention provides uses of a therapeutically effective dose, e.g., a dose of about 0.200 mg/kg to about 1.825 mg/kg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus for treating a subject, e.g., a subject that would benefit from a reduction and/or inhibition of Serpinc1 expression.

In yet another aspect, the present invention provides use of an iRNA agent, e.g., a dsRNA, of the invention targeting a Serpinc1 gene or a pharmaceutical composition comprising a therapeutically effective dose, e.g., a dose of about 0.200 mg/kg to about 1.825 mg/kg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus in the manufacture of a medicament for treating a subject, e.g., a subject that would benefit from a reduction and/or inhibition of Serpinc1 expression, such as a subject having a bleeding disorder, e.g., a hemophilia.

In some embodiments, an iRNA agent of the invention is administered to a subject as a fixed dose. A "fixed dose" (e.g., a dose in mg) means that one dose of an iRNA agent is used for all subjects regardless of any specific subject-related factors, such as weight. In one particular embodiment, a fixed dose of an iRNA agent of the invention is based on a predetermined weight or age.

In some embodiments, the RNAi agent is administered as a fixed dose of between about 25 mg to about 100 mg, e.g., between about 25 mg to about 95 mg, between about 25 mg to about 90 mg, between about 25 mg to about 85 mg, between about 25 mg to about 80 mg, between about 25 mg to about 75 mg, between about 25 mg to about 70 mg, between about 25 mg to about 65 mg, between about 25 mg to about 60 mg, between about 25 mg to about 50 mg, between about 50 mg to about 100 mg, between about 50 mg to about 95 mg, between about 50 mg to about 90 mg, between about 50 mg to about 85 mg, between about 50 mg to about 80 mg, between about 30 mg to about 100 mg, between about 30 mg to about 90 mg, between about 30 mg to about 80 mg, between about 40 mg to about 100 mg, between about 40 mg to about 90 mg, between about 40 mg to about 80 mg, between about 60 mg to about 100 mg, between about 60 mg to about 90 mg, between about 25 mg to about 55 mg, between about 25 mg to about 65 mg, between about 30 mg to about 95 mg, between about 30 mg to about 85 mg, between about 30 mg to about 75 mg, between about 30 mg to about 65 mg, between about 30 mg to about 55 mg, between about 40 mg to about 95 mg, between about 40 mg to about 85 mg, between about 40 mg to about 75 mg, between about 40 mg to about 65 mg, between about 40 mg to about 55 mg, or between about 45 mg to about 95 mg.

In some embodiments, the RNAi agent is administered as a fixed dose of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

Accordingly, in one aspect, the invention provides methods of preventing at least one symptom in a subject having a disorder that would benefit from reduction in Serpinc1 expression, e.g., a bleeding disorder, e.g., a hemophilia. The methods include administering to the subject a prophylactically effective dose, e.g., a fixed dose of about 25 mg to about 100 mg, of the iRNA agent, e.g., dsRNA, of the invention, (e.g., a pharmaceutical composition comprising a dsRNA of the invention), thereby preventing at least one symptom in the subject having a disorder that would benefit from reduction in Serpinc1 expression. In one embodiment, the methods include administering to the subject a prophylactically effective dose, e.g., a fixed dose of about 50 mg, of the iRNA agent, e.g., dsRNA, of the invention, (e.g., a pharmaceutical composition comprising a dsRNA of the invention), thereby preventing at least one symptom in the subject having a disorder that would benefit from reduction in Serpinc1 expression. In another embodiment, the methods include administering to the subject a prophylactically effective dose, e.g., a fixed dose of about 80 mg, of the iRNA agent, e.g., dsRNA, of the invention, (e.g., a pharmaceutical composition comprising a dsRNA of the invention), thereby preventing at least one symptom in the subject having a disorder that would benefit from reduction in Serpinc1 expression.

In another aspect, the present invention provides methods of treating a subject having a disorder that would benefit from reduction in Serpinc1 expression, e.g., a bleeding disorder, e.g., a hemophilia, which include administering to the subject, e.g., a human, a therapeutically effective dose, e.g., a fixed dose of about 25 mg to about 100 mg, of an iRNA agent targeting a Serpinc1 gene or a pharmaceutical composition comprising an iRNA agent targeting a Serpinc1 gene, thereby treating the subject having a disorder that would benefit from reduction in Serpinc1 expression. In one embodiment, the methods include administering to the subject a therapeutically effective dose, e.g., a fixed dose of about 50 mg, of the iRNA agent, e.g., dsRNA, of the invention, (e.g., a pharmaceutical composition comprising a dsRNA of the invention), thereby treating the subject having a disorder that would benefit from reduction in Serpinc1 expression. In another embodiment, the methods include administering to the subject a therapeutically effective dose, e.g., a fixed dose of about 80 mg, of the iRNA agent, e.g., dsRNA, of the invention, (e.g., a pharmaceutical composition comprising a dsRNA of the invention), thereby treating the subject having a disorder that would benefit from reduction in Serpinc1 expression.

In another aspect, the invention provides uses of a prophylactically effective dose, e.g., a fixed dose of about 25 mg to about 100 mg, of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia. In one embodiment, the invention provides uses of a prophylactically effective dose, e.g., a fixed dose of about 50 mg, of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia. In another embodiment, the invention provides uses of a prophylactically effective dose, e.g., a fixed dose of about 80 mg, of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia.

In a further aspect, the present invention provides uses of a prophylactically effective dose, e.g., a fixed dose of about 25 mg to about 100 mg of an iRNA agent of the invention in the manufacture of a medicament for preventing at least one symptom in a subject suffering from a disorder that would benefit from a reduction and/or inhibition of Serpinc1 expression, such as a bleeding disorder, e.g., a hemophilia. In one embodiment, the present invention provides uses of a prophylactically effective dose, e.g., a fixed dose of about 50 mg of an iRNA agent of the invention in the manufacture of a medicament for preventing at least one symptom in a subject suffering from a disorder that would benefit from a reduction and/or inhibition of Serpinc1 expression, such as a bleeding disorder, e.g., a hemophilia. In another embodiment, the present invention provides uses of a prophylactically effective dose, e.g., a fixed dose of about 80 mg of an iRNA agent of the invention in the manufacture of a medicament for preventing at least one symptom in a subject suffering from a disorder that would benefit from a reduction and/or inhibition of Serpinc1 expression, such as a bleeding disorder, e.g., a hemophilia.

In another aspect, the present invention provides uses of a therapeutically effective dose, e.g., a fixed dose of about 25 mg to about 100 mg, of an iRNA agent of the invention for treating a subject, e.g., a subject that would benefit from a reduction and/or inhibition of Serpinc1 expression. In one embodiment, the present invention provides uses of a therapeutically effective dose, e.g., a fixed dose of about 50 mg, of an iRNA agent of the invention for treating a subject, e.g., a subject that would benefit from a reduction and/or inhibition of Serpinc1 expression. In another embodiment, the present invention provides uses of a therapeutically effective dose, e.g., a fixed dose of about 80 mg, of an iRNA agent of the invention for treating a subject, e.g., a subject that would benefit from a reduction and/or inhibition of Serpinc1 expression.

In yet another aspect, the present invention provides use of an iRNA agent, e.g., a dsRNA, of the invention targeting a Serpinc1 gene or a pharmaceutical composition comprising a therapeutically effective dose, e.g., a fixed dose of about 25 mg to about 100 mg, of an iRNA agent targeting a Serpinc1 gene in the manufacture of a medicament for treating a subject, e.g., a subject that would benefit from a reduction and/or inhibition of Serpinc1 expression, such as a subject having a bleeding disorder, e.g., a hemophilia. In one embodiment, the present invention provides use of an iRNA agent, e.g., a dsRNA, of the invention targeting a Serpinc1 gene or a pharmaceutical composition comprising a therapeutically effective dose, e.g., a fixed dose of about 50 mg, of an iRNA agent targeting a Serpinc1 gene in the manufacture of a medicament for treating a subject, e.g., a subject that would benefit from a reduction and/or inhibition of Serpinc1 expression, such as a subject having a bleeding disorder, e.g., a hemophilia. In another embodiment, the present invention provides use of an iRNA agent, e.g., a dsRNA, of the invention targeting a Serpinc1 gene or a pharmaceutical composition comprising a therapeutically effective dose, e.g., a fixed dose of about 80 mg, of an iRNA agent targeting a Serpinc1 gene in the manufacture of a medicament for treating a subject, e.g., a subject that would benefit from a reduction and/or inhibition of Serpinc1 expression, such as a subject having a bleeding disorder, e.g., a hemophilia.

In some embodiments of the invention, for example, when a double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, such an agent is administered at a fixed dose of about 25 mg to about 100 mg, e.g., as a fixed dose of about 25 mg; or as a fixed dose of about 50 mg; or as a fixed dose of about 80 mg; or as a fixed dose of about 100 mg. In one embodiment, the fixed dose is 50 mg. In another embodiment, the fixed dose is 80 mg.

Accordingly, in one aspect, the invention provides methods of preventing at least one symptom in a subject having a disorder that would benefit from reduction in Serpinc1 expression, e.g., a bleeding disorder, e.g., a hemophilia. The methods include administering to the subject a prophylactically effective dose, e.g., a fixed dose of about 25 mg to about 100 mg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus (e.g., a pharmaceutical composition comprising the RNAi agent), thereby preventing at least one symptom in the subject having a disorder that would benefit from reduction in Serpinc1 expression. In one embodiment, the fixed dose is 50 mg. In another embodiment, the fixed dose is 80 mg.

In another aspect, the present invention provides methods of treating a subject having a disorder that would benefit from reduction in Serpinc1 expression, e.g., a bleeding disorder, e.g., a hemophilia, which include administering to the subject, e.g., a human, a therapeutically effective dose, e.g., a fixed dose of about 25 mg to about 100 mg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGA-AGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus or a pharmaceutical composition comprising the iRNA agent targeting a Serpinc1 gene, thereby treating the subject having a disorder that would benefit from reduction in Serpinc1 expression. In one embodiment, the fixed dose is 50 mg. In another embodiment, the fixed dose is 80 mg.

In another aspect, the invention provides uses of a prophylactically effective dose, e.g., a fixed dose of about 25 mg to about 100 mg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus for preventing at least one symptom in a subject suffering from a disorder that would benefit from a reduction and/or inhibition of Serpinc1 expression, such as a bleeding disorder, e.g., a hemophilia. In one embodiment, the fixed dose is 50 mg. In another embodiment, the fixed dose is 80 mg.

In a further aspect, the present invention provides uses of a prophylactically effective dose, e.g., a fixed dose of about 25 mg to about 100 mg of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus in the manufacture of a medicament for preventing at least one symptom in a subject suffering from a disorder that would benefit from a reduction and/or inhibition of Serpinc1 expression, such as a bleeding disorder, e.g., a hemophilia. In one embodiment, the fixed dose is 50 mg. In another embodiment, the fixed dose is 80 mg.

In another aspect, the present invention provides uses of a therapeutically effective dose, e.g., a fixed dose of about 25 mg to about 100 mg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus for treating a subject, e.g., a subject that would benefit from a reduction and/or inhibition of Serpinc1 expression. In one embodiment, the fixed dose is 50 mg. In another embodiment, the fixed dose is 80 mg.

In yet another aspect, the present invention provides use of an iRNA agent, e.g., a dsRNA, of the invention targeting a Serpinc1 gene or a pharmaceutical composition comprising a therapeutically effective dose, e.g., a fixed dose of about 25 mg to about 100 mg, of a double stranded ribonucleic acid (RNAi) agent, comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus in the manufacture of a medicament for treating a subject, e.g., a subject that would benefit from a reduction and/or inhibition of Serpinc1 expression, such as a subject having a bleeding disorder, e.g., a hemophilia. In one embodiment, the fixed dose is 50 mg. In another embodiment, the fixed dose is 80 mg.

The methods and uses of the invention include administering a composition described herein such that expression of the target Serpinc1 gene is decreased, such as for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80 days. In one embodiment, expression of the target Serpinc1 gene is decreased for an extended duration, e.g., at least about seven days or more, e.g., about one week, two weeks, three weeks, about four weeks, about 5 weeks, about 6 weeks, about 2 months, about a quarter, or longer.

Reduction in gene expression can be assessed by any methods known in the art. For example, a reduction in the expression of Serpinc1 may be determined by determining the mRNA expression level of Serpinc1 using methods routine to one of ordinary skill in the art, e.g., Northern blotting, qRT-PCR, by determining the protein level of Serpinc1 using methods routine to one of ordinary skill in the art, such as Western blotting, immunological techniques, and/or by determining a biological activity of Serpinc1, such as affecting one or more molecules associated with the cellular blood clotting mechanism (or in an in vivo setting, blood clotting itself). In one embodiment, thrombin generation time, clot formation time and/or clotting time are determined to assess Serpinc1 expression using, e.g., ROTEM® Thromboelastometry analysis of whole blood.

Administration of the dsRNA according to the methods and uses of the invention may result in a reduction of the severity, signs, symptoms, and/or markers of such diseases or disorders in a patient with a Serpinc1-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, frequency of bleeds, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a bleeding disorder may be assessed, for example, by periodic monitoring of thrombin:anti-thrombin levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting Serpinc1 or pharmaceutical composition thereof, "effective against" a bleeding disorder indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating bleeding disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an iRNA or iRNA formulation as described herein.

The iRNA (or pharmaceutical compositions comprising the iRNA) may be administered to the subject about once a week, about twice a month, about once every six weeks, about once every 2 months, or once a quarter.

A double stranded iRNA agent may be administered to a subject as one or more doses. For example, a double stranded iRNA agent may be administered to a subject as a monthly dose of about 0.200 mg/kg to about 1.825 mg/kg. Alternatively, a double stranded iRNA agent may be administered to a subject as a fixed dose of about 25 mg to about 100 mg.

In one embodiment, a double stranded RNAi agent comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus is administered is administered to the subject as a monthly dose of about 0.200 mg/kg to about 0.250 mg/kg, e.g., about 0.225 mg/kg.

In another embodiment, a double stranded RNAi agent comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus is administered is administered to the subject as a monthly dose of about 0.425 mg/kg to about 0.475 mg/kg, e.g., about 0.450 mg/kg.

In yet another embodiment, a double stranded RNAi agent comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus is administered is administered to the subject as a monthly dose of about 0.875 mg/kg to about 0.925 mg/kg, e.g., about 0.900 mg/kg.

In one embodiment, a double stranded RNAi agent comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus is administered is administered to the subject as a monthly dose of about 1.775 mg/kg to about 1.825, mg/kg, e.g., about 1.800 mg/kg.

In one embodiment, a double stranded RNAi agent comprising a sense strand and an antisense strand, the antisense strand comprising a region of complementarity which comprises at least 15 contiguous nucleotides differing by no more than 3 nucleotides from the nucleotide sequence of 5'-UUGAAGUAAAUGGUGUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus is administered is administered to the subject as a fixed dose of about 25 to about 100 mg, e.g., about 25 mg, 50 mg, 80 mg, or 100 mg. In one embodiment, the fixed dose is 50 mg. In another embodiment, the fixed dose is 80 mg.

The administration may be repeated, for example, on a regular basis, such as monthly, for one month, two months, three months, four months or longer. After an initial treatment regimen, the treatments can be administered on a less frequent basis. For example, after administration monthly for three months, administration can be repeated once per quarter, for a year or longer.

Accordingly, in some embodiments, the RNAi agent is administered in a dosing regimen that includes a "loading phase" of closely spaced administrations that may be followed by a "maintenance phase", in which the RNAi agent is administered at longer spaced intervals.

A loading dosing schedule and/or maintenance dosing schedule may optionally be repeated for one or more iterations. The number of iterations may depend on the achievement of a desired effect, e.g., the suppression of a Serpinc1 gene, and/or the achievement of a therapeutic or prophylactic effect, e.g., increasing blood clotting, reducing clot formation time, and/or reducing clotting time.

Administration of the iRNA can reduce Serpinc1 levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period.

Before administration of a full dose of the iRNA, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on Serpinc1 expression, a composition according to the invention or a pharmaceutical composition prepared therefrom can enhance the quality of life.

An iRNA of the invention may be administered in "naked" form, or as a "free iRNA." A naked iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of Serpinc1 gene expression are those having a bleeding disorder, e.g., an inherited bleeding disorder or an acquired bleeding disorder as described herein. In one embodiment, a subject having an inherited bleeding disorder has a hemophilia, e.g., hemophilia A, B, or C. In one embodiment, a subject having an inherited bleeding disorder, e.g., a hemophilia, is an inhibitor subject (a subject that has become refractory to replacement coagulation factors). In one embodiment, the inhibitor subject has hemophilia A. In another embodiment, the inhibitor subject has hemophilia B. In yet another embodiment, the inhibitor subject has hemophilia C. Treatment of a subject that would benefit from a reduction and/or inhibition of Serpinc1 gene expression includes therapeutic (e.g., on-demand, e.g., the subject is bleeding (spontaneous bleeding or bleeding as a result of trauma) and failing to clot) and prophylactic (e.g., the subject is not bleeding and/or is to undergo surgery) treatment.

The invention further provides methods and uses for the use of an iRNA or a pharmaceutical composition thereof, e.g., for treating a subject that would benefit from reduction and/or inhibition of Serpinc1 expression, e.g., a subject having a bleeding disorder, in combination with other pharmaceuticals and/or other therapeutic methods, e.g., with known pharmaceuticals and/or known therapeutic methods, such as, for example, those which are currently employed for treating these disorders.

For example, in certain embodiments, an iRNA targeting Serpinc1 is administered in combination with, e.g., an agent useful in treating a bleeding disorder as described elsewhere herein. For example, additional therapeutics and therapeutic methods suitable for treating a subject that would benefit from reduction in Serpinc1 expression, e.g., a subject having a bleeding disorder, include fresh-frozen plasma (FFP); recombinant FVIIa; recombinant FIX; FXI concentrates; virus-inactivated, vWF-containing FVIII concentrates; desensitization therapy which may include large doses of FVIII or FIX, along with steroids or intravenous immunoglobulin (IVIG) and cyclophosphamide; plasmapheresis in conjunction with immunosuppression and infusion of FVIII or FIX, with or without antifibrinolytic therapy; immune tolerance induction (ITI), with or without immunosuppressive therapy (e.g., cyclophosphamide, prednisone, and/or anti-CD20); desmopressin acetate [DDAVP]; antifibrinolytics, such as aminocaproic acid and tranexamic acid; activated prothrombin complex concentrate (PCC); antihemophilic agents; corticosteroids; immunosuppressive agents; and estrogens.

The iRNA and an additional therapeutic agent and/or treatment may be administered at the same time and/or in the same combination, e.g., parenterally, or the additional therapeutic agent can be administered as part of a separate composition or at separate times and/or by another method known in the art or described herein.

In one embodiment, the present invention provides methods for treating a subject suffering from a bleeding disorder, e.g., a hemophilia, by subcutaneously administering to the subject compound AD-57213 (Sense strand: 5'-GfsgsUfuA-faCfaCfCfAfuUfuAfcUfuCfaAf-3' (SEQ ID NO:13) and Antisense stand: 5'-usUfsgAfaGfuAfaAfuggUfgUfuA-faCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage) at a dose of about 0.200 mg/kg to about 1.800 mg/kg, e.g., a monthly dose of about about 0.200 mg/kg to about 0.250 mg/kg; about 0.425 mg/kg to about 0.475 mg/kg; about 0.875 mg/kg to about 0.925 mg/kg; or about 1.775 mg/kg to about 1.825 mg/kg.

In another embodiment, the present invention provides methods for treating a subject suffering from a bleeding disorder, e.g., a hemophilia, by subcutaneously administering to the subject compound AD-57213 (Sense strand: 5'-GfsgsUfuAfaCfaCfCfAfuUfuAfcUfuCfaAf-3' (SEQ ID NO:13) and Antisense stand: 5'-usUfsgAfaGfuAfaAfug-gUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage) at a fixed dose of about 25 mg to about 100 mg, e.g., a fixed dose of about 25 mg, about 50 mg, about 80 mg or about 100 mg. In one embodiment, the fixed dose is 50 mg. In another embodiment, the fixed dose is 80 mg.

III. IRNAS FOR USE IN THE METHODS OF THE INVENTION

Described herein are methods for the use of improved double stranded RNAi agents which inhibit the expression of a Serpinc1 gene in a cell, such as a cell within a subject, e.g., a mammal, such as a human having a Serpinc1-associated disorder, e.g., a bleeding disorder, e.g., hemophilia.

Accordingly, the invention provides double stranded RNAi agents with chemical modifications capable of inhibiting the expression of a target gene (i.e., a Serpinc1 gene) in vivo.

In certain aspects of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The RNAi agent comprises a sense strand and an antisense strand. Each strand of the RNAi agent may range from 12-30 nucleotides in length. For example, each strand may be between 14-30 nucleotides in length, 17-30 nucleotides in length, 19-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

Any of the nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571, 799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$$OCH_3$, O($CH_2$)$_n$—$NH_2$, O($CH_2$)$_n$$CH_3$, O($CH_2$)$_n$—$ONH_2$, and O($CH_2$)$_n$—ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chin. Acta,* 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy (2'-$OCH_3$), 2'-aminopropoxy (2'-$OCH_2CH_2CH_2NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more bicyclic sugar moities. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include the RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-0-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C (CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH (CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

A. Modified iRNAs Comprising Motifs of the Invention

In certain aspects of the invention, the double stranded RNAi agents of the invention include agents with chemical modifications as disclosed, for example, in U.S. Provisional Application No. 61/561,710, filed on Nov. 18, 2011, or in PCT/US2012/065691, filed on Nov. 16, 2012, the entire contents of each of which are incorporated herein by reference.

As shown herein, in Provisional Application No. 61/561,710, and in PCT/US2012/065691, a superior result may be obtained by introducing one or more motifs of three identical modifications on three consecutive nucleotides into a sense strand and/or antisense strand of a RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double stranded RNAi agent are modified to have one or more motifs of three identical modifications on three consecutive nucleotides at or near the cleavage site of at least one strand of an RNAi agent, the gene silencing activity of the RNAi agent was superiorly enhanced.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotides in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking 0 of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking 0 position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAA-BAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisenese strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYYN$_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5' end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. A "mismatch" may be non-canonical base pairing or other than canonical pairing of nucleotides. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings. A "universal base" is a base that exhibits the ability to replace any of the four normal bases (G, C, A, and U) without significantly destabilizing neighboring base-pair interactions or disrupting the expected functional biochemical utility of the modified oligonucleotide. Non-limiting examples of universal bases include 2'-deoxyinosine (hypoxanthine deoxynucleotide) or its derivatives, nitroazole analogues, and hydrophobic aromatic non-hydrogen-bonding bases.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

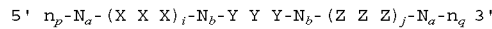

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each $n_p$ and $n_q$ independently represent an overhang nucleotide;
wherein $N_b$ and Y do not have the same modification; and
XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

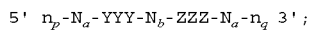

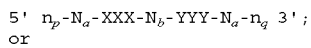

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides. When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

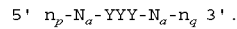

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

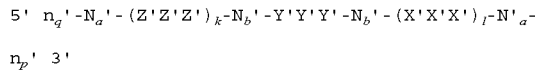

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide;
wherein $N_b'$ and Y' do not have the same modification; and
X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

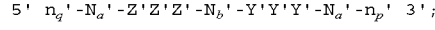

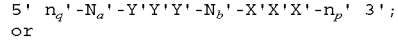

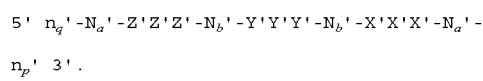

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and 1 is 0 and the antisense strand may be represented by the formula:

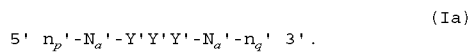
(Ia)

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

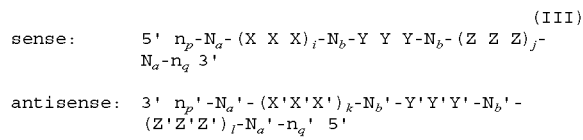
(III)

wherein:
i, j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, $n_p$, $n_q'$, and $n_q$, each of which may or may not be present, independently represents an overhang nucleotide; and
XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

(IIIa)

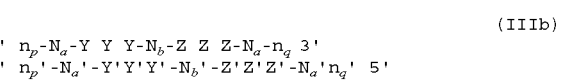
(IIIb)

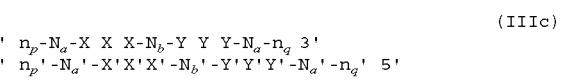
(IIIc)

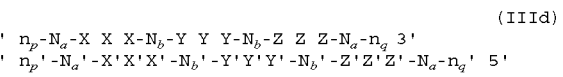
(IIId)

5'-$N_a$-Y Y Y-$N_a$-3'
3' $n_p'$-$N_a'$-Y'Y'Y'-$N_a'$ 5'
(IIIe)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

When the RNAi agent is represented as formula (IIIe), each $N_a$ and $N_a'$ independently represents an oligonucleotide sequence comprising 0-25 nucleotides which are either modified or unmodified or combinations thereof, each sequence comprising at least two differently modified nucleotides.

Each of X, Y and Z in formulas (III), (IIIa), (IIIb), (IIIc), (IIId), and (IIIe) may be the same or different from each other.

When the RNAi agent is represented by formula (III), (IIIa), (IIIb), (IIIc), (IIId), and (IIIe) at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a monovalent, a bivalent or a trivalent branched linker. In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a monovalent, a bivalent or a trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a monovalent, a bivalent or a trivalent branched linker.

In one embodiment, the RNAi agent is a multimer containing at least two duplexes represented by formula (III), (IIIa), (IIIb), (IIIc), (IIId), and (IIIe), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), (IIId), and (IIIe), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), (IIId), and (IIIe) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

The RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is AD-57213 (Sense strand: 5'-GfsgsUfuAfaCfaCfCfAfuUfuAfcUfuCfaAf-3' (SEQ ID NO:13) and Antisense strand: 5'-usUfsgAfaGfuAfaAfuggUfgUfuAfaCfcsasg-3' (SEQ ID NO:14), wherein A, C, G, and U are ribose A, C, G or U; a, c, g, and u are 2'-O-methyl (2'-OMe) A, C, G, or U; Af, Cf, Gf or Uf are 2'-fluoro A, C, G or U; and s is a phosphorothioate linkage.

These agents may further comprise a ligand.

Ligands

The double stranded RNA (dsRNA) agents of the invention may optionally be conjugated to one or more ligands. The ligand can be attached to the sense strand, antisense strand or both strands, at the 3'-end, 5'-end or both ends. For instance, the ligand may be conjugated to the sense strand. In preferred embodiments, the ligand is conjugated to the 3'-end of the sense strand. In one embodiment, the ligand is a carbohydrate conjugate, such as a monosaccharide.

In one embodiment, the ligand is an N-acetylgalactosamine (GalNAc) GalNAc or GalNAc derivative. In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, a carbohydrate conjugate for use in the compositions and methods of the invention is selected from the group consisting of:

Formula II

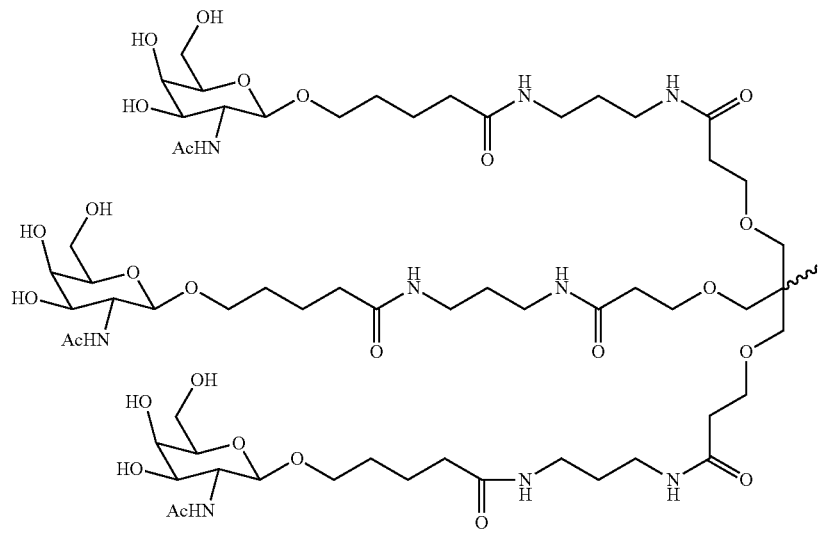

Formula III

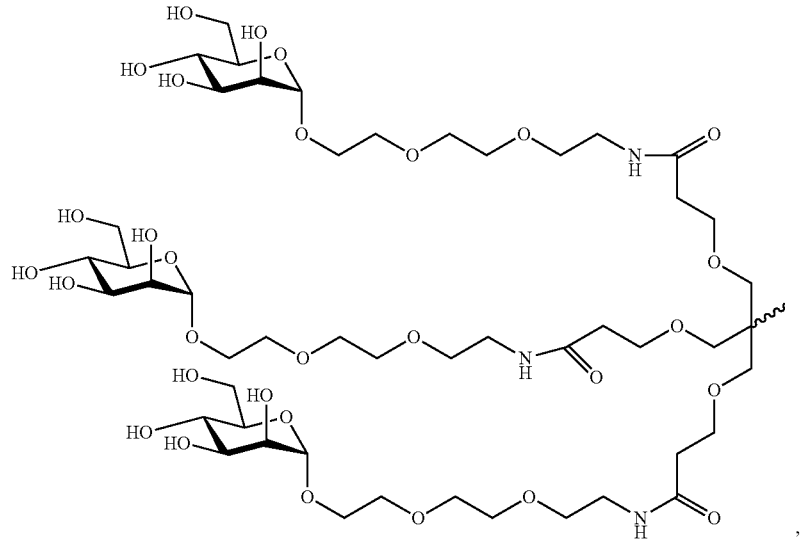

-continued
Formula IV
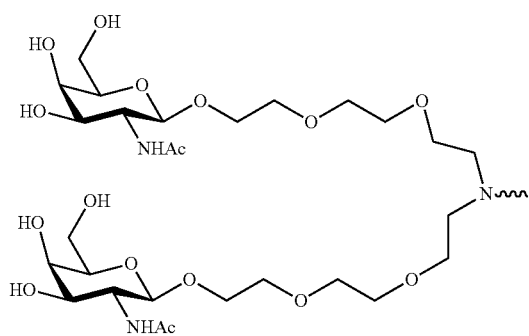
Formula V
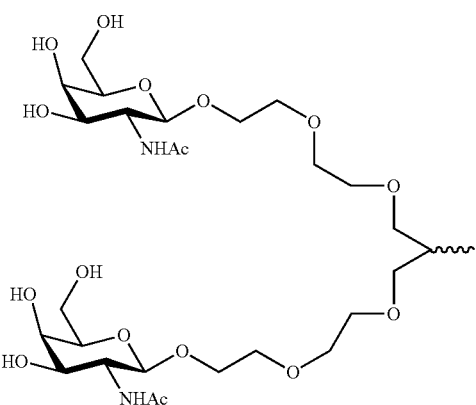
Formula VI
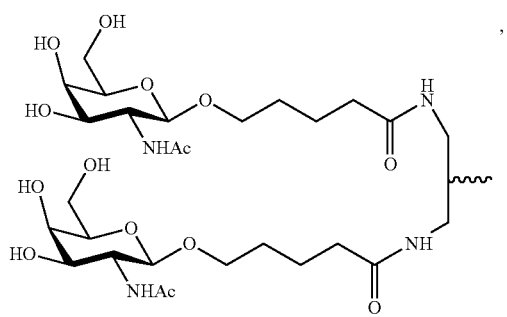
Formula VII
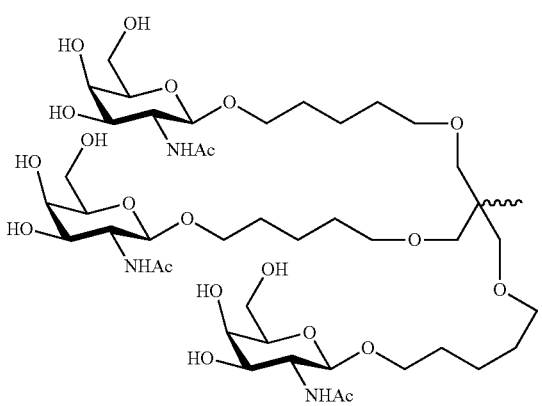
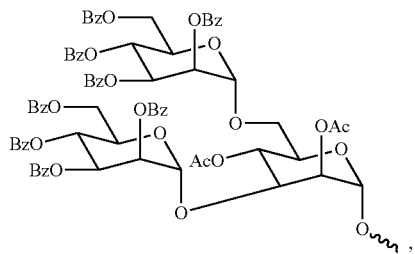
Formula VIII
Formula IX
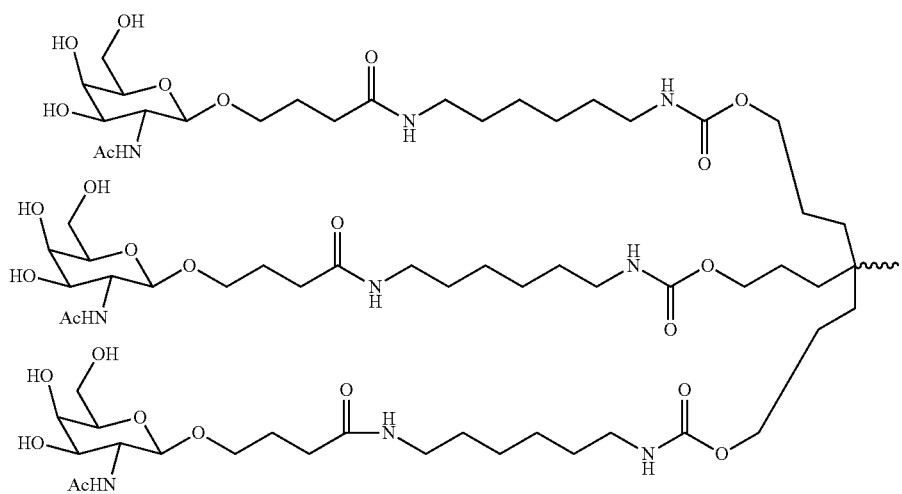

Formula X
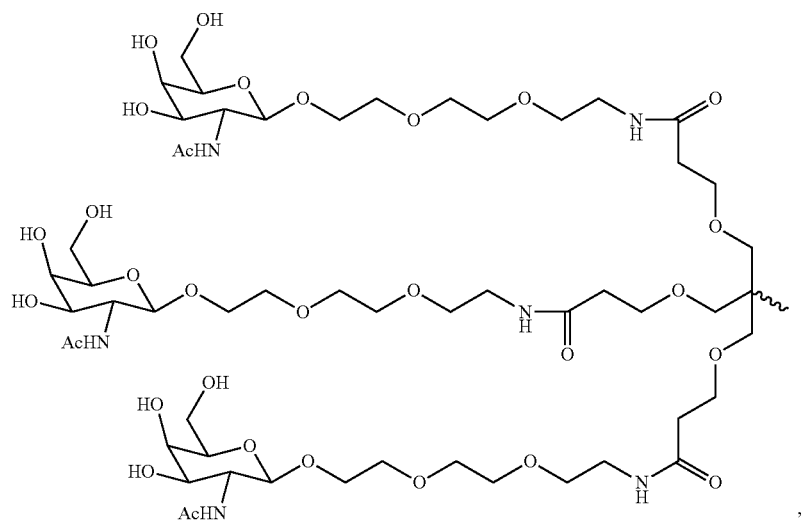
Formula XI
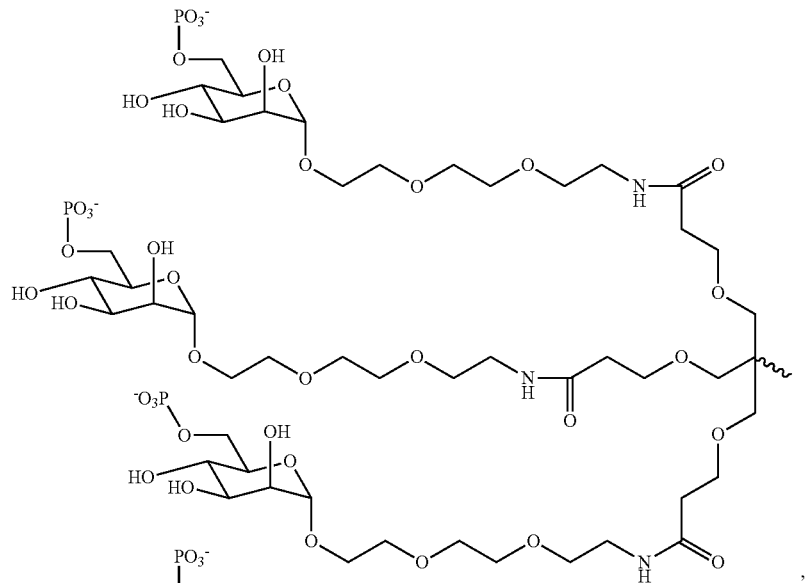
Formula XII
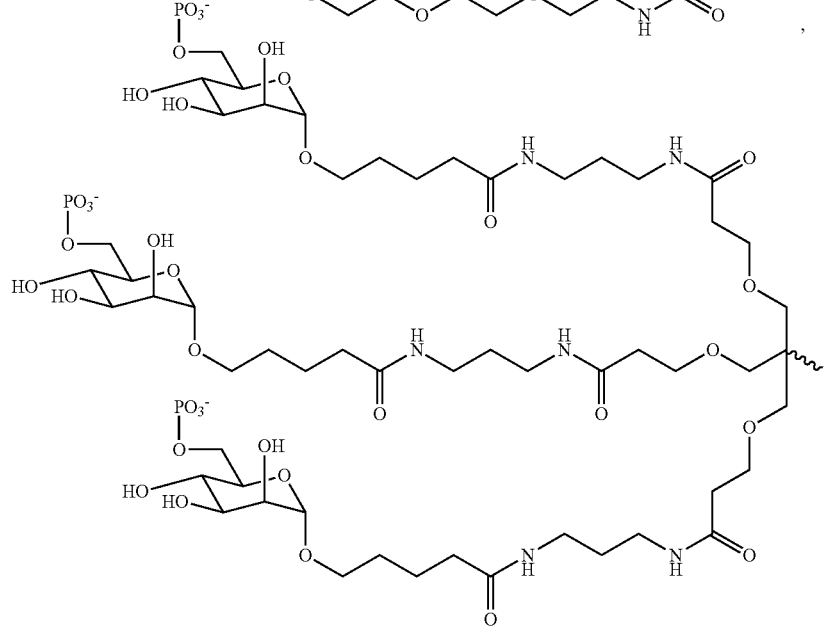

Formula XIII
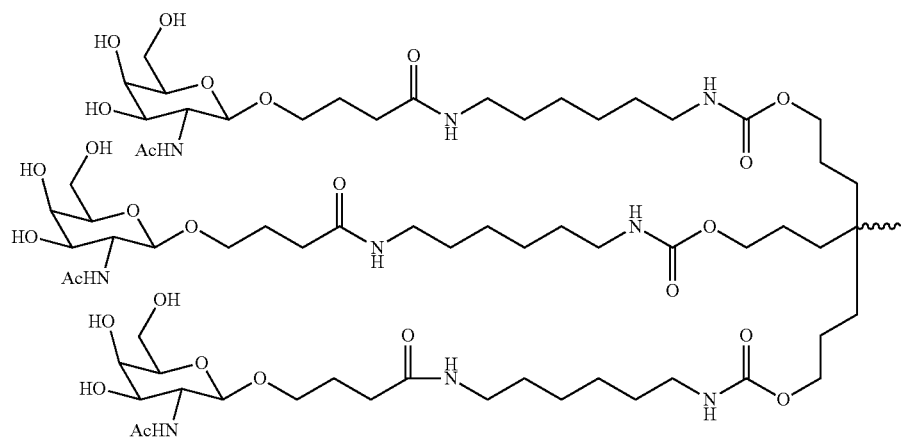
Formula XIV
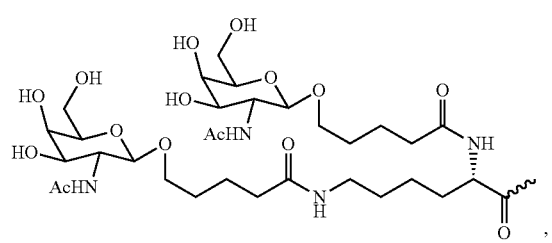
Formula XV
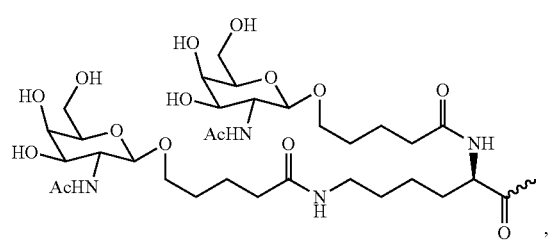
Formula XVI
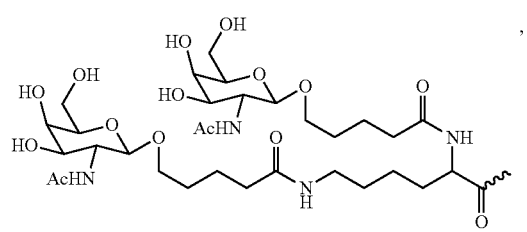
Formula XVII
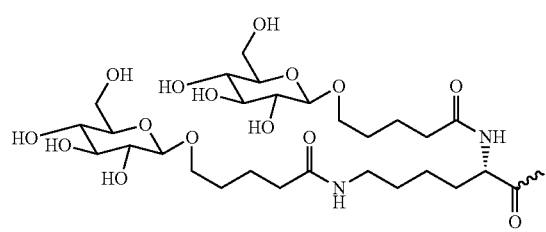
Formula XVIII
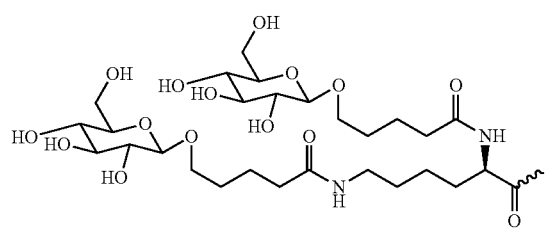
Formula XIX
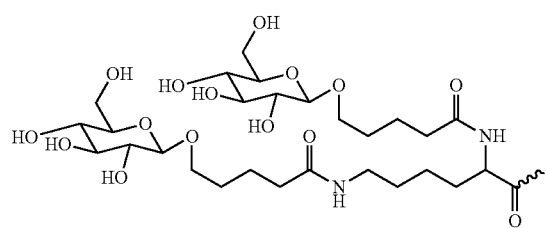

Formula XX 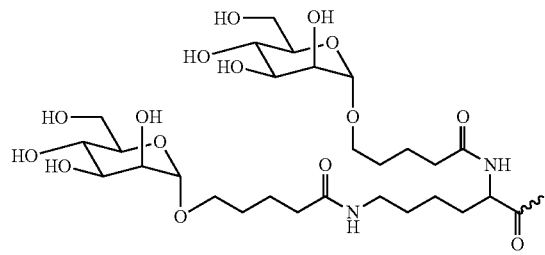
Formula XXI 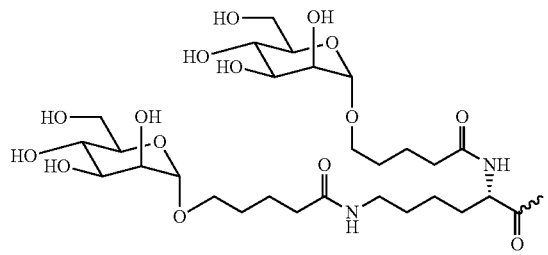
Formula XXII 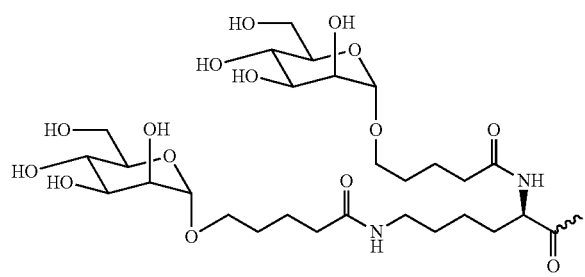
In one embodiment, the GalNAc or a GalNAc derivative is GalNAc₃:
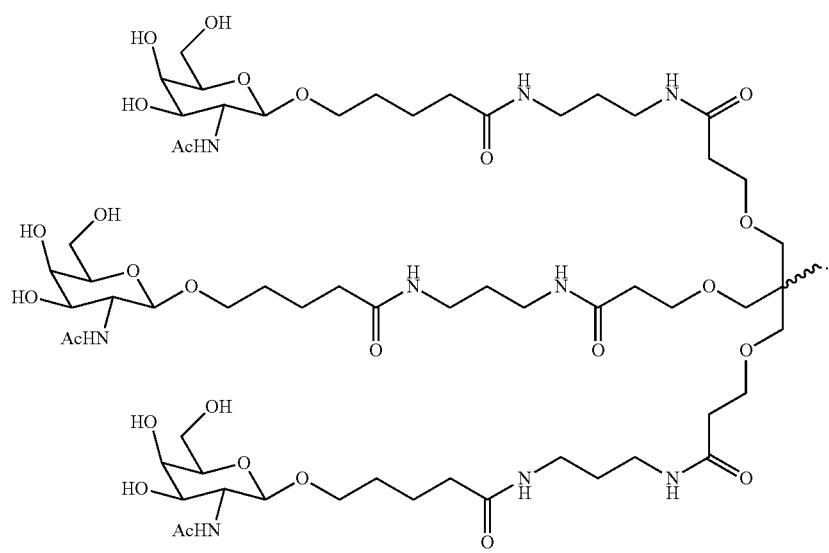 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
In some embodiments, the ligand, e.g., GalNAc ligand, is attached to the 3' end of the RNAi agent. In one embodiment, the RNAi agent is conjugated to the ligand, e.g., GalNAc ligand, as shown in the following schematic

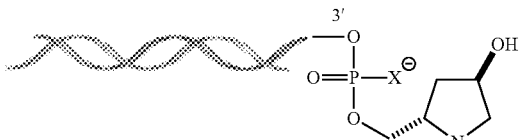
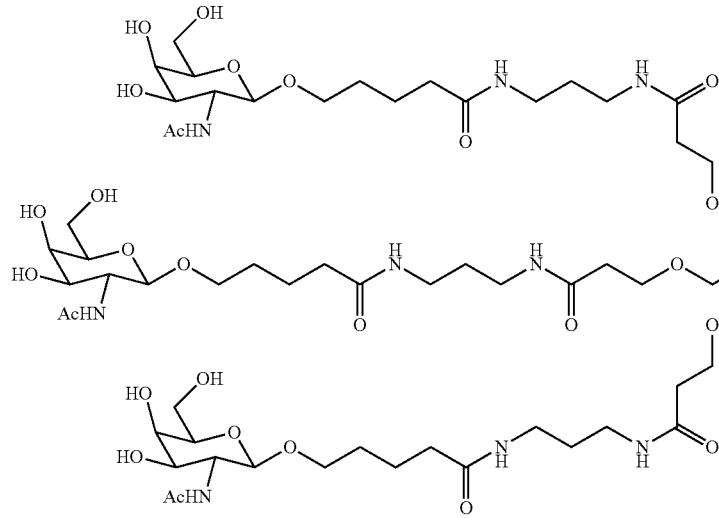

wherein X is O or S. In one embodiment, X is O.

A wide variety of entities can be coupled to the RNAi agents of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., *Biochemistry*, 1987, 26: 2964-2972), the EALA peptide (Vogel et al., *J. Am. Chem. Soc.*, 1996, 118: 1581-1586), and their derivatives (Turk et al., *Biochem. Biophys. Acta*, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g., acridines), cross-linkers (e.g., psoralen, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by, for example, activating an inflammatory response. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 9). An RFGF analogue (e.g., amino acid sequence AALLPVLLAAP (SEQ ID NO: 10)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11)) and the *Drosophila* Antennapedia protein (RQIKIWFQNRRMKWKK (SEQ ID NO: 12)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., *Cancer Res.,* 62:5139-43, 2002). An RGD peptide can facilitate targeting of an iRNA agent to tumors of a variety of other tissues, including the lung, kidney, spleen, or liver (Aoki et al., *Cancer Gene Therapy* 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., *Jour. Nucl. Med.,* 42:326-336, 2001). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type of ligand target PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as ligands (e.g., as PK modulating ligands).

In addition, aptamers that bind serum components (e.g., serum proteins) are also amenable to the present invention as PK modulating ligands.

Other ligand conjugates amenable to the invention are described in U.S. patent applications U.S. Ser. No. 10/916, 185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g., a carrier described herein. The ligand or tethered ligand may be present on a monomer when the monomer is incorporated into the growing strand. In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., TAP—$(CH_2)_n NH_2$ may be incorporated into a growing oligonucelotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated, e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double stranded iRNA agent contains a ligand conjugated to the sense strand. In other embodiments, a double stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a monovalent, a bivalent or a trivalent branched linker.

In one embodiment, the dsRNA of the invention is conjugated to a bivalent and trivalent branched linkers include the structures shown in any of formula (IV)-(VII):

Formula (IV)

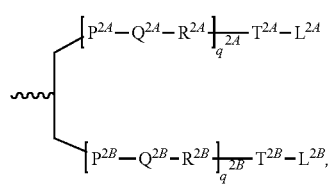

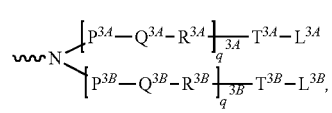

Formula (V)

Formula (VI)

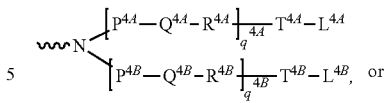

Formula (VII)

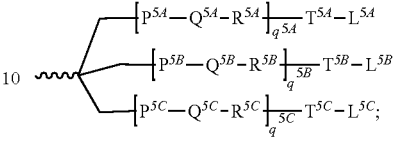

wherein:
$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R), C(R$^N$)=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O), —CH(R$^a$)—NH—, CO, CH=N—O,

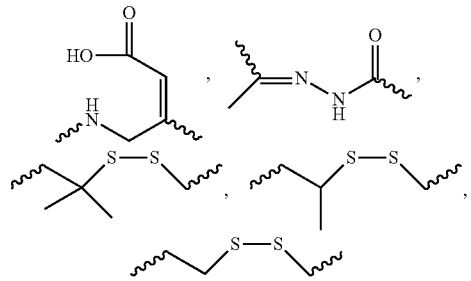

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

Formula (VII)

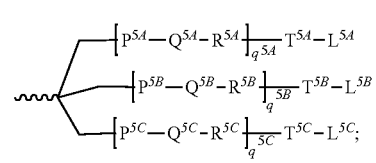

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the following compounds:

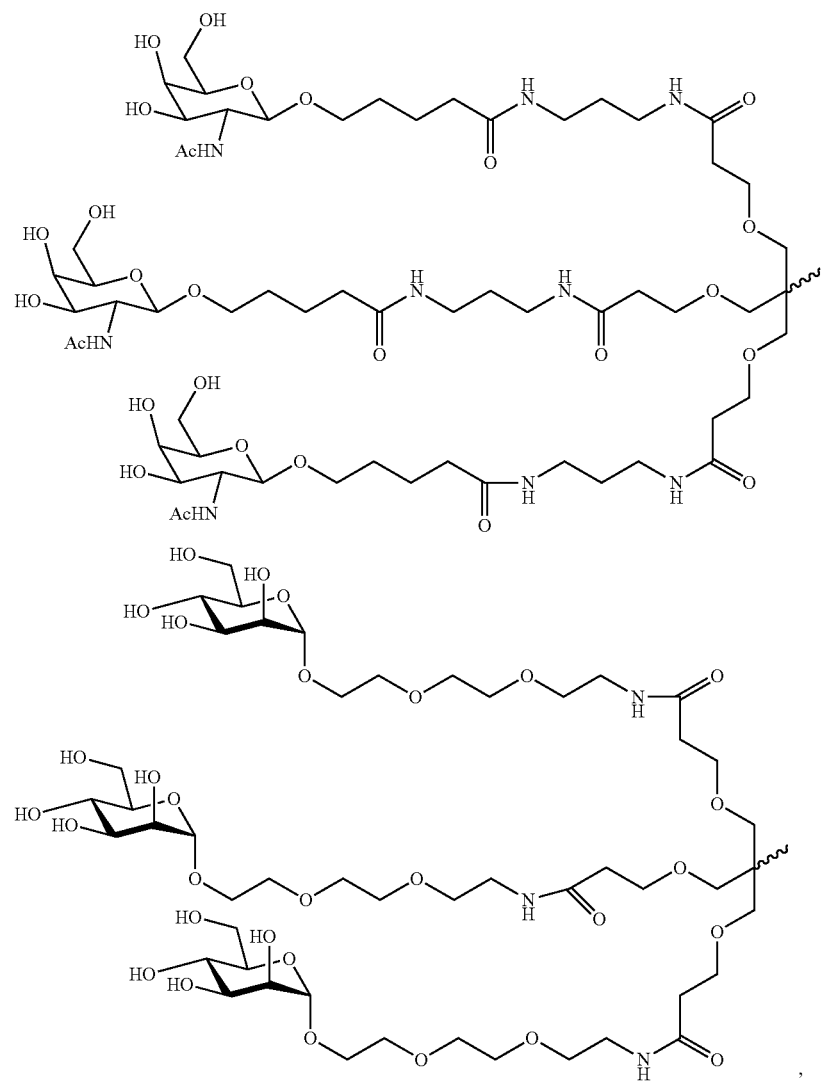
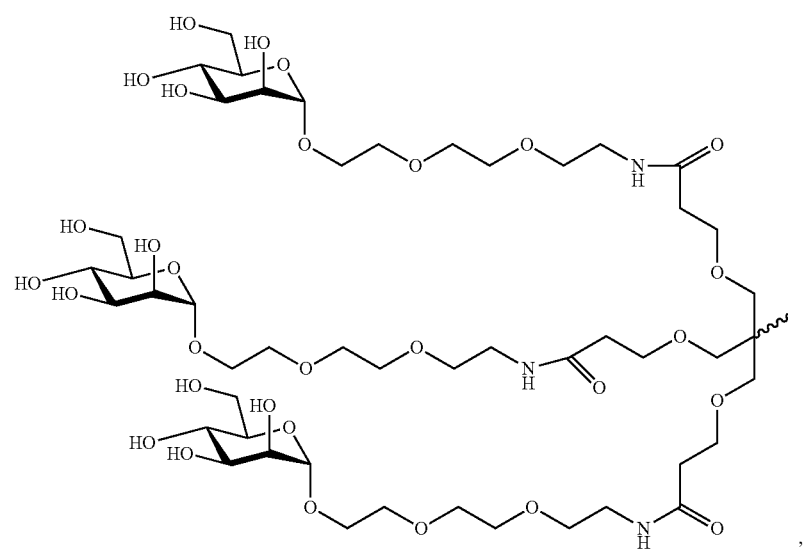

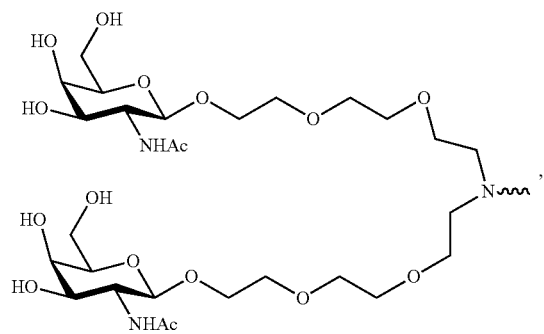
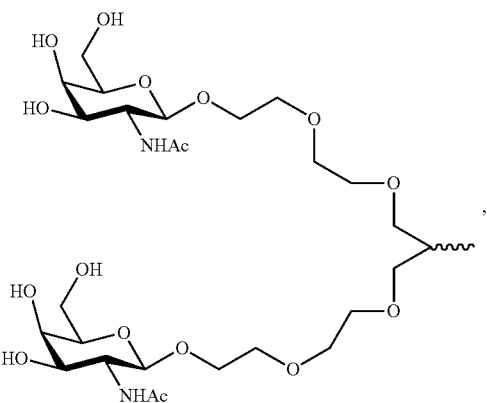
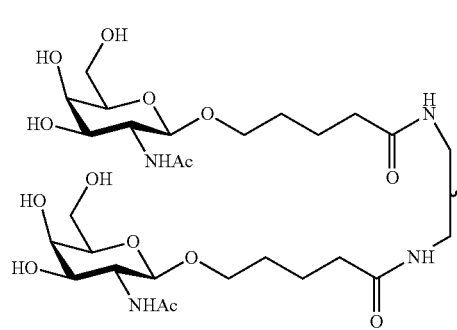
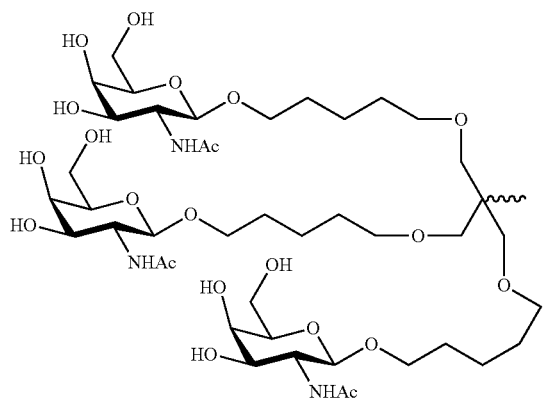
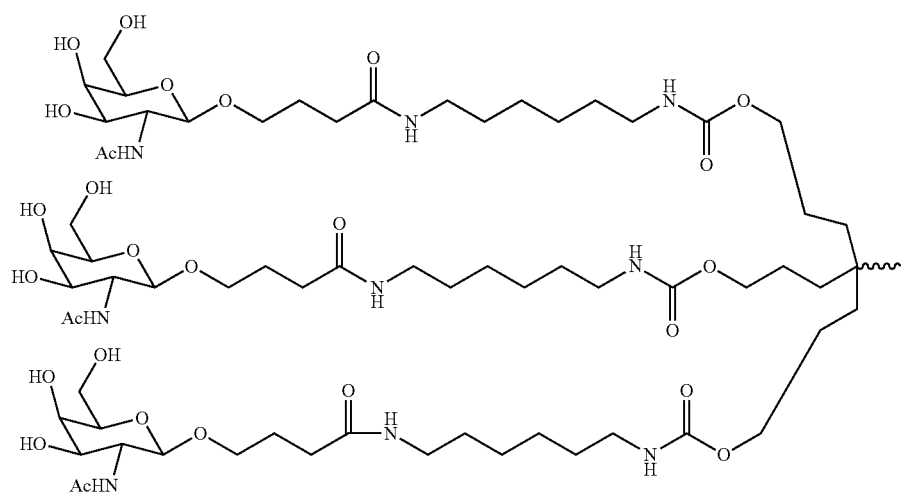

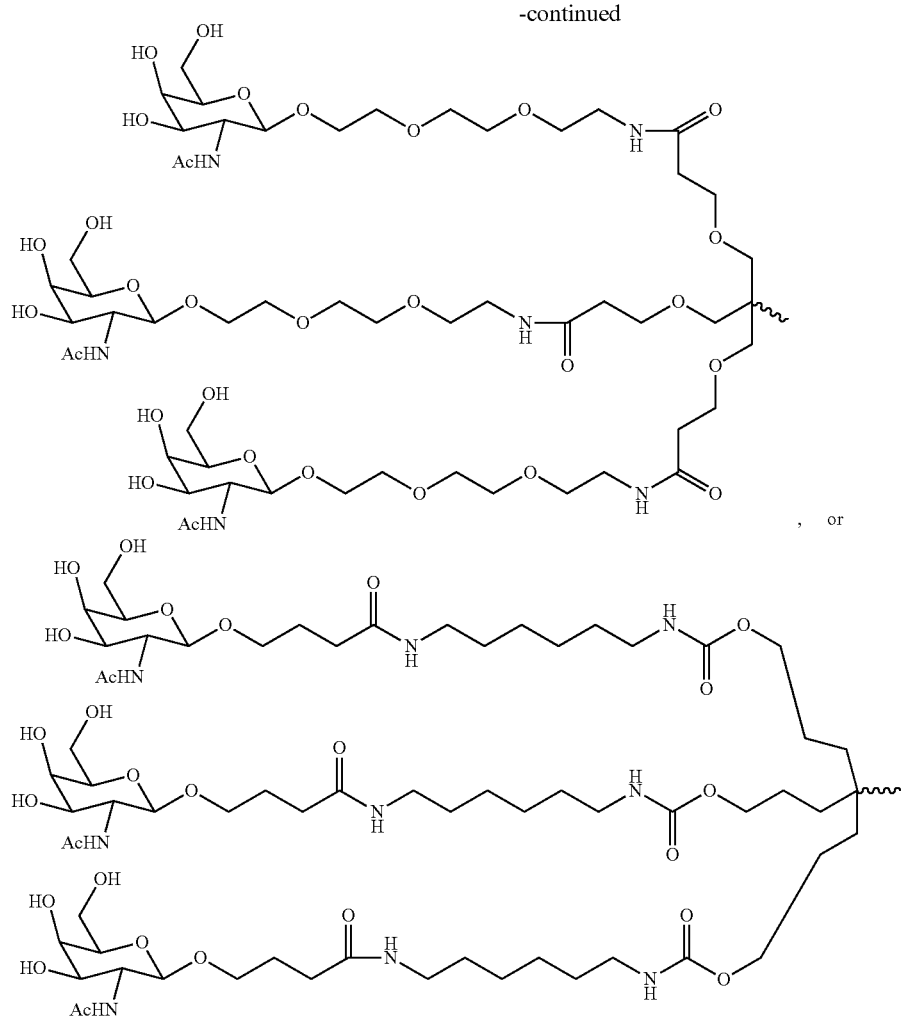

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T.

et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

In some embodiments, a double stranded RNAi agent of the invention is AD-57213.

VI. DELIVERY OF AN IRNA OF THE INVENTION

The delivery of an iRNA of the invention to a cell e.g., a cell within a subject, such as a human subject (e.g., a subject in need thereof, such as a subject having a bleeding disorder) can be achieved in a number of different ways. For example, delivery may be performed by contacting a cell with an iRNA of the invention either in vitro or in vivo. In vivo delivery may be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the Serpinc1 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics* and *Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol*, 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. PHARMACEUTICAL COMPOSITIONS OF THE INVENTION

The present invention also provides pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a Serpinc1 gene, e.g. a Serpinc1-associated disease. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a Serpinc1 gene.

In certain embodiments of the invention, for example, when a pharmaceutical composition comprises a double stranded RNAi agent includes one or more motifs of three identical modifications on three consecutive nucleotides, including one such motif at or near the cleavage site of the agent, six phosphorothioate linkages, and a GalNAc ligand, such a composition is administered at a dose of 0.200 to about 1.825 mg/kg, 0.200 to about 1.800 mg/kg, about 0.200 to about 1.700 mg/kg, about 0.200 to about 1.600 mg/kg, about 0.200 to about 1.500 mg/kg, about 0.200 to about 1.400 mg/kg, about 0.200 to about 1.400 mg/kg, about 0.200 to about 1.200 mg/kg, about 0.200 to about 1.100 mg/kg, about 0.200 to about 1.000 mg/kg, about 0.200 to about 0.900 mg/kg, about 0.200 to about 0.800 mg/kg, about 0.200 to about 0.700 mg/kg, about 0.200 to about 0.600 mg/kg, about 0.200 to about 0.500 mg/kg, about 0.200 to about 0.400 mg/kg, about 0.225 to about 1.825 mg/kg, about 0.225 to about 1.800 mg/kg, about 0.225 to about 1.700 mg/kg, about 0.225 to about 1.600 mg/kg, about 0.225 to about 1.500 mg/kg, about 0.225 to about 1.400 mg/kg, about 0.225 to about 1.400 mg/kg, about 0.225 to about 1.200 mg/kg, about 0.225 to about 1.100 mg/kg, about 0.225 to about 1.000 mg/kg, about 0.225 to about 0.900 mg/kg, about 0.225 to about 0.800 mg/kg, about 0.225 to about 0.700 mg/kg, about 0.225 to about 0.600 mg/kg, about 0.225 to about 0.500 mg/kg, about 0.225 to about 0.400 mg/kg, about 0.250 to about 1.825 mg/kg, about 0.250 to about 1.800 mg/kg, about 0.250 to about 1.700 mg/kg, about 0.250 to about 1.600 mg/kg, about 0.250 to about 1.500 mg/kg, about 0.250 to about 1.400 mg/kg, about 0.250 to about 1.400 mg/kg, about 0.250 to about 1.200 mg/kg, about 0.250 to about 1.100 mg/kg, about 0.250 to about 1.000 mg/kg, about 0.250 to about 0.900 mg/kg, about 0.250 to about 0.800 mg/kg, about 0.250 to about 0.700 mg/kg, about 0.250 to about 0.600 mg/kg, about 0.250 to about 0.500 mg/kg, about 0.250 to about 0.400 mg/kg, about 0.425 to about 1.825 mg/kg, about 0.425 to about 1.800 mg/kg, about 0.425 to about 1.700 mg/kg, about 0.425 to about 1.600 mg/kg, about 0.425 to about 1.500 mg/kg, about 0.425 to about 1.400 mg/kg, about 0.425 to about 1.400 mg/kg, about 0.425 to about 1.200 mg/kg, about 0.425 to about 1.100 mg/kg, about 0.425 to about 1.000 mg/kg, about 0.425 to about 0.900 mg/kg, about 0.425 to about 0.800 mg/kg, about 0.425 to about 0.700 mg/kg, about 0.425 to about 0.600 mg/kg, about 0.425 to about 0.500 mg/kg, about 0.450 to about 1.825 mg/kg, about 0.450 to about 1.800 mg/kg, about 0.450 to about 1.700 mg/kg, about 0.450 to about 1.600 mg/kg, about 0.450 to about 1.500 mg/kg, about 0.450 to about 1.400 mg/kg, about 0.450 to about 1.400 mg/kg, about 0.450 to about 1.200 mg/kg, about 0.450 to about 1.100 mg/kg, about 0.450 to about 1.000 mg/kg, about 0.450 to about 0.900 mg/kg, about 0.450 to about 0.800 mg/kg, about 0.450 to about 0.700 mg/kg, about 0.450 to about 0.600 mg/kg, about 0.450 to about 0.500 mg/kg, about 0.475 to about 1.825 mg/kg, about 0.475 to about 1.800 mg/kg, about 0.475 to about 1.700 mg/kg, about 0.475 to about 1.600 mg/kg, about 0.475 to about 1.500 mg/kg, about 0.475 to about 1.400 mg/kg, about 0.475 to about 1.400 mg/kg, about 0.475 to about 1.200 mg/kg, about 0.475 to about 1.100 mg/kg, about 0.475 to about 1.000 mg/kg, about 0.475 to about 0.900 mg/kg, about 0.475 to about 0.800 mg/kg, about 0.475 to about 0.700 mg/kg, about 0.475 to about 0.600 mg/kg, about 0.475 to about 0.500 mg/kg, about 0.875 to about 1.825 mg/kg, about 0.875 to about 1.800 mg/kg, about 0.875 to about 1.700 mg/kg, about 0.875 to about 1.600 mg/kg, about 0.875 to about 1.500 mg/kg, about 0.875 to about 1.400 mg/kg, about 0.875 to about 1.400 mg/kg, about 0.875 to about 1.200 mg/kg, about 0.875 to about 1.100 mg/kg, about 0.875 to about 1.000 mg/kg, about 0.875 to about 0.900 mg/kg, about 0.900 to about 1.825 mg/kg, about 0.900 to about 1.800 mg/kg, about 0.900 to about 1.700 mg/kg, about 0.900 to about 1.600 mg/kg, about 0.900 to about 1.500 mg/kg, about 0.900 to about 1.400 mg/kg, about 0.900 to about 1.400 mg/kg, about 0.900 to about 1.200 mg/kg, about 0.900 to about 1.100 mg/kg, about 0.900 to about 1.000 mg/kg, about 0.925 to about 1.825 mg/kg, about 0.925 to about 1.800 mg/kg, about 0.925 to about 1.700 mg/kg, about 0.925 to about 1.600 mg/kg, about 0.925 to about 1.500 mg/kg, about 0.925 to about 1.400 mg/kg, about 0.925 to about 1.400 mg/kg, about 0.925 to about 1.200 mg/kg, about 0.925 to about 1.100 mg/kg, or about 0.925 to about 1.000 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, about 0.5 mg/kg, 0.525 mg/kg, 0.55 mg/kg, 0.575 mg/kg, about 0.6 mg/kg, 0.625 mg/kg, 0.65 mg/kg, 0.675 mg/kg, about 0.7 mg/kg, 0.725 mg/kg, 0.75 mg/kg, 0.775 mg/kg, about 0.8 mg/kg, 0.925 mg/kg, 0.95 mg/kg, 0.975 mg/kg, about 1.0 mg/kg, 1.025 mg/kg, 1.05 mg/kg, 1.075 mg/kg, about 1.1 mg/kg, 1.125 mg/kg, 1.15 mg/kg, 1.175 mg/kg, about 1.2 mg/kg, 1.225 mg/kg, 1.25 mg/kg, 1.275 mg/kg, about 1.3 mg/kg, 1.325 mg/kg, 1.35 mg/kg, 1.375 mg/kg, about 1.4 mg/kg, 1.425 mg/kg, 1.45 mg/kg, 1.475 mg/kg, about 1.5 mg/kg, 1.525 mg/kg, 1.55 mg/kg, 1.575 mg/kg, about 1.6 mg/kg, 1.625 mg/kg, 1.65 mg/kg, 1.675 mg/kg, about 1.7 mg/kg, 1.725 mg/kg, 1.75 mg/kg, 1.775 mg/kg, or about 1.8 mg/kg. Values intermediate to the foregoing recited values are also intended to be part of this invention.

In some embodiments of the invention, for example, when a double stranded RNAi agent comprises a sense strand and an antisense strand, the antisense strand comprising a region of complementarity which comprises at least 15 contiguous nucleotides differing by no more than 3 nucleotides from the nucleotide sequence of 5'-UUGAAGUAAAUGGU-GUUAACCAG-3' (SEQ ID NO: 15), wherein substantially all of the nucleotides of the sense strand and substantially all of the nucleotides of the antisense strand are modified nucleotides, and wherein the sense strand is conjugated to a ligand attached at the 3'-terminus, such an agent in a pharmaceutical composition is administered at a dose of about 0.200 to about 1.825 mg/kg, 0.200 to about 1.800 mg/kg, about 0.200 to about 1.700 mg/kg, about 0.200 to about 1.600 mg/kg, about 0.200 to about 1.500 mg/kg, about 0.200 to about 1.400 mg/kg, about 0.200 to about 1.400 mg/kg, about 0.200 to about 1.200 mg/kg, about 0.200 to about 1.100 mg/kg, about 0.200 to about 1.000 mg/kg, about 0.200 to about 0.900 mg/kg, about 0.200 to about 0.800 mg/kg, about 0.200 to about 0.700 mg/kg, about 0.200 to about 0.600 mg/kg, about 0.200 to about 0.500 mg/kg, about 0.200 to about 0.400 mg/kg, about 0.225 to about 1.825 mg/kg, about 0.225 to about 1.800 mg/kg, about 0.225 to about 1.700 mg/kg, about 0.225 to about 1.600 mg/kg, about 0.225 to about 1.500 mg/kg, about 0.225 to about 1.400 mg/kg, about 0.225 to about 1.400 mg/kg, about 0.225 to about 1.200 mg/kg, about 0.225 to about 1.100 mg/kg, about 0.225 to about 1.000 mg/kg, about 0.225 to about 0.900 mg/kg, about 0.225 to about 0.800 mg/kg, about 0.225 to about 0.700 mg/kg, about 0.225 to about 0.600 mg/kg, about 0.225 to about 0.500 mg/kg, about 0.225 to about 0.400 mg/kg, about 0.250 to about 1.825 mg/kg, about 0.250 to about 1.800 mg/kg, about 0.250 to about 1.700 mg/kg, about 0.250 to about 1.600 mg/kg, about 0.250 to about 1.500 mg/kg, about 0.250 to about 1.400 mg/kg, about 0.250 to about 1.400 mg/kg, about 0.250 to about 1.200 mg/kg, about 0.250 to about 1.100 mg/kg, about 0.250 to about 1.000 mg/kg, about 0.250 to about 0.900 mg/kg, about 0.250 to about 0.800 mg/kg, about 0.250 to about 0.700 mg/kg, about 0.250 to about 0.600 mg/kg, about 0.250 to about 0.500 mg/kg, about 0.250 to about 0.400 mg/kg, about 0.425 to about 1.825 mg/kg, about 0.425 to about 1.800 mg/kg, about 0.425 to about 1.700 mg/kg, about 0.425 to about 1.600 mg/kg, about 0.425 to about 1.500 mg/kg, about 0.425 to about 1.400 mg/kg, about 0.425 to about 1.400 mg/kg, about 0.425 to about 1.200 mg/kg, about 0.425 to about 1.100 mg/kg, about 0.425 to about 1.000 mg/kg, about 0.425 to about 0.900 mg/kg, about 0.425 to about 0.800 mg/kg, about 0.425 to about 0.700 mg/kg, about 0.425 to about 0.600 mg/kg, about 0.425 to about 0.500 mg/kg, about 0.450 to about 1.825 mg/kg, about 0.450 to about 1.800 mg/kg, about 0.450 to about 1.700 mg/kg, about 0.450 to about 1.600 mg/kg, about 0.450 to about 1.500 mg/kg, about 0.450 to about 1.400 mg/kg, about 0.450 to about 1.400 mg/kg, about 0.450 to about 1.200 mg/kg, about 0.450 to about 1.100 mg/kg, about 0.450 to about 1.000 mg/kg, about 0.450 to about 0.900 mg/kg, about 0.450 to about 0.800 mg/kg, about 0.450 to about 0.700 mg/kg, about 0.450 to about 0.600 mg/kg, about 0.450 to about 0.500 mg/kg, about 0.475 to about 1.825 mg/kg, about 0.475 to about 1.800 mg/kg, about 0.475 to about 1.700 mg/kg, about 0.475 to about 1.600 mg/kg, about 0.475 to about 1.500 mg/kg, about 0.475 to about 1.400 mg/kg, about 0.475 to about 1.400 mg/kg, about 0.475 to about 1.200 mg/kg, about 0.475 to about 1.100 mg/kg, about 0.475 to about 1.000 mg/kg, about 0.475 to about 0.900 mg/kg, about 0.475 to about 0.800 mg/kg, about 0.475 to about 0.700 mg/kg, about 0.475 to about 0.600 mg/kg, about 0.475 to about 0.500 mg/kg, about 0.875 to about 1.825 mg/kg, about 0.875 to about 1.800 mg/kg, about 0.875 to about 1.700 mg/kg, about 0.875 to about 1.600 mg/kg, about 0.875 to about 1.500 mg/kg, about 0.875 to about 1.400 mg/kg, about 0.875 to about 1.400 mg/kg, about 0.875 to about 1.200 mg/kg, about 0.875 to about 1.100 mg/kg, about 0.875 to about 1.000 mg/kg, about 0.875 to about 0.900 mg/kg, about 0.900 to about 1.825 mg/kg, about 0.900 to about 1.800 mg/kg, about 0.900 to about 1.700 mg/kg, about 0.900 to about 1.600 mg/kg, about 0.900 to about 1.500 mg/kg, about 0.900 to about 1.400 mg/kg, about 0.900 to about 1.400 mg/kg, about 0.900 to about 1.200 mg/kg, about 0.900 to about 1.100 mg/kg, about 0.900 to about 1.000 mg/kg, about 0.925 to about 1.825 mg/kg, about 0.925 to about 1.800 mg/kg, about 0.925 to about 1.700 mg/kg, about 0.925 to about 1.600 mg/kg, about 0.925 to about 1.500 mg/kg, about 0.925 to about 1.400 mg/kg, about 0.925 to about 1.400 mg/kg, about 0.925 to about 1.200 mg/kg, about 0.925 to about 1.100 mg/kg, or about 0.925 to about 1.000 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, about 0.5 mg/kg, 0.525 mg/kg, 0.55 mg/kg, 0.575 mg/kg, about 0.6 mg/kg, 0.625 mg/kg, 0.65 mg/kg, 0.675 mg/kg, about 0.7 mg/kg, 0.725 mg/kg, 0.75 mg/kg, 0.775 mg/kg, about 0.8 mg/kg, 0.925 mg/kg, 0.95 mg/kg, 0.975 mg/kg, about 1.0 mg/kg, 1.025 mg/kg, 1.05 mg/kg, 1.075 mg/kg, about 1.1 mg/kg, 1.125 mg/kg, 1.15 mg/kg, 1.175 mg/kg, about 1.2 mg/kg, 1.225 mg/kg, 1.25 mg/kg, 1.275 mg/kg, about 1.3 mg/kg, 1.325 mg/kg, 1.35 mg/kg, 1.375 mg/kg, about 1.4 mg/kg, 1.425 mg/kg, 1.45 mg/kg, 1.475 mg/kg, about 1.5 mg/kg, 1.525 mg/kg, 1.55 mg/kg, 1.575 mg/kg, about 1.6 mg/kg, 1.625 mg/kg, 1.65 mg/kg, 1.675 mg/kg, about 1.7 mg/kg, 1.725 mg/kg, 1.75 mg/kg, 1.775 mg/kg, or about 1.8 mg/kg. Values intermediate to the foregoing recited values are also intended to be part of this invention.

In some embodiment, a pharmaceutical composition comprising the iRNA agent is administered to a subject as a fixed dose. A "fixed dose" (e.g., a dose in mg) means that one dose of an iRNA agent is used for all subjects regardless of any specific subject-related factors, such as weight. In one particular embodiment, a fixed dose of an iRNA agent of the invention is based on a predetermined weight or age.

In some embodiments, the pharmaceutical composition comprising the iRNA agent is administered as a fixed dose of between about 25 mg to about 100 mg, e.g., between about 25 mg to about 95 mg, between about 25 mg to about 90 mg, between about 25 mg to about 85 mg, between about 25 mg to about 80 mg, between about 25 mg to about 75 mg, between about 25 mg to about 70 mg, between about 25 mg to about 65 mg, between about 25 mg to about 60 mg, between about 25 mg to about 50 mg, between about 50 mg to about 100 mg, between about 50 mg to about 95 mg, between about 50 mg to about 90 mg, between about 50 mg to about 85 mg, between about 50 mg to about 80 mg, between about 30 mg to about 100 mg, between about 30 mg to about 90 mg, between about 30 mg to about 80 mg, between about 40 mg to about 100 mg, between about 40 mg to about 90 mg, between about 40 mg to about 80 mg, between about 60 mg to about 100 mg, between about 60 mg to about 90 mg, between about 25 mg to about 55 mg, between about 30 mg to about 95 mg, between about 30 mg to about 85 mg, between about 30 mg to about 75 mg, between about 30 mg to about 65 mg, between about 30 mg to about 55 mg, between about 40 mg to about 95 mg, between about 40 mg to about 85 mg, between about 40 mg to about 75 mg, between about 40 mg to about 65 mg, between about 40 mg to about 55 mg, or between about 45 mg to about 95 mg.

In some embodiments, the pharmaceutical composition comprising the iRNA agent is administered as a fixed dose of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

A pharmaceutical composition comprising the iRNA may be administered to the subject about once a month, about once every five weeks, about once every six weeks, about once every 2 months, or once a quarter.

A pharmaceutical composition comprising the iRNA agent may be administered to a subject as one or more doses. In some embodiments, pharmaceutical compositions comprising the double stranded iRNA agent may be administered to a subject as a monthly dose of about 0.200 mg/kg to about 0.250 mg/kg, a monthly dose of about 0.425 mg/kg to about 0.475 mg/kg, a monthly dose of about 0.875 mg/kg to about 0.925 mg/kg, or as a monthly dose of about 1.775 mg/kg to about 1.825 mg/kg. In some embodiments, pharmaceutical compositions comprising the double stranded iRNA agent may be administered to a subject as a fixed dose of about 25 mg to about 100 mg, e.g., about 25 mg, about 50 mg, about 80 mg, or about 100 mg.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks), monthly, every two months, every three months, every four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 1, 2, 3, 4, 5, 6, 7, or 8 week intervals. In some embodiments of the invention, a single dose of the pharmaceutical compositions of the invention is administered once per month.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a bleeding disorder that would benefit from reduction in the expression of Serpinc1. Such models can be used for in vivo testing of iRNA, as well as for determining a therapeutically effective dose. Suitable mouse models are known in the art and include, for example, Hemophilia A mouse models and Hemohphilia B mouse models, e.g., mice containing a knock-out of a clotting factor gene, such as those described in Bolliger, et al. (2010) *Thromb Haemost* 103: 1233-1238, Bi L, et al. (1995) *Nat Genet* 10: 119-21, Lin et al. (1997) *Blood* 90: 3962-6, Kundu et al. (1998) *Blood* 92:

168-74, Wang et al. (1997) *Proc Natl Acad Sci USA* 94: 11563-6, and Jin, et al. (2004) *Blood* 104:1733.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Topical formulations are described in detail in U.S. Pat. No. 6,747,014, which is incorporated herein by reference.

A. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (P0310), hexaglycerol pentaoleate (P0500), decaglycerol monocaprate (MCA750), decaglycerol monooleate (M0750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research*, 1994, 11, 1385-1390; Ritschel,

*Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a hemolytic disorder. Examples of such agents include, but are not lmited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the ISERPINC10 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by SERPINC1 expression. In any event, the administering physician can adjust the amount and timing of iRNA administration on the basis of results observed using standard measures of efficacy known in the art or described herein.

VI. KITS

The present invention also provides kits for performing any of the methods of the invention. Such kits include one or more RNAi agent(s) and instructions for use, e.g., instructions for administering a prophylactically or therapeutically effective amount of an RNAi agent(s). The kits may optionally further comprise means for administering the RNAi agent (e.g., an injection device), or means for measuring the inhibition of Serpinc1 (e.g., means for measuring the inhibition of Serpinc1 mRNA, Serpinc1 protein, and/or Serpinc1 activity). Such means for measuring the inhibition of Serpinc1 may comprise a means for obtaining a sample from a subject, such as, e.g., a plasma sample. The kits of the invention may optionally further comprise means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |

Example 1: Administration of a Single Dose of AD-57213 to Healthy Human Subjects Twenty-four healthy human volunteers, in cohorts of 3:1 (active:placebo), were administered a single dose of 0.03 mg/kg, 0.1 mg/kg, 0.3 mg/kg, 0.6 mg/kg, or 1.0 mg/kg of AD-57213 (Sense (5' to 3'): GfsgsUfuAfaCfaCfCfAfuUfuAfcUfuCfaAfL96 (SEQ ID NO:13); Antisense (5' to 3'): usUfsgAfaGfuAfaAfuggUfgUfuAfaCfcsasg (SEQ ID NO:14)). Plasma samples were collected at days 0, 1, 2, 3, 7, 10, 14, 21, 28, 42, 56, and 70 after administration to monitor AT protein levels, AT activity, and duration of AT protein silencing. AT protein levels were monitored using ELISA and AT activity levels were monitored by generation of thrombin generation curves using a Calibrated Automated Thrombinoscope (tissue factor=1 pM). Fold change in peak thrombin was calculated relative to the average peak thrombin value for two pre-dose values for each subject.

There were no serious adverse events, 3 mild adverse events that were not likely related to the administration of the agent, and 1 mild adverse event (headache) that was potentially related to the administration of the agent. There were also no injection site reactions and the physical examinations, vital signs, and electrocardiograms of all subjects were within normal limits. In addition, all liver function tests, total bilirubin levels, international normalized ratio of prothrombin times (PT/INR), platelet counts, hemoglobin levels, and coagulation tests (i.e., activated partial thromboplastin times (APTT), prothrombin times (PT), fibrinogen levels, and fibrin D-dimer levels) of all subjects did not change during the course of the study and were within normal limits.

FIGS. 1A-D and 2A-B show that a single dose of 0.03 mg/kg of AD-57213 results in approximately 20% and up to 33% reduction in AT protein levels (FIGS. 2A and 2B) and a corresponding reduction in AT activity (FIGS. 1A-D) with a durability of lowering of greater than 60 days.

Figure 3:
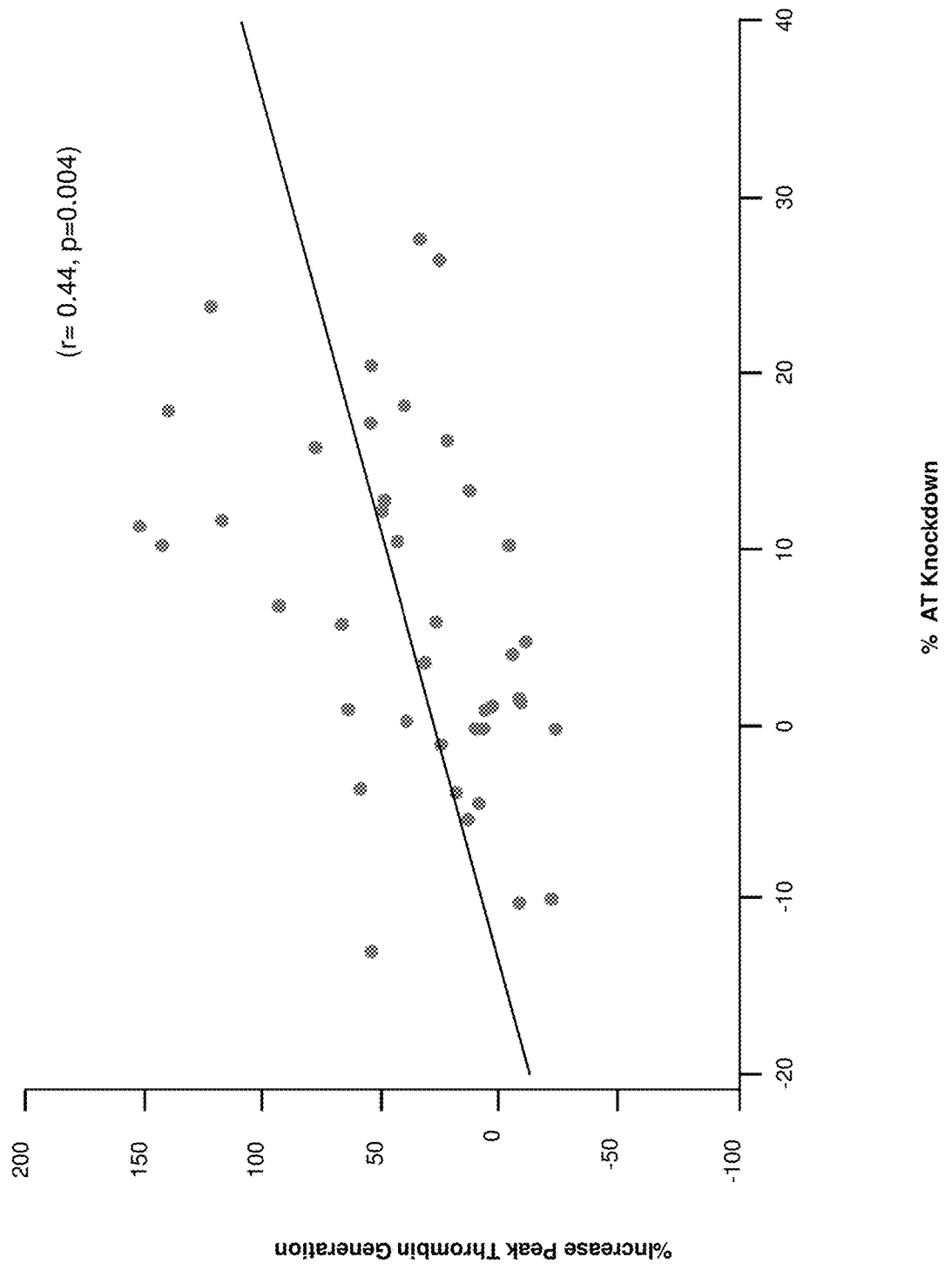
FIG. 3 is a graph depicting the association between the percent of AT (Serpinc1) knockdown and the percent increase in peak thrombin generation in healthy subjects administered a single subcutaneous 0.03 mg/kg dose of AD-57213.

FIG. 3 further demonstrates that there is a significant association between AT knockdown and peak thrombin generation. Specifically, up to 152% increase in peak thrombin generation was observed, with a mean maximum increase of peak thrombin of 138%±8.9% (mean±SEM). In addition, and consistent with an increased thrombin generation with increased AT knockdown, the levels of Factor VIII or IX were normal.

Example 2: Administration of Multiple Doses of AD-57213 to Human Patients Having Hemophilia A or B Phase I—Parts B, C, and D Clinical Trial In Part B of a Phase I clinical trial of AD-57213 (Sense (5' to 3'): GfsgsUfuAfaCfaCfCfAfuUfuAfcUfuCfaAfL96 (SEQ ID NO:13); Antisense (5' to 3'): usUfsgAfaGfuAfaAfuggUfgUfuAfaCfcsasg (SEQ ID NO:14)), three patients having Hemophilia A (n=2) or B (n=1) were subcutaneously administered 0.015 mg/kg weekly for three weeks (15 micrograms/kg qw×3; 15 mcg/kg) of AD-57213; six patients having Hemophilia A were subcutaneously administered 0.045 mg/kg weekly for three weeks (45 micrograms/kg qw×3; 45 mcg/kg) of AD-57213; and three patients having Hemophilia A (n=2) or B (n=1) were subcutaneously administered 0.075 mg/kg weekly for three weeks (75 micrograms/kg qw×3; 75 mcg/kg) of AD-57213.

In Part C of a Phase I clinical trial of AD-57213 (Sense (5' to 3'): GfsgsUfuAfaCfaCfCfAfuUfuAfcUfuCfaAfL96 (SEQ ID NO:13); Antisense (5' to 3'): usUfsgAfaGfuAfaAfuggUfgUfuAfaCfcsasg (SEQ ID NO:14)), three patients having Hemophilia A (n=2) or B (n=1) were subcutaneously administered a monthly 0.225 mg/kg dose of AD-57213 for three months (225 micrograms/kg qm×3; 225 mcg/kg); three patients having Hemophilia A (n=2) or B (n=1) were subcutaneously administered a monthly 0.450 mg/kg dose of AD-57213 for three months (450 micrograms/kg qm×3; 450 mcg/kg); three patients having Hemophilia A were subcutaneously administered a monthly 0.900 mg/kg dose of AD-57213 for three months (900 micrograms/kg qm×3; 900 mcg/kg); three patients having Hemophilia A were subcutaneously administered a monthly 1.800 mg/kg dose of AD-57213 for three months (1800 micrograms/kg qm×3; 1800 mcg/kg); and six patients having Hemophilia A (n=3) or B (n=3) were subcutaneously administered a monthly fixed dose of 80 mg of AD-57213 for three months (80 mg qM×3).

In Part D of a Phase I clinical trial of AD-57213 (Sense (5' to 3'): GfsgsUfuAfaCfaCfCfAfuUfuAfcUfuCfaAfL96 (SEQ ID NO:13); Antisense (5' to 3'): usUfsgAfaGfuAfaAfuggUfgUfuAfaCfcsasg (SEQ ID NO:14)), six inhibitor patients having Hemophilia A (n=5) or B (n=1) and utilizing bypassing agents (BPAs) for bleed management were subcutaneously administered a fixed dose of 50 mg of AD-57213 monthly for three months (50 mg qM×3); and 10 patients having Hemophilia A and utilizing bypassing agents (BPAs) for bleed management were subcutaneously administered a fixed dose of 80 mg of AD-57213 monthly for three months (80 mg qM×3).

Plasma samples were collected after administration of AD-57213 to monitor AT protein levels, AT activity, and duration of AT protein silencing. AT protein levels were monitored using ELISA and AT activity levels were monitored by generation of thrombin generation curves using a Calibrated Automated Thrombino scope (tissue factor=1 pM). Fold change in peak thrombin was calculated relative to the average peak thrombin value for two pre-dose values for each subject.

The demographics and baseline characteristics of the patients participating in Parts B, C, and D of the study are provided in Table 2.

TABLE 2

| Demographics and baseline characteristics of study participants | | | | | | | | | | |
|---|---|---|---|---|---|---|---|---|---|---|
| | Part B Subcutaneous Weekly × 3 | | | Part C Subcutaneous Monthly × 3 | | | | | Part D Subcutaneous Monthly × 3 | |
| | 15 mcg/kg N = 3 | 45 mcg/kg N = 6 | 75 mcg/kg N = 3 | 225 mcg/kg N = 3 | 450 mcg/kg N = 3 | 900 mcg/kg N = 3 | 1800 mcg/kg N = 3 | 80 mg N = 6 | 50 mg N = 6 | 80 mg N = 10 |
| Age, mean (SD) | 28 (9) | 42 (14) | 40 (4) | 37 (21) | 37 (15) | 38 (16) | 46 (12) | 32 (12) | 32 (7) | 37 |
| Hemophilia A | 2 | 6 | 2 | 2 | 2 | 3 | 3 | 3 | 5 | 10 |
| Hemophilia B | 1 | 0 | 1 | 1 | 1 | 0 | 0 | 3 | 1 | 0 |
| Severe | 3 | 6 | 3 | 2 | 3 | 2 | 3 | 5 | 6 | 10 |
| Moderate | 0 | 0 | 0 | 1 | 0 | 1 | 0 | 1 | 0 | 0 |
| Weight (kg), mean (SD) | 76 (10) | 80 (22) | 82 (8) | 85 (12) | 76 (16) | 76 (2) | 71 (12) | 74 (10) | 73 (17) | 73 |
| Medical History of Hepatitis C | | | | | | | | | 3 | 9 |

For Parts B, C, and D of the study, there were no serious adverse events, no discontinuations, no injection site reactions and the physical examinations, vital signs, and electrocardiograms of all patients were within normal limits. In addition, all liver function tests, and complete blood counts of all patients did not change during the course of the study and were within normal limits. There were also no thromboembolic events during the course of this study and no clinically significant fibrin D-dimer level increases in any of the patients. Any bleed events were successfully managed with standard replacement factor or bypass agent administration. Furthermore, there were no instances of anti-drug antibody (ADA) formation.

Figure 4:
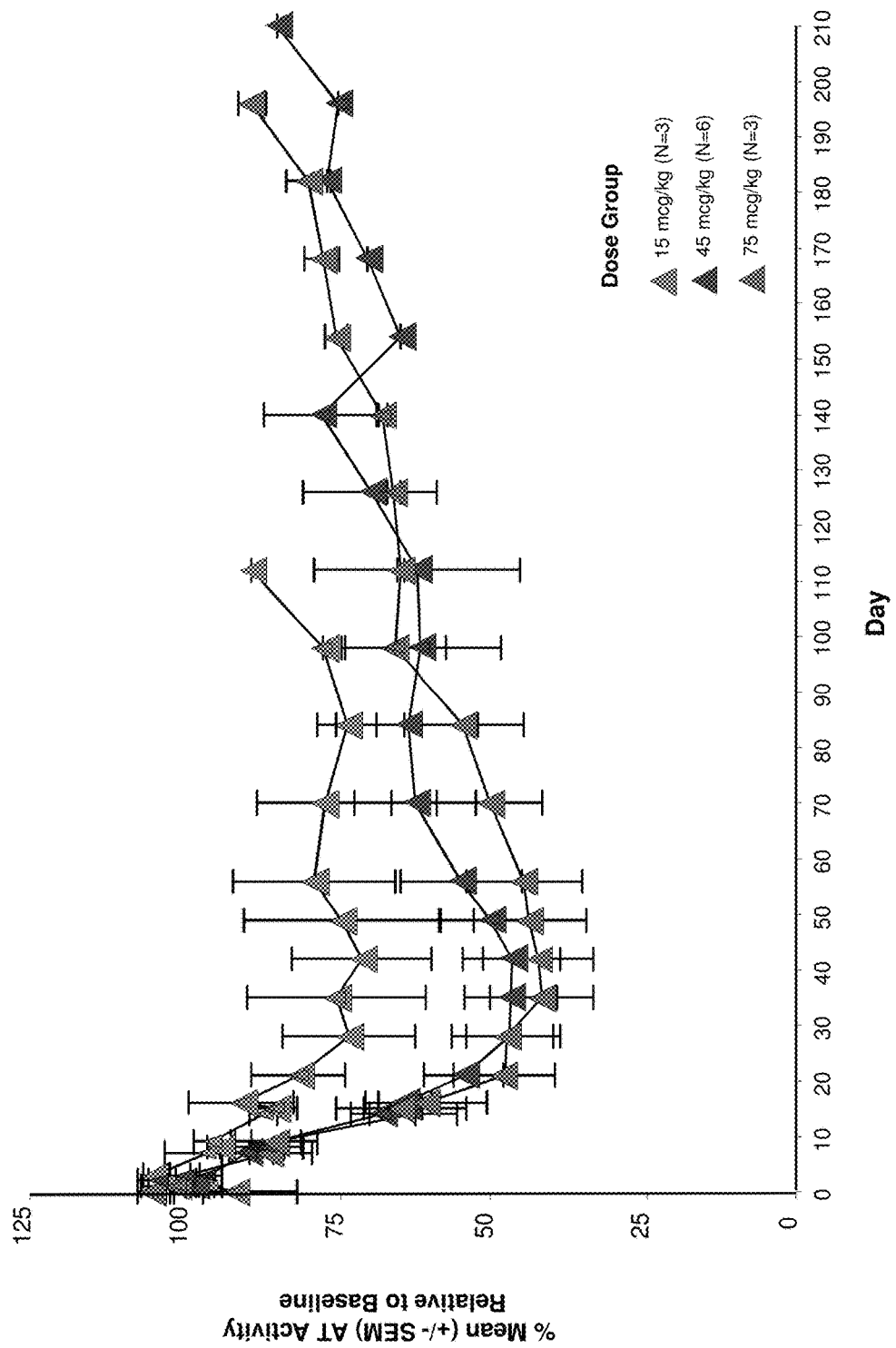
FIG. 4 is a graph depicting the effect of multiple 0.015 mg/kg, 0.045 mg/kg, or 0.075 mg/kg doses of AD-57213 on plasma AT (Serpinc1) protein levels in human subjects having Hemophilia A or B.

The knockdown of AT levels in the 15 mcg/kg, 45 mcg/kg, and 75 mcg/kg cohorts, shown as a mean AT knockdown relative to baseline, is depicted in FIG. 4. FIG. 4 demonstrates that weekly doses of 0.015 mg/kg for three weeks of AD-57213 result in a mean maximum AT knockdown of 29%±12% (mean±SEM). The maximum AT knockdown was up to 53%. FIG. 4 also demonstrates that weekly doses of 0.045 mg/kg for three weeks of AD-57213 results in a mean maximum AT knockdown of 55±9% (mean±SEM) and a maximum AT knockdown of 86%. In addition, FIG. 4 also demonstrates that weekly doses of 0.075 mg/kg for three weeks of AD-57213 results in a mean maximum AT knockdown of 61±8% (mean±SEM) and a maximum AT knockdown of 74%.

Figure 5A:
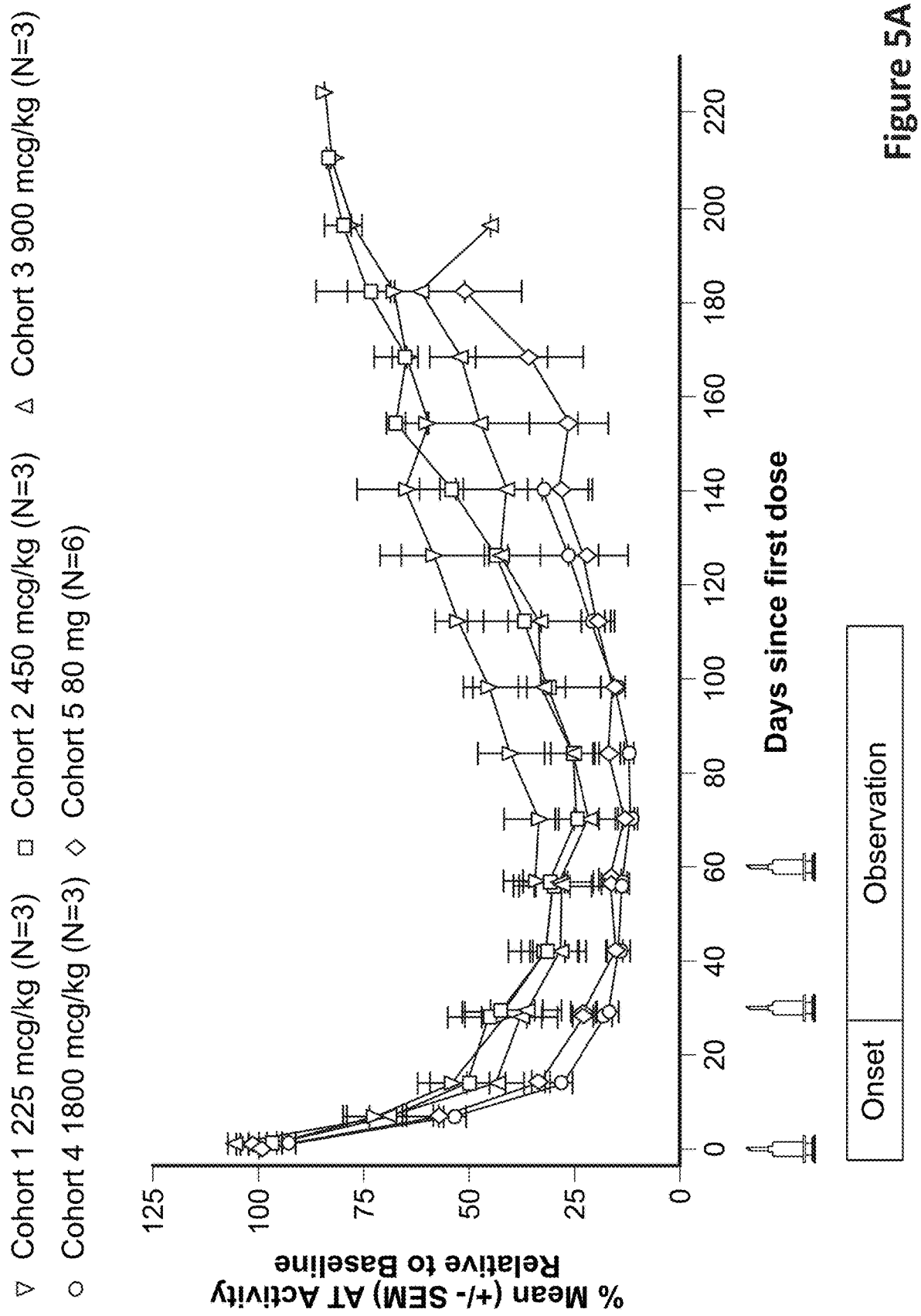
FIG. 5A is a graph depicting the effect of multiple 0.225 mg/kg, 0.450 mg/kg, 0.900 mg/kg, 1.800 mg/kg, or 80 mg doses of AD-57213 on plasma AT (Serpinc1) protein levels in human subjects having Hemophilia A or B.

The knockdown of AT levels in the 225 mcg/kg, 450 mcg/kg, 900 mcg/kg, 1800 mcg/kg, and 80 mg cohorts, shown as a mean AT knockdown relative to baseline, is depicted in FIG. 5A. FIG. 5A demonstrates that monthly doses of 0.225 mg/kg for three months of AD-57213 result in a mean maximum AT knockdown of 70%±9% (mean±SEM). The maximum AT knockdown was up to 80%. FIG. 5A also demonstrates that monthly doses of 0.450 mg/kg for three months of AD-57213 results in a mean maximum AT knockdown of 77±5% (mean±SEM) and a maximum AT knockdown of 85%. In addition, FIG. 5A also demonstrates that monthly doses of 0.900 mg/kg for three months of AD-57213 results in a mean maximum AT knockdown of 78±7% (mean±SEM) and a maximum AT knockdown of 88%. Further, FIG. 5A demonstrates that monthly doses of 1.800 mg/kg for three months of AD-57213 results in a mean maximum AT knockdown of 79±3% (mean±SEM) and a maximum AT knockdown of 84%. FIG. 5A also demonstrates that monthly doses of 80 mg for three months of AD-57213 results in a mean maximum AT knockdown of 87±1% (mean±SEM).

Figure 5B:
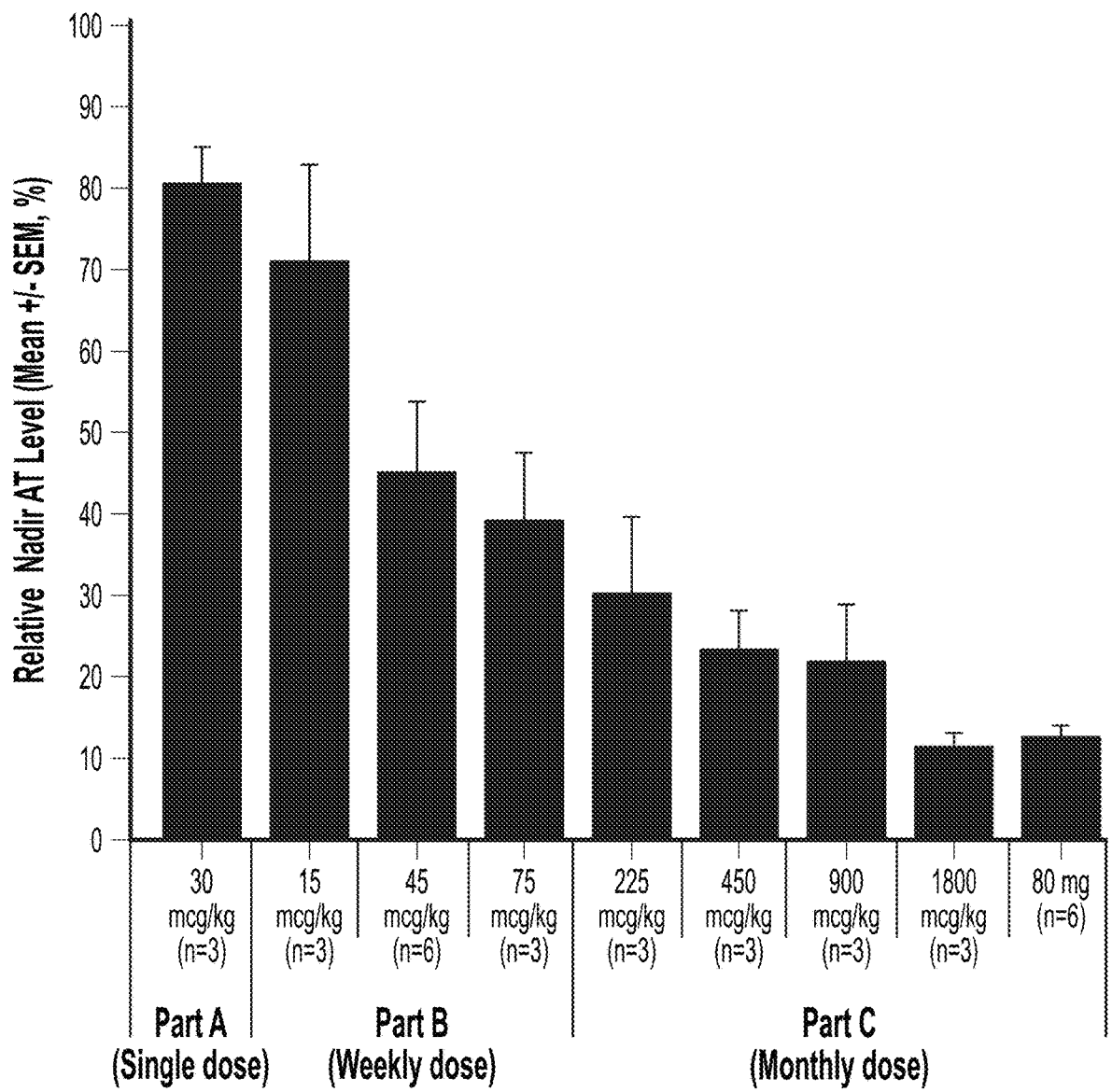
FIG. 5B is a graph depicting the dose dependent effect of AD-57213 on plasma AT (Serpinc1) protein levels in human subjects.
Figures 6A, 6B:
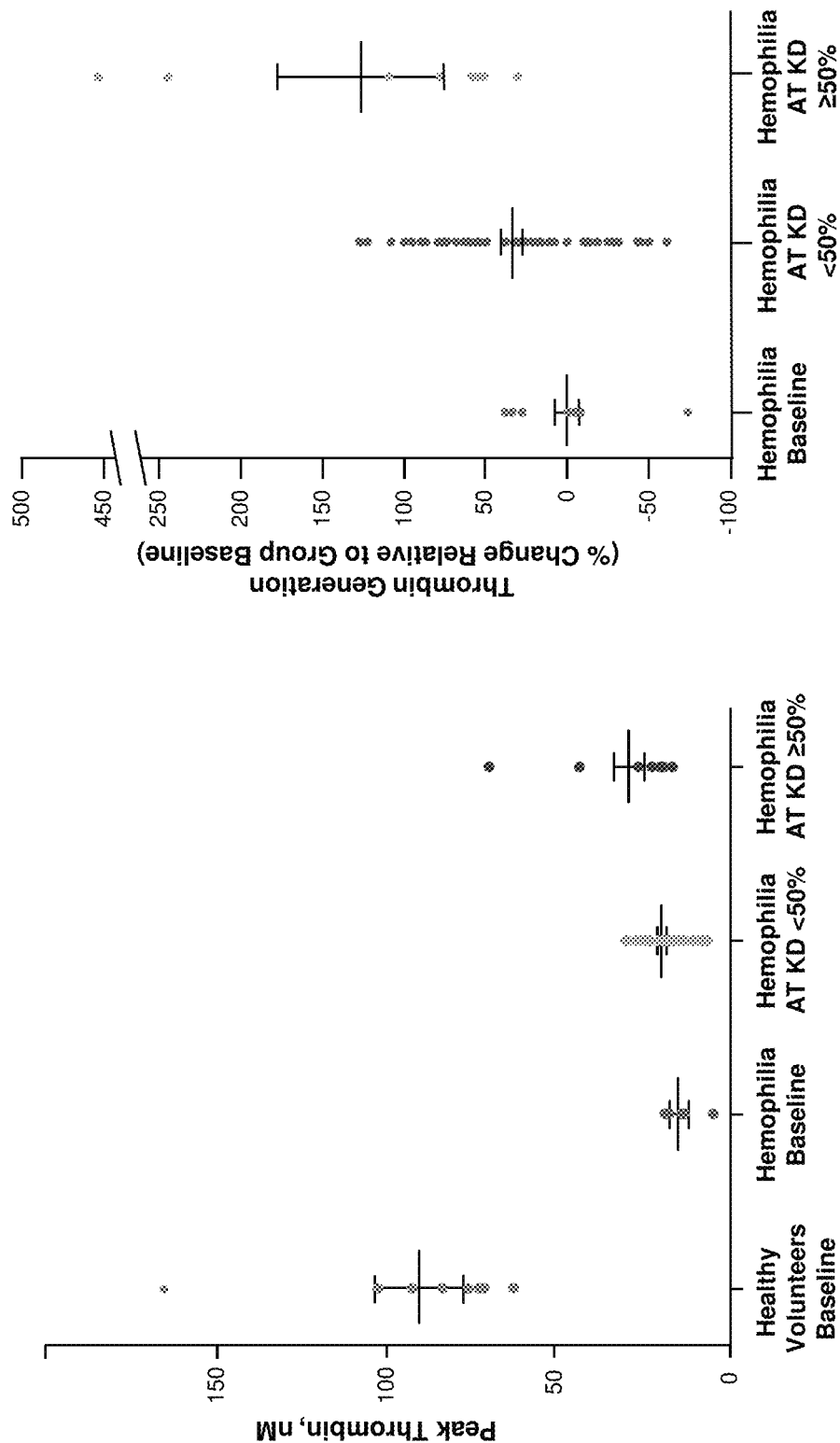
FIG. 6A is a graph depicting the effect of multiple 0.015 mg/kg or 0.045 mg/kg doses of AD-57213 on peak thrombin levels in human subjects having Hemophilia A or B.
FIG. 6B is a graph depicting the effect of multiple 0.015 mg/kg or 0.045 mg/kg doses of AD-57213 on thrombin generation as a percent change relative to group baseline in human subjects having Hemophilia A or B.

As demonstrated in FIG. 5B, which graphs the dose of AD-57213 versus the relative nadir of AT protein levels, administration of AD-57213 to human patients lowers AT protein levels in a dose dependent manner Evaluation of thrombin generation in healthy human volunteers (Example 1) and patients having hemophilia A or B demonstrated that weekly doses of AD-57213 resulted in up to a 334% increase (relative to baseline) in thrombin generation in hemophilia patients with a mean increase in thrombin generation of 112±38% (p<0.05), relative to baseline when AT was knocked down by >50% (FIG. 6B). FIG. 6A demonstrates that the maximum peak thrombin achieved in hemophilia A or B patients administered weekly doses of AD-57213 was at the low range of thrombin generation in normal subjects.

Figure 7:
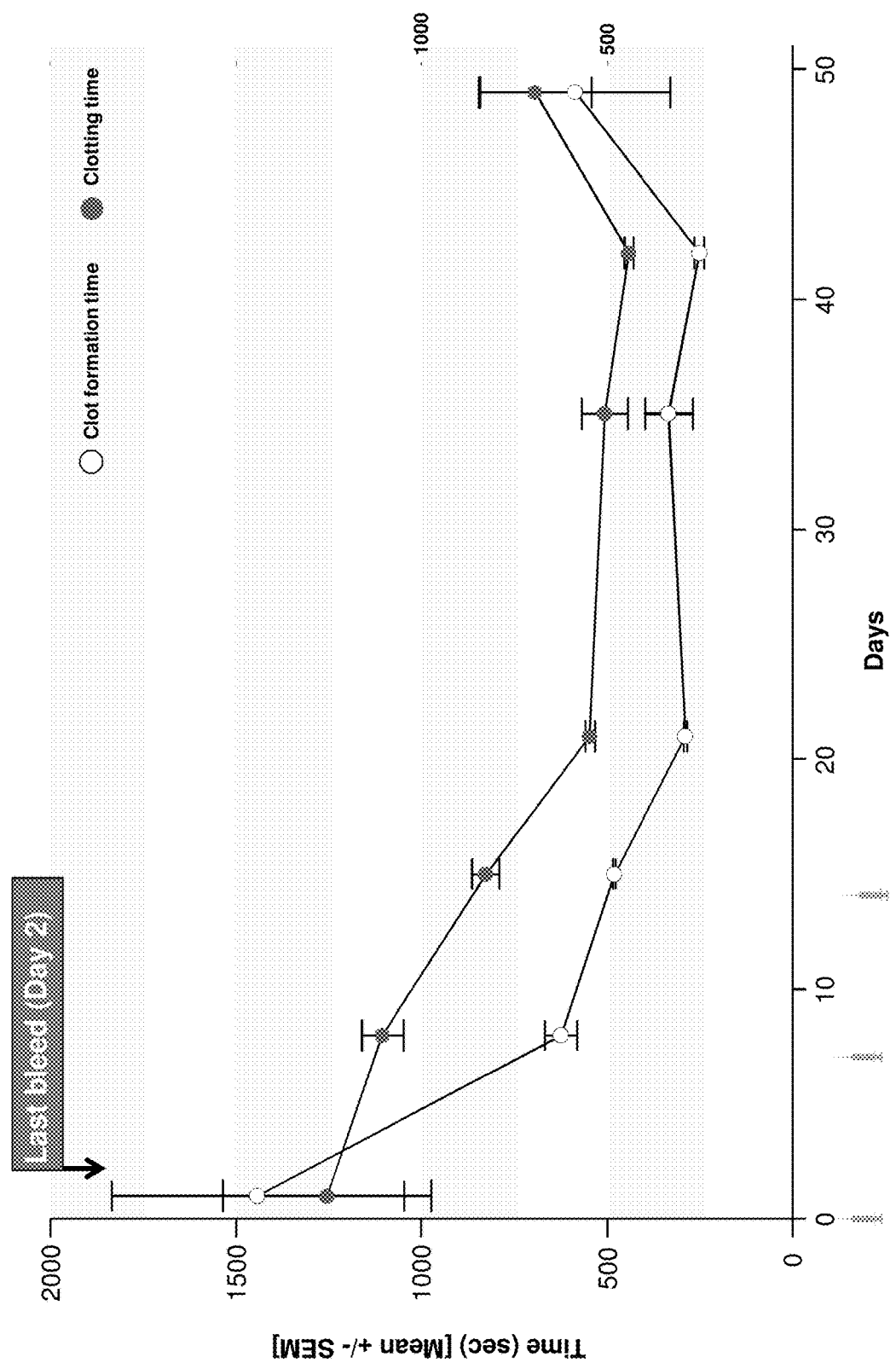
FIG. 7 is a graph depicting the effect of multiple 0.045 mg/kg doses of AD-57213 on clot formation time and clotting time in one subject having Hemophilia A (subject 101-009).
Figure 8:
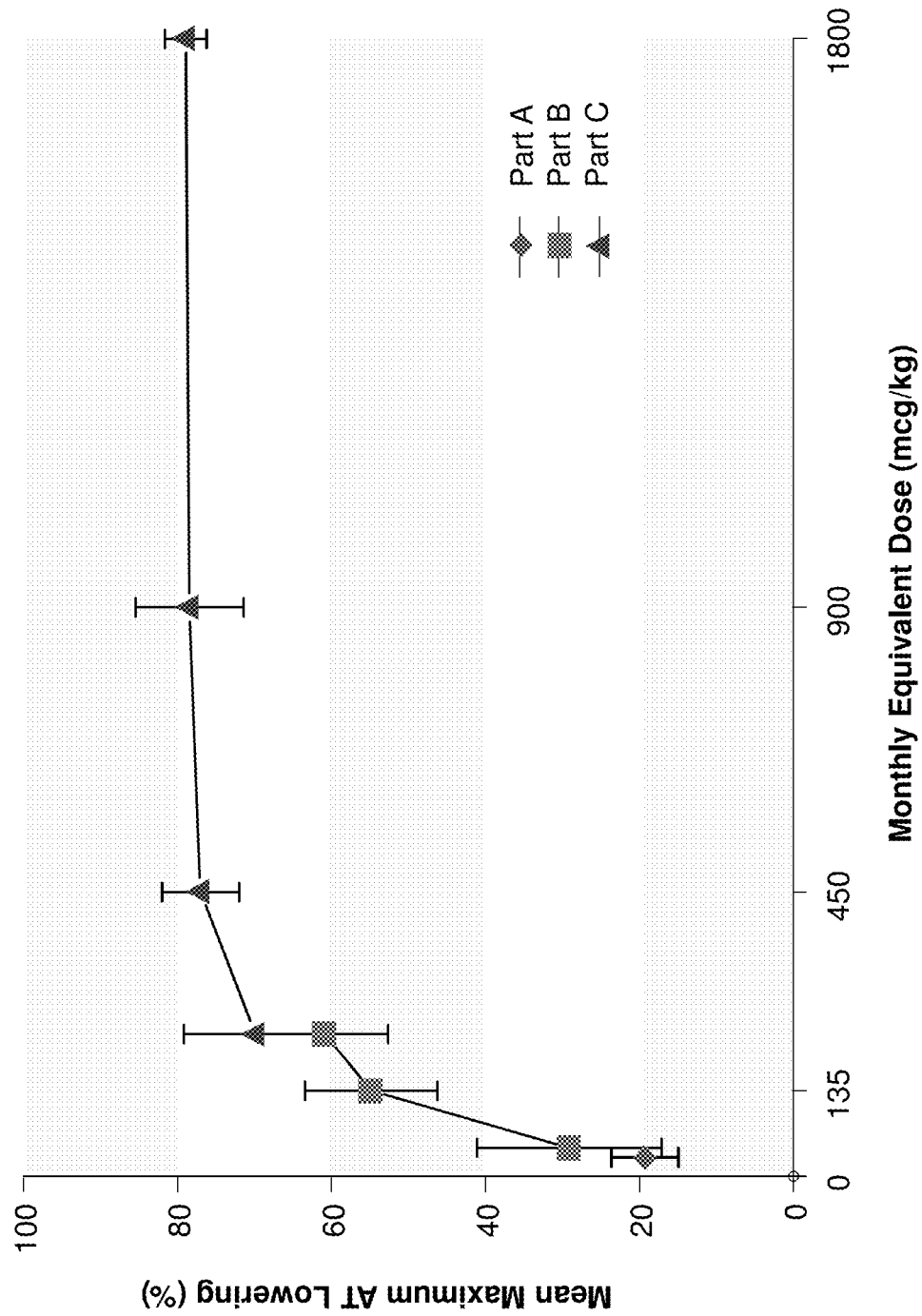
FIG. 8 is a graph depicting the mean maximum AT lowering by monthly equivalent dose.

ROTEM® Thromboelastometry analysis (see, e.g., Young, et al. (2013) Blood 121:1944) of whole blood from one subject (subject 101-009) demonstrates that administration of AD-57213 at 0.045 mg/kg weekly for three weeks not only results in an increase in peak thrombin generation, but also results in a marked and durable improvement in whole blood clot formation as demonstrated by a decrease in clot formation time and clotting time (FIG. 7). Subject 101-009 has had no bleeding events since day 2 and is currently 47 days bleed free.

Figure 9:
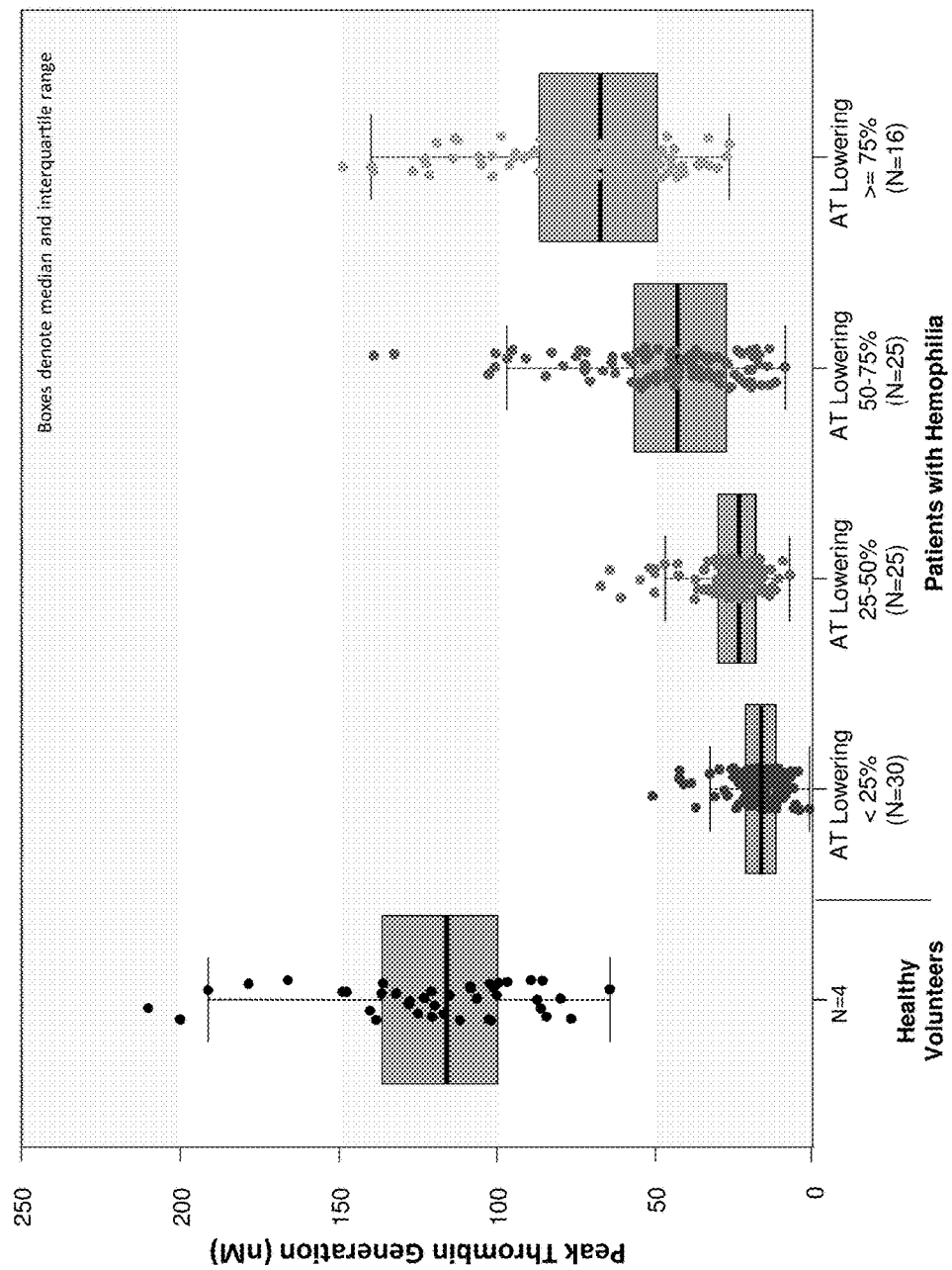
FIG. 9 is a graph depicting the effect of multiple doses of AD-57213 on thrombin generation by AT lowering quartiles.

A post-hoc analysis of thrombin generation by AT lowering quartiles (Parts B and C) demonstrates that, at the highest AT lowering quartile (>75% AT lowering), there is a 289% increase in mean thrombin generation relative to baseline (FIG. 9). This level of thrombin generation is within the range of thrombin generation observed in healthy volunteers.

Figures 10A, 10B:
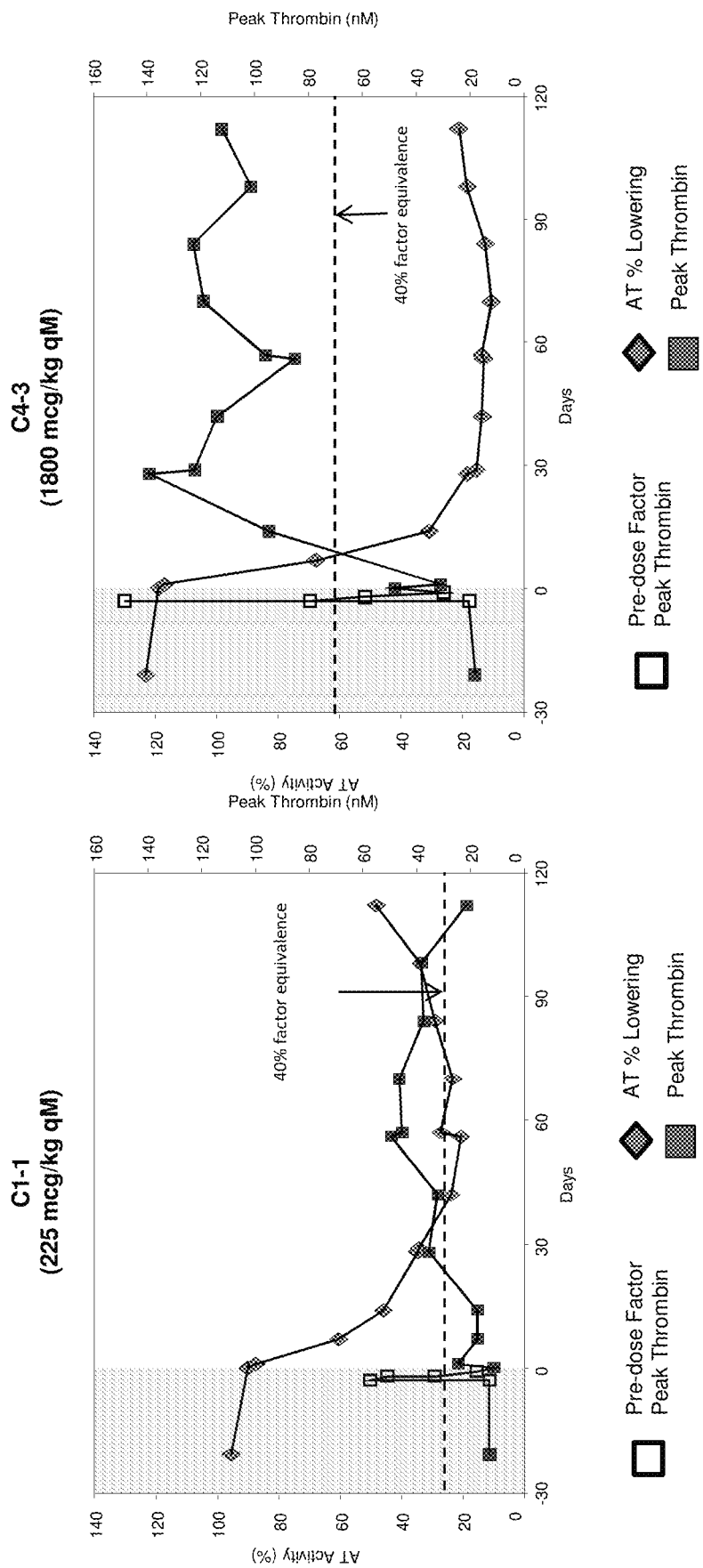
FIG. 10A is a graph depicting the relative AT activity in relation to the percent peak thrombin generation achieved with Factor VIII as determined in a subject administered 225 mcg/kg qM of AD-57213.
FIG. 10B is a graph depicting the relative AT activity in relation to the percent peak thrombin generation achieved with Factor VIII as determined in a subject administered 1800 mcg/kg qM of AD-57213.
Figure 10C:
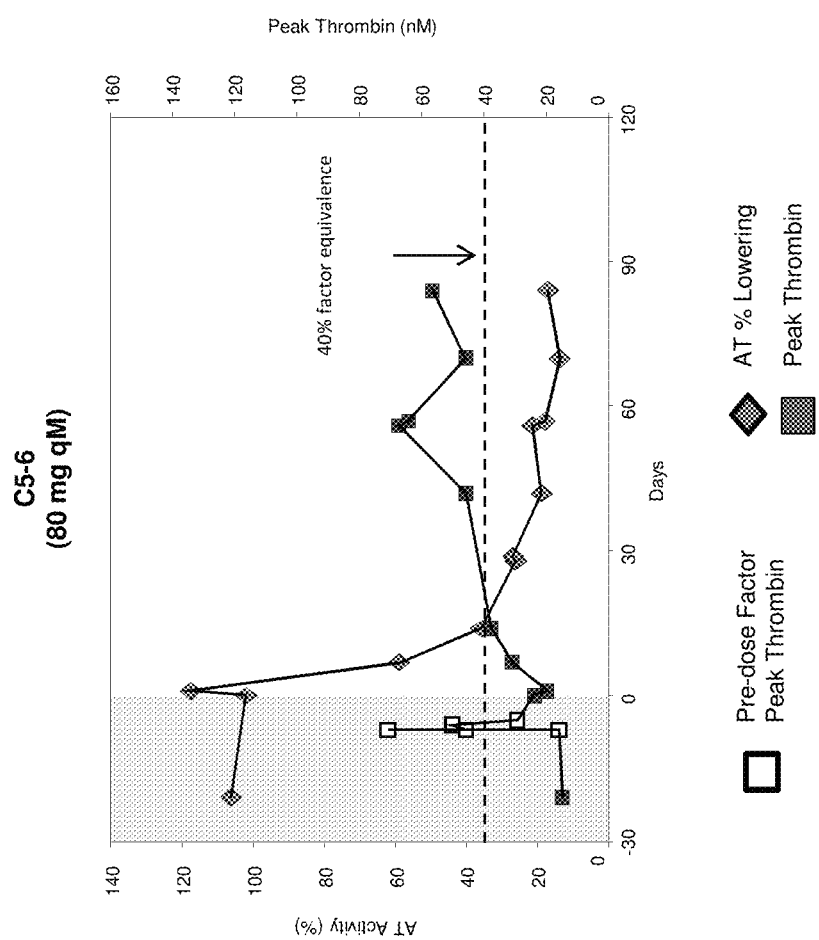
FIG. 10C is a graph depicting the relative AT activity in relation to the percent peak thrombin generation achieved with Factor VIII as determined in a subject administered 80 mg qM of AD-57213.

A sub-study of three patients explored the equivalence of AD-57213 administration and Factor VIII administration. Briefly, Factor VIII was administered to each of the three patients and plasma was collected from the patients at −0.5, 1, 2, 6, 24, and 48 hours post-administration. The samples from each subject were analyzed for Factor VIII levels and thrombin generation levels and used to establish individualized Factor VIII-peak thrombin generation relationships. This data was then used for comparison with the peak thrombin generation levels achieved with administration of AD-57213. As shown in FIGS. 10A-10C, administration of AD-57213 is sufficient to achieve peak thrombin generation levels in the subject to about the same level achieved by administration to the subject of Factor VIII and sufficient to achieve peak thrombin generation levels of greater than about 40% in the subject.

Figure 11:
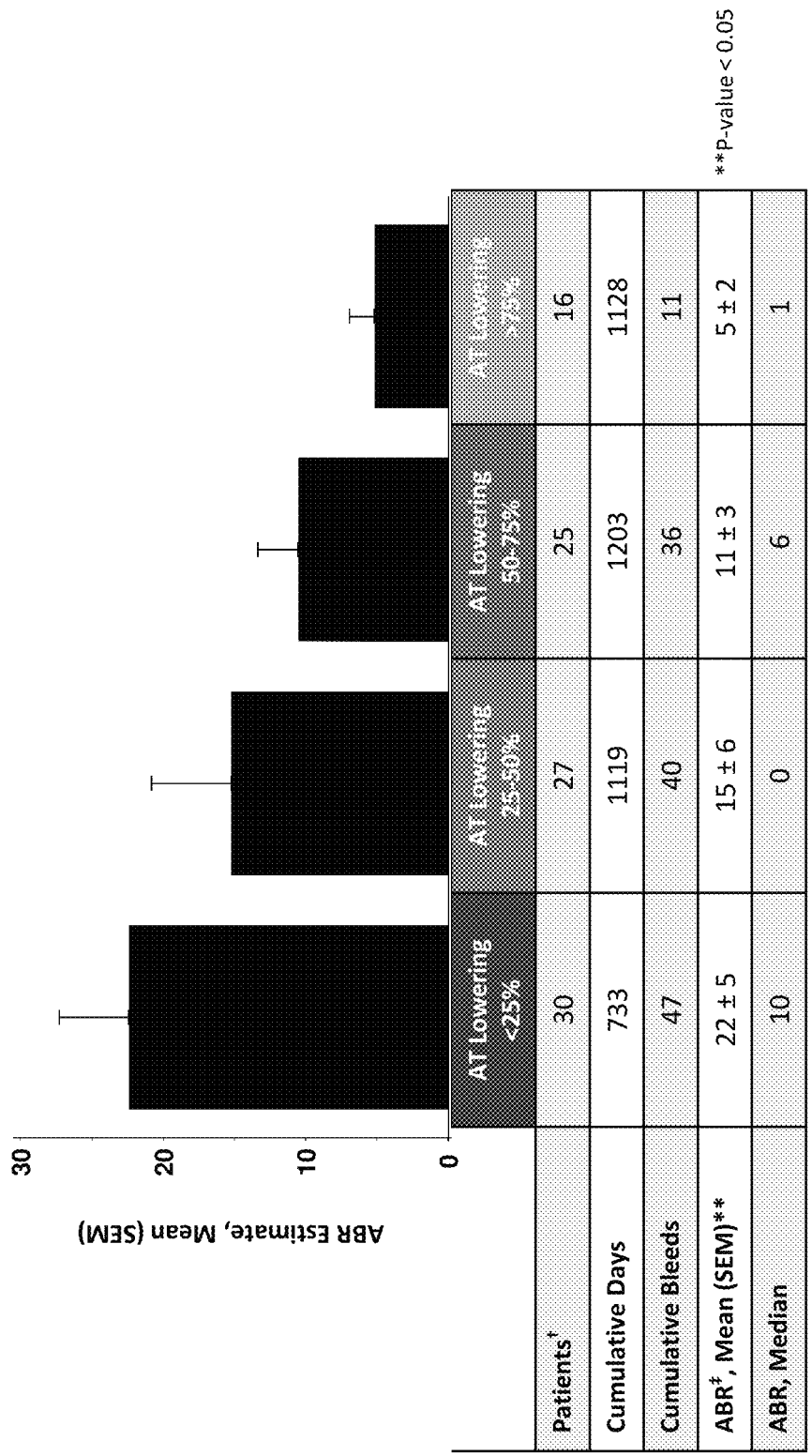
FIG. 11 is a graph depicting the effect of multiple doses of AD-57213 on bleed events by AT lowering quartiles.

A post-hoc analysis of the bleed events by AT lowering quartile (Parts B and C) demonstrates that there is a reduced bleeding tendency with increasing levels of AT lowering, with a mean estimated annual bleed rate (ABR) of 5±2 (median=1) in the highest AT lowering quartile (FIG. 11). This analysis includes more than 1100 cumulative days with AT lowering>75% in 16 patients.

Figure 13B:
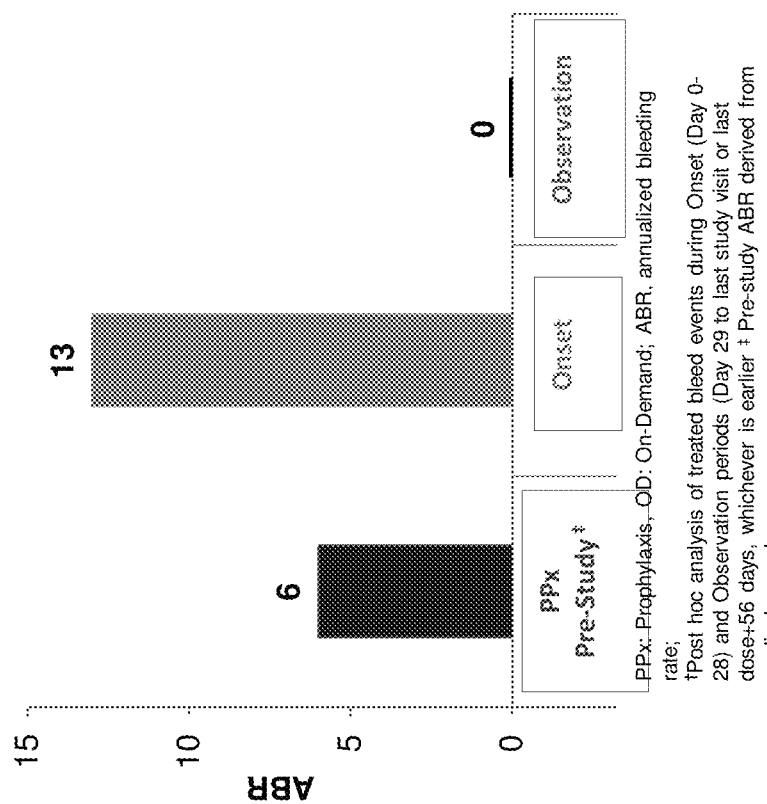
FIG. 13B is a graph showing the median annual bleed rate (ABR) prior to the initiation of the study, at the onset portion of the study, and during the observation portion of the study for the monthly 80 mg (80 mg qM×3) cohort in Part C of the Phase I clinical trial of AD-57213.
Figure 13A:
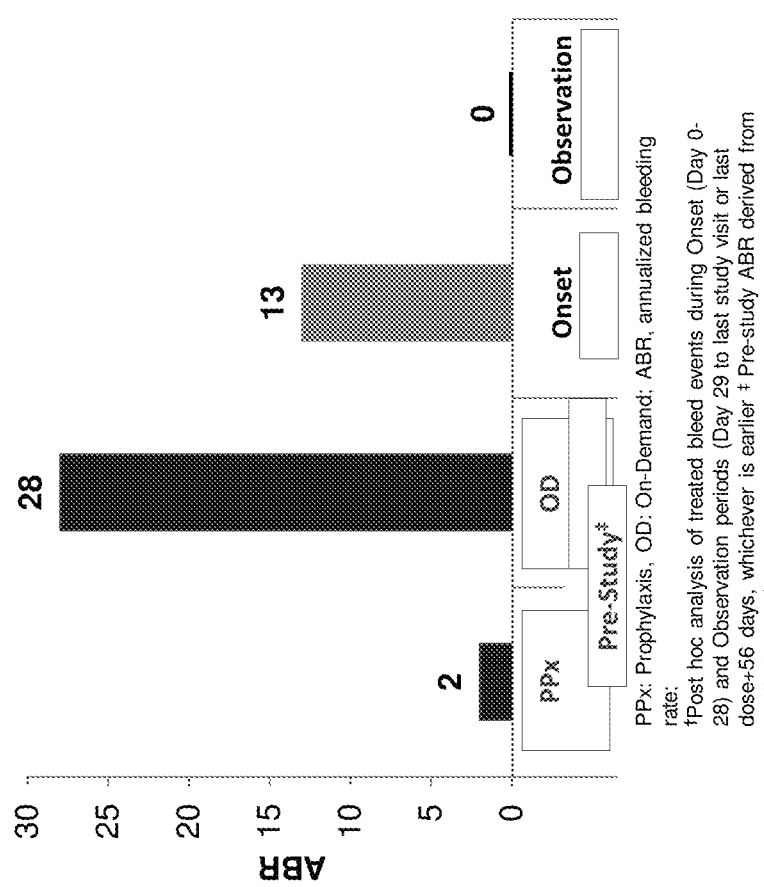
FIG. 13A is a graph showing the median annual bleed rate (ABR) prior to the initiation of the study, at the onset portion of the study, and during the observation portion of the study for all of the dosing cohorts in Part C of the Phase I clinical trial of AD-57213.
Figures 14C, 14D:
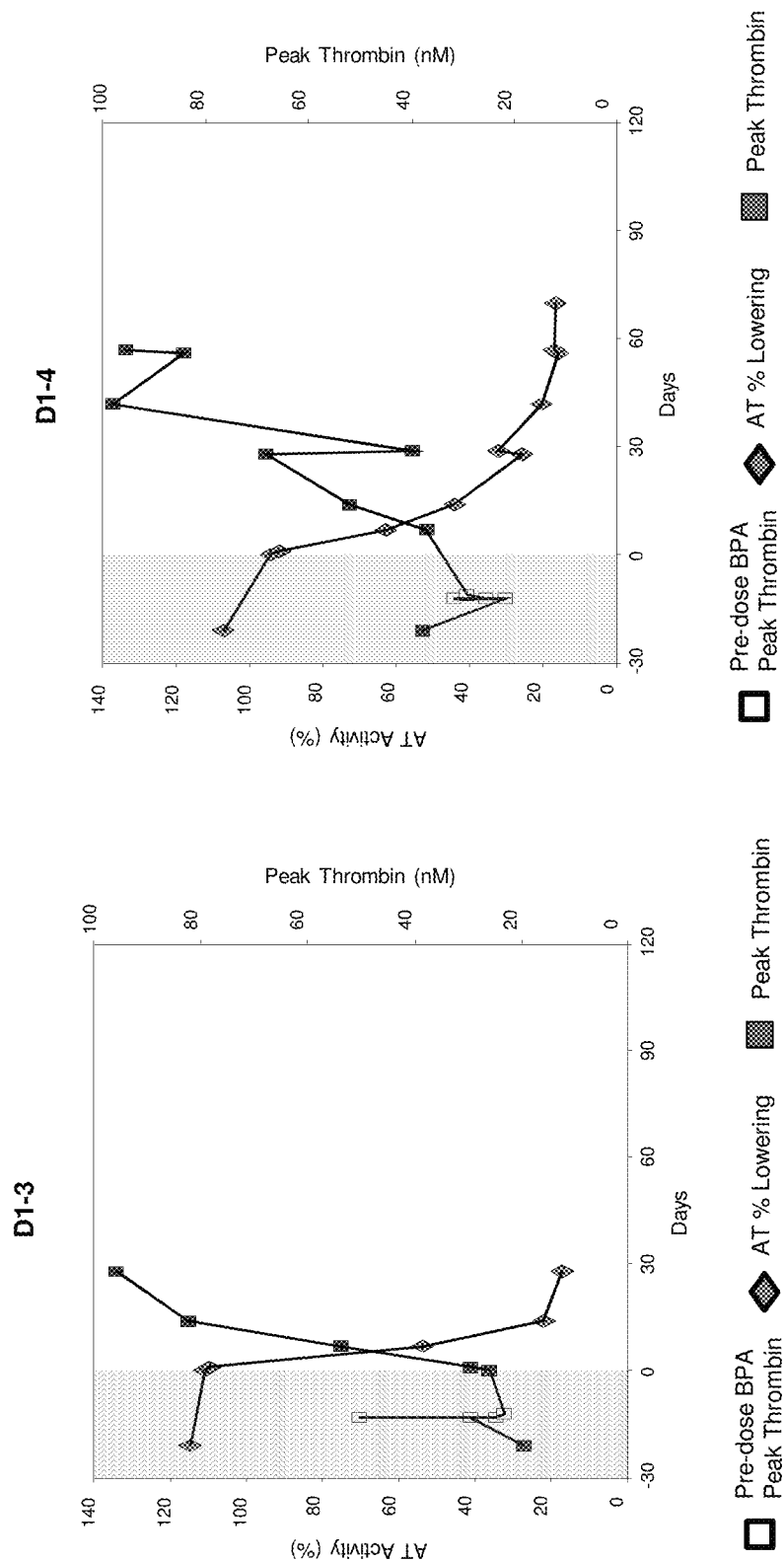
FIG. 14C is a graph depicting the relative AT activity in relation to the percent peak thrombin generation achieved with Factor VIII as determined in an inhibitor subject administered a fixed monthly 50 mg dose of AD-57213.
FIG. 14D is a graph depicting the relative AT activity in relation to the percent peak thrombin generation achieved with Factor VIII as determined in an inhibitor subject administered a fixed monthly 50 mg dose of AD-57213.
Figures 14E, 14F:
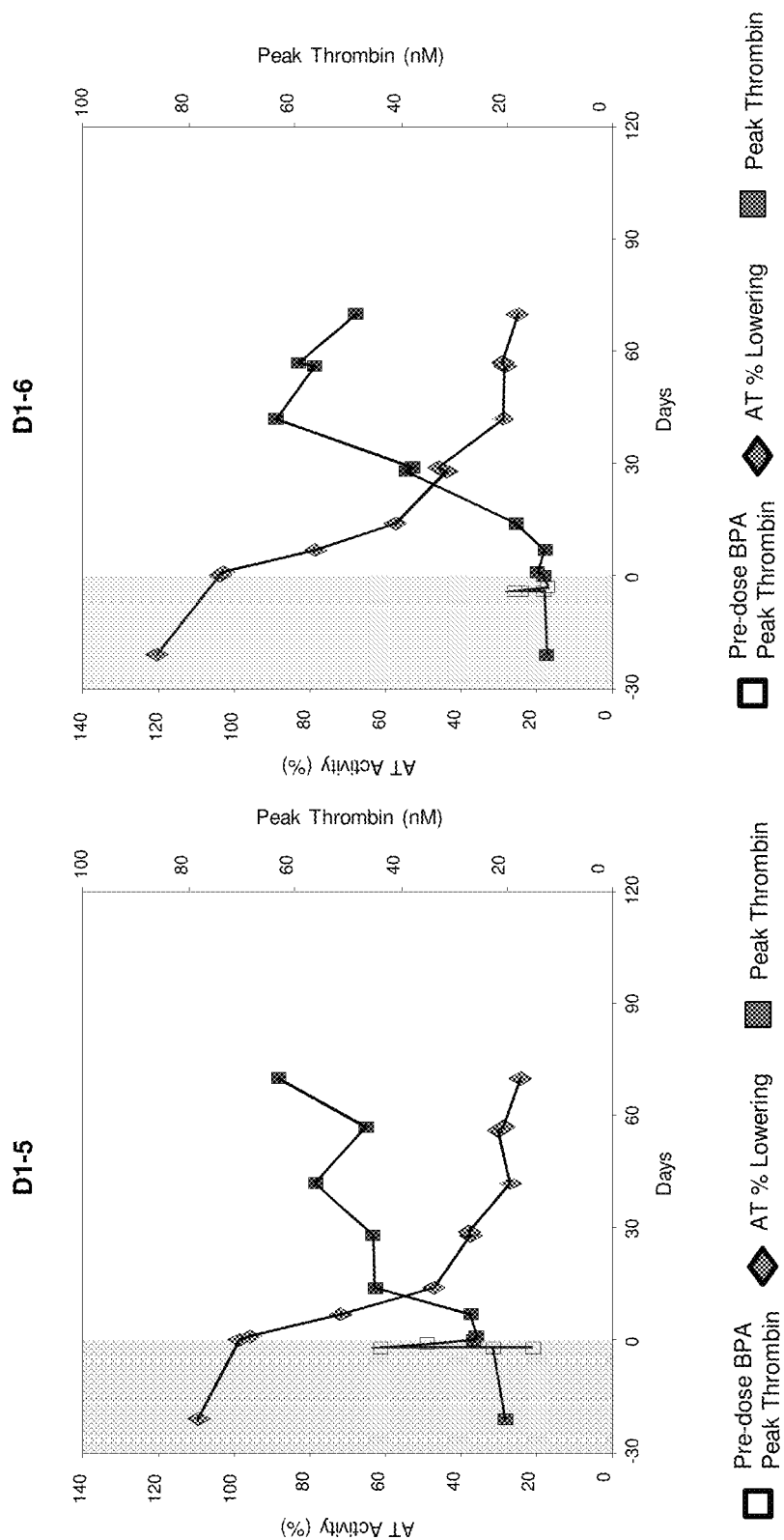
FIG. 14E is a graph depicting the relative AT activity in relation to the percent peak thrombin generation achieved with Factor VIII as determined in an inhibitor subject administered a fixed monthly 50 mg dose of AD-57213.
FIG. 14F is a graph depicting the relative AT activity in relation to the percent peak thrombin generation achieved with Factor VIII as determined in an inhibitor subject administered a fixed monthly 50 mg dose of AD-57213.

A post-hoc analysis of the bleed events in the Part C cohort was also performed. FIG. 12 provides the patient data used for this analysis. As demonstrated in FIG. 13A, the historical median ABR for all of the patients enrolled in Cohort C and receiving prophylactic (PPx) replacement factors was 2, and the historical median ABR for all of the patients enrolled in Cohort C and receiving on-demand (OD) replacement factors was 28. Administration of AD-57213 to these patients resulted in a significant reduction in the median ABR. In particular, AD-57213 administration resulted in a median of 53% of the patients reporting no bleeds during the observation period (day 29 to the last study visit or last dose+56 days, which ever is earlier) and a median of 82% of the patients reporting no spontaneous bleeds during the observation period. FIG. 13B demonstrates that for the patients receiving monthly 80 mg doses of AD-57213 in Cohort C and receiving prophylactic (PPx) replacement factors, the median historical ABR was 6. Following administration of AD-57213, however, the median ABR during the observation period was 0.

Part D of the Phase I study evaluated the effect of AD-57213 administration in patients having Hemophilia A or B which have developed antibodies (inhibitors) against the replacement factors given to them and have, thus, become refractory to replacement coagulation factor. Accordingly, in order to evaluate the peak thrombin response of these patients, prior to administration of AD-57213, the patients enrolled in the 50 mg cohort were administered their standard bypassing agent (BPA) (e.g., activated prothrombin complex concentrate (APCC) and/or recombinant activated FVII (rFVIIa)), plasma samples were collected at −1, 2, 6, and 24 hours post BPA administration, and the samples were analyzed for thrombin generation. As shown in FIGS. 14A-14F, AT lowering and thrombin generation in inhibitor patients administered AD-57213 are comparable to AT lowering and thrombin generation observed following administration of AD-57213 with similar doses in non-inhibitor patients. Furthermore, FIGS. 14A-14F demonstrate that thrombin generation following administration of AD-57213 consistently exceeds transient levels achieved with BPA administration.

Figure 15:
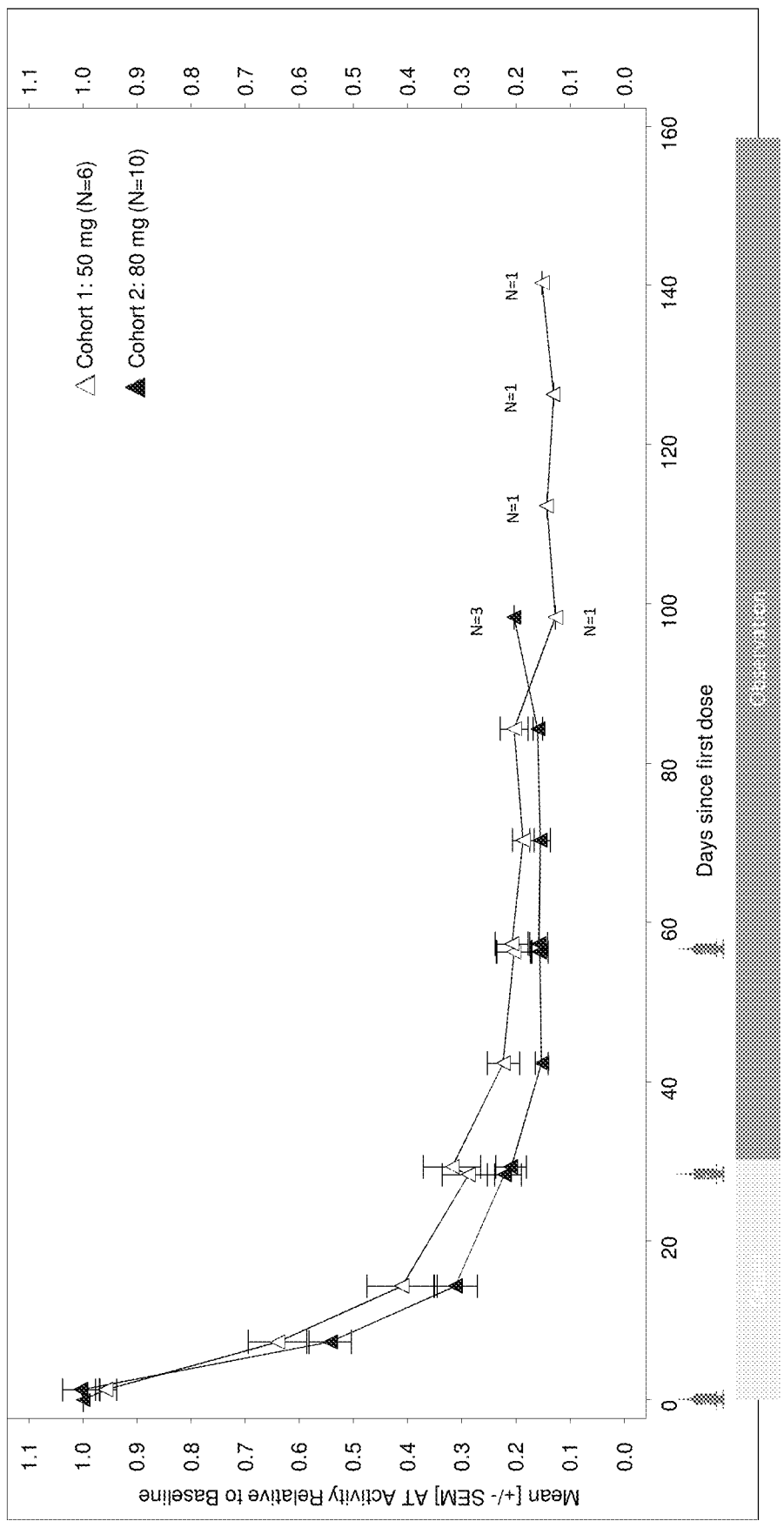
FIG. 15 is a graph depicting the effect of multiple 50 mg or 80 mg doses of AD-57213 on the mean AT (Serpinc1) activity relative to baseline in human subjects having Hemophilia A or B with inhibitors.
Figure 16:
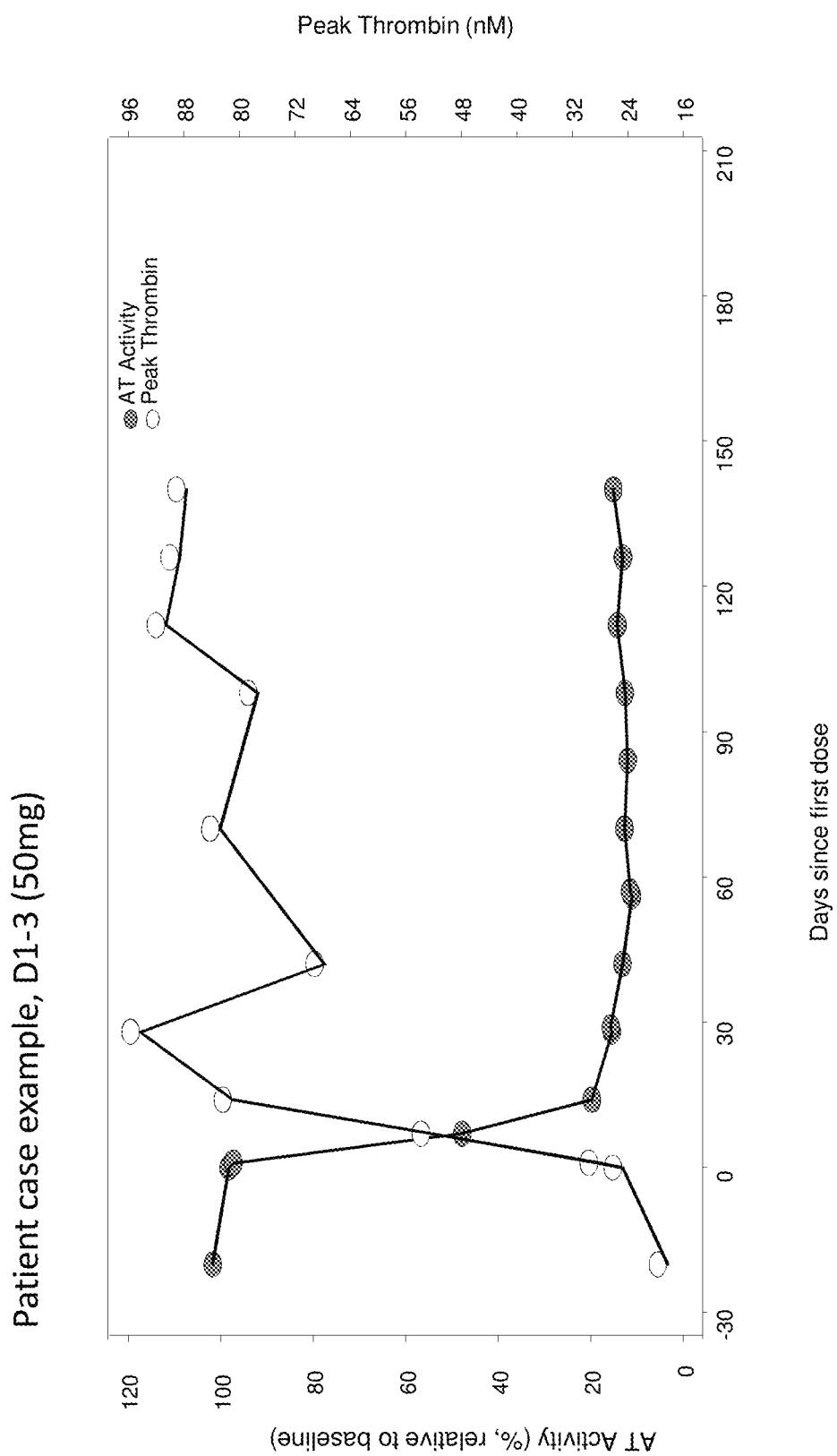
FIG. 16 is a graph depicting that the AT lowering effect of multiple 50 mg doses of AD-57213 correlates with increased thrombin generation in a subject having Hemophilia A.

As demonstrated in FIG. 15, once-monthly subcutaneous dosing of AD-57213 at 50 mg and 80 mg achieves dose-dependent AT lowering of about 80% in hemophilia patients with inhibitors. Furthermore, as demonstrated in FIG. 16, the AT lowering effect achieved in patients administered AD-57213 is correlated with increased thrombin generation.

Figure 17B:
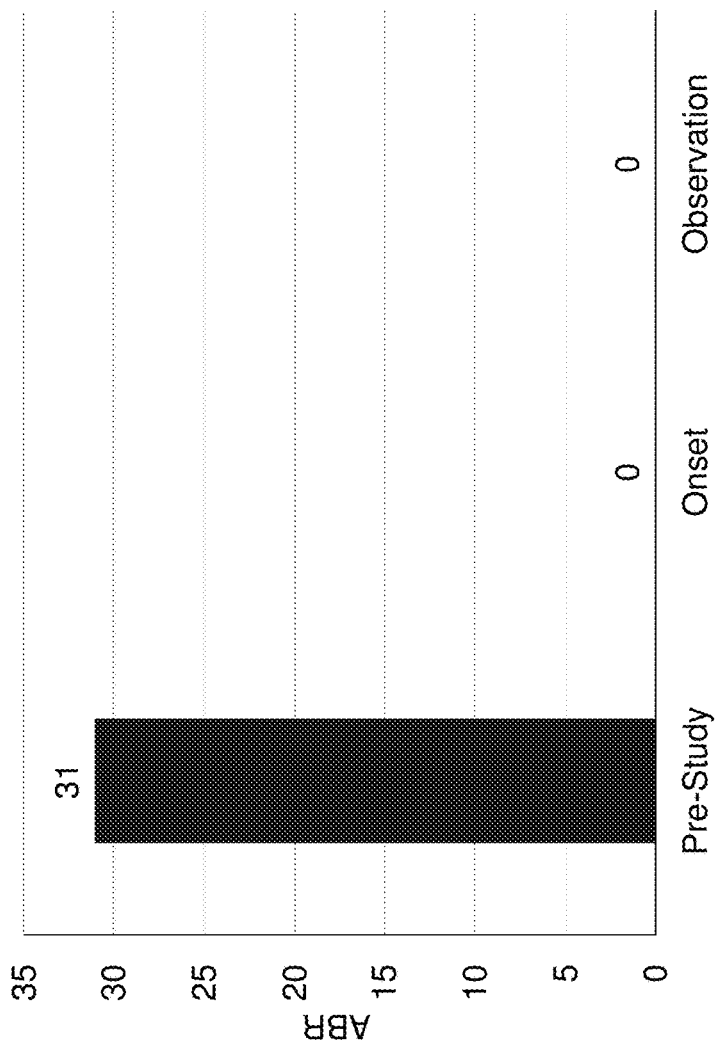
FIG. 17B is a graph showing the median annual bleed rate (ABR) prior to the initiation of the study, at the onset portion of the study, and during the observation portion of the study for all of the subjects in Part D of the Phase I clinical trial of AD-57213.
Figure 18:
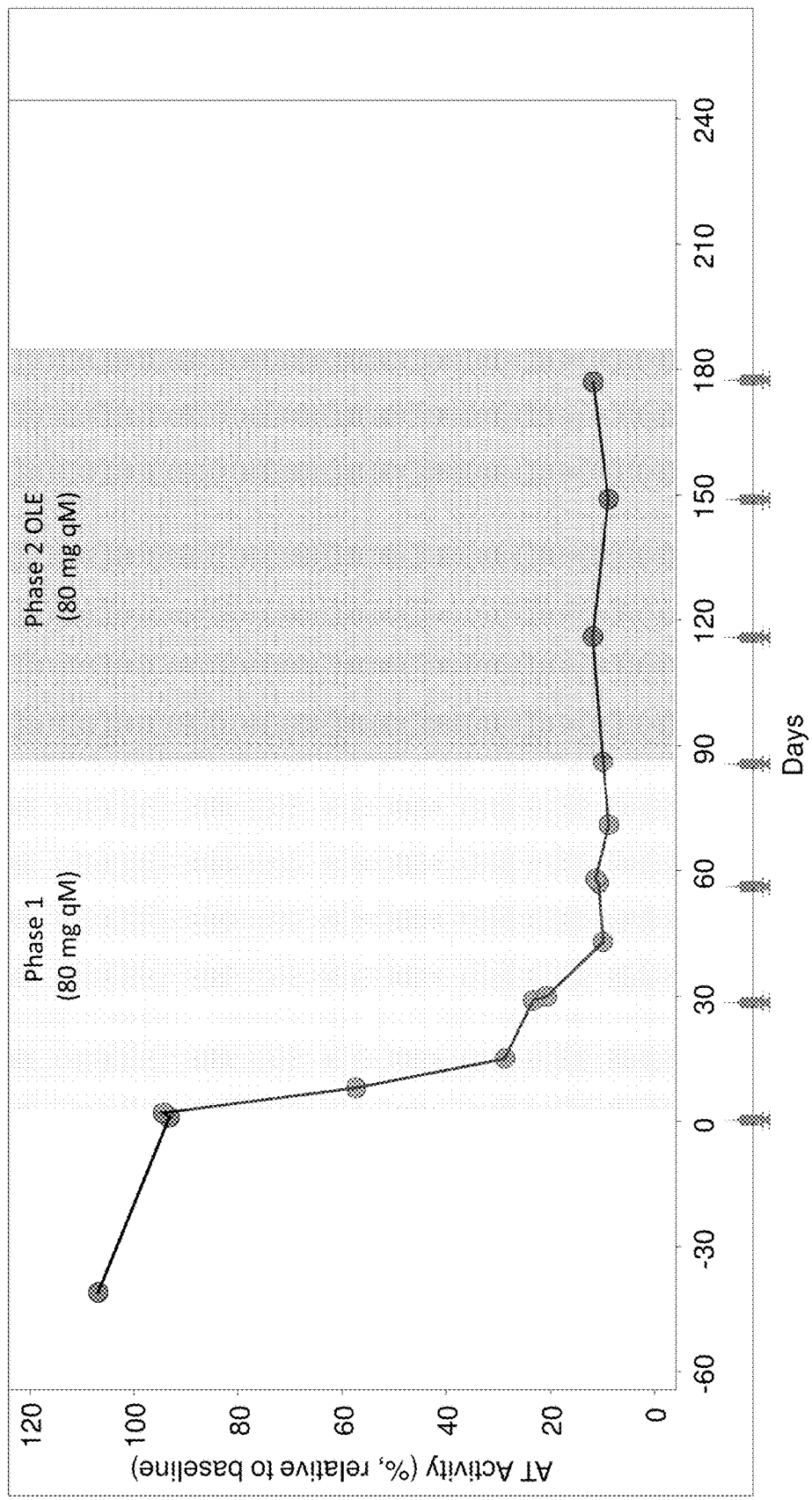
FIG. 18 is a graph depicting the effect of multiple 80 mg doses of AD-57213 on the mean AT (Serpinc1) activity relative to baseline in a human subject having Hemophilia without inhibitors in the Phase II open label extension (OLE) study of AD-57213.

An exploratory post-hoc analysis of the bleed events in the patients in Part D of the study was also performed. FIG. 17A shows that administration of AD-57213 to inhibitor patients having Hemophilia A or B once monthly at a dose of either 50 mg or 80 mg results in a significant reduction in the pre-study ABR. Furthermore, as demonstrated in FIG. 17B, the median annual bleed rate (ABR) is zero for all inhibitor patients administered AD-57213 in Part D of this Phase I study, and 56% of patients are bleed-free, and 69% of patients experienced zero spontaneous bleeds.

In summary, AD-57213 is well tolerated in hemophilia A and B patients with and without inhibitors. There were no SAEs related to study drug and no thromboembolic events. The data demonstrate that there is clinical activity and correction of hemophilia phenotype in non-inhibitor patients. The data further demonstrate that there is dose-dependent AT lowering and thrombin generation increase, with once-monthly subcutaneous dose regimen and that administration of a fixed 50 mg or 80 mg dose of AD-57213 provides consistent AT lowering of approximately 80%.

Furthermore, the data demonstrate that administration of AD-57213 to inhibitor patients results in AT lowering and thrombin generation increase consistent with non-inhibitor patients and that thrombin generation increases consistently exceed those achieved transiently with BPA administration.

Example 3: Administration of Multiple Doses of AD-57213 to Human Patients Having Hemophilia A or B Phase II Open Label Extension (OLE) Clinical Trial In a Phase II OLE study of AD-57213 (Sense (5' to 3'): GfsgsUfuAfaCfaCfCfAfuUfuAfcUfuCfaAfL96 (SEQ ID NO:13); Antisense (5' to 3'): usUfsgAfaGfuAfaAfuggUfgUfuAfaCfcsasg (SEQ ID NO:14)), patients without inhibitors previously administered AD-57213 in the Phase I Part B and C clinical trials described above, were eligible to be enrolled into a Phase II open-label extension (OLE) study. Twelve patients from the Phase I Part B study having Hemophilia A or B that had been subcutaneously administered 0.015 mg/kg weekly for three weeks (15 micrograms/kg qw×3; 15 mcg/kg) of AD-57213; or had been subcutaneously administered 0.045 mg/kg weekly for three weeks (45 micrograms/kg qw×3; 45 mcg/kg) of AD-57213; or had been subcutaneously administered 0.075 mg/kg weekly for three weeks (75 micrograms/kg qw×3; 75 mcg/kg) of AD-57213; and 18 patients from the Phase I Part C study having Hemophilia A or B that had been subcutaneously administered a monthly 0.225 mg/kg dose of AD-57213 for three months (225 micrograms/kg qm×3; 225 mcg/kg); or had been subcutaneously administered a monthly 0.450 mg/kg dose of AD-57213 for three months (450 micrograms/kg qm×3; 450 mcg/kg); or had been subcutaneously administered a monthly 0.900 mg/kg dose of AD-57213 for three months (900 micrograms/kg qm×3; 900 mcg/kg); or had been subcutaneously administered a monthly 1.800 mg/kg dose of AD-57213 for three months (1800 micrograms/kg qm×3; 1800 mcg/kg); or had been subcutaneously administered a monthly fixed dose of 80 mg of AD-57213 for three months (80 mg qM×3) were eligible to be enrolled into this study.

Sixteen patients were enrolled. Eight patients having Hemophilia A (n=6) or Hemophilia B (n=2) were subcutaneously administered a fixed dose of 50 mg of AD-57213 monthly for three months (50 mg qM×3); and 8 patients having Hemophilia A (n=7) or Hemophilia B (n=1) were subcutaneously administered a fixed dose of 80 mg of AD-57213 monthly for three months (50 mg qM×3). The demographics and baseline characteristics of the patients enrolled in this study are shown in Table 3 below.

TABLE 3

Demographics and baseline characteristics of study participants

|  | 50 mg<br>N = 8 | 80 mg<br>N = 8 |
|---|---|---|
| Age, years; mean (range) | 35<br>(19-61) | 41<br>(24-58) |
| Weight, kg; mean (range) | 80<br>(65-94) | 74<br>(58-80) |
| Hemophilia A | 6 | 7 |
| Hemophilia B | 2 | 1 |
| Severe | 7 | 6 |
| Moderate | 1 | 2 |
| Medical history of hepatitis C[†] | 6 | 6 |

AD-57213 was generally well tolerated in patients without inhibitors in the Phase II OLE, with the longest period of exposure of up to 14 months of continuous treatment, and there were no drug-related serious adverse events (SAEs), no discontinuations due to adverse events, and no thromboembolic events or laboratory evidence of pathologic clot formation. All adverse events (AEs) were mild or moderate in severity, with the most common AEs consisting of mild injection site reactions (ISRs) in 4/16 (25 percent) of patients. Asymptomatic alanine aminotransferase (ALT) increases greater than 3 times the upper limit of normal (ULN), without concurrent elevations in bilirubin greater than 2 times ULN, were observed in 3 patients, all of whom have a medical history of hepatitis C infection. All breakthrough bleeding events were successfully managed with replacement factor. Furthermore, there were no instances of anti-drug antibody (ADA) formation.

Figure 19B:
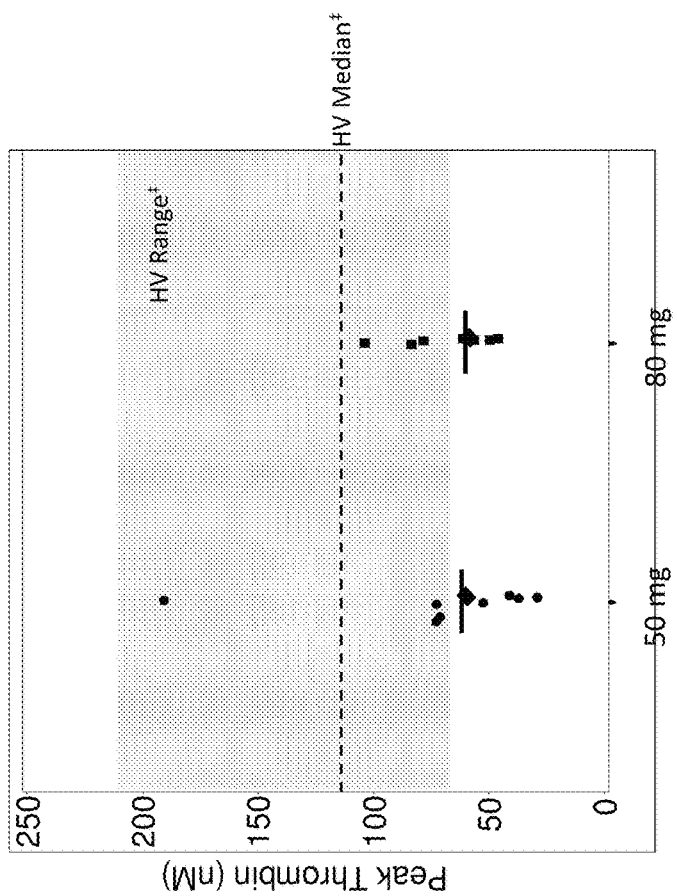
FIG. 19B is a graph depicting the effect of multiple 50 mg or 80 mg doses of AD-57213 on peak thrombin generation in human subjects having Hemophilia A or B without inhibitors in the Phase II open label extension (OLE) study of AD-57213. The shaded portion of the graph represents the range of peak thrombin levels observed in healthy human volunteers (HV) administered AD-57213 and with less than 25% AT knockdown in the Phase I trial of AD-57213 described in Example 1. The dashed line through the HV range represents the median peak thrombin level observed in healthy human volunteers (HV) and with less than 25% AT knockdown administered AD-57213 in the Phase I trial of AD-57213 described in Example 1.
Figure 19A:
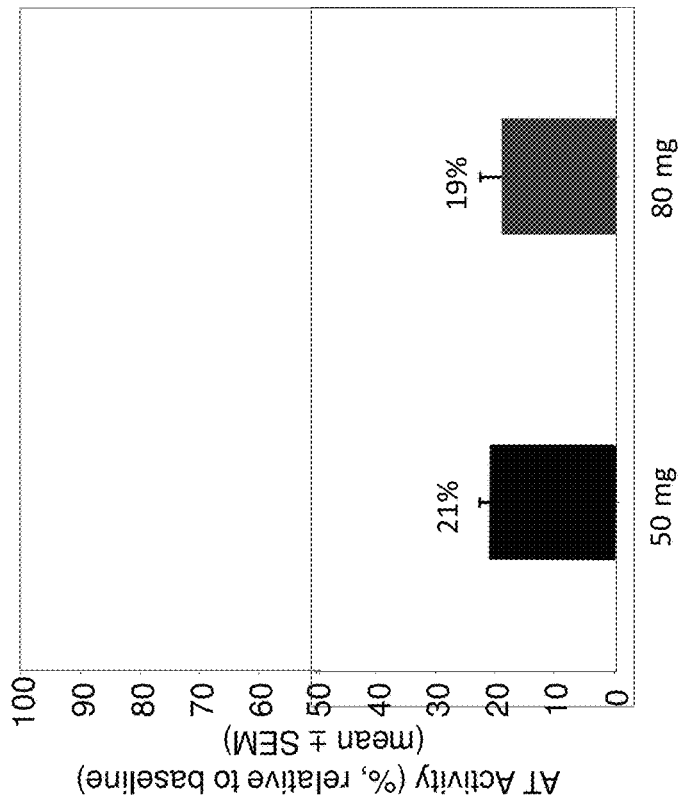
FIG. 19A is a graph depicting the effect of multiple 50 mg or 80 mg doses of AD-57213 on the mean AT (Serpinc1) activity relative to baseline in human subjects having Hemophilia A or B without inhibitors in the Phase II open label extension (OLE) study of AD-57213.

FIGS. 19A and 19B further demonstrate the clinical activity of AD-57213 administration. Specifically, as demonstrated in FIG. 19A, once-monthly subcutaneous dosing of AD-57213 at 50 mg or 80 mg achieves dose-dependent AT lowering of ~80% and as demonstrated in FIG. 19B, once-monthly subcutaneous dosing of AD-57213 at 50 mg or 80 mg achieves thrombin generation levels approaching the lower end of normal range.

Figure 20B:
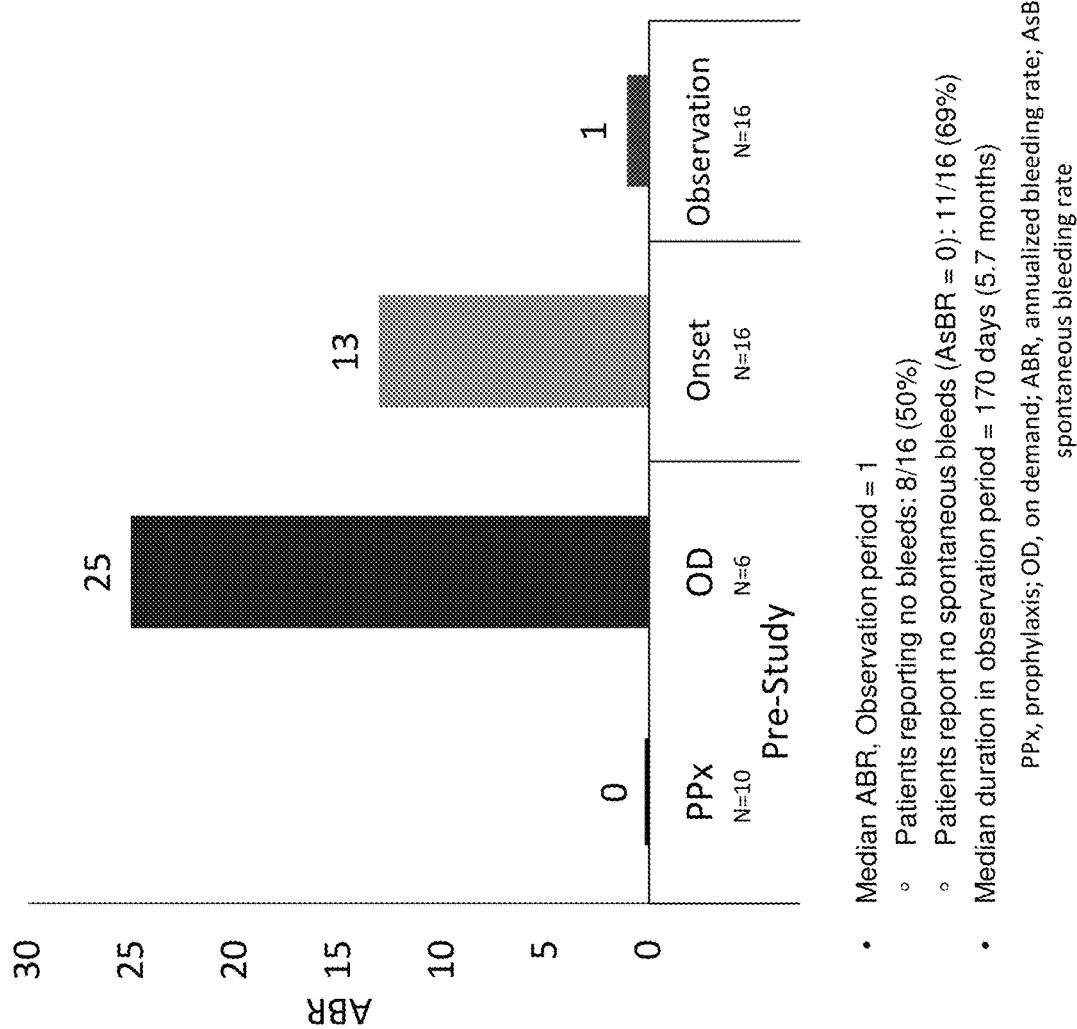
FIG. 20B is a graph showing the median annual bleed rate (ABR) prior to the initiation of the study, at the onset portion of the study, and during the observation portion of the study for all of the subjects in the Phase II OLE clinical trial of AD-57213.

An exploratory post-hoc analysis of the bleed events in the non-inhibitor patients in the Phase II OLE study was also performed. FIG. 20A shows that administration of AD-57213 to patients having Hemophilia A or B once monthly at a dose of either 50 mg or 80 mg results in a significant reduction in the pre-study ABR. Furthermore, as demonstrated in FIG. 20B, administration of AD-57213 to patients having Hemophilia A or B once monthly at a dose of either 50 mg or 80 mg reduces the median annual bleed rate (ABR) to 1 and reduces the median annualized spontaneous bleed rate (AsBR) to zero.

In addition, during the Phase II OLE, one patient (subject C1-3) underwent an elective surgical procedure. Specifically, a patient with severe hemophilia A receiving 50 mg monthly AD-57213 underwent an elective septoplasty. The procedure was successfully carried out with no associated adverse events. Further, as reported by the investigator via personal communication, the cumulative periprocedural utilization of recombinant factor VIII was approximately 5-fold less than typically used by the investigator for this type of surgery in a severe hemophilia A patient. Based on the International Society of Thrombosis and Haemostasis (ISTH) hemostasis efficacy score, the investigator rated hemostasis control in the intra-operative, 24 hours post-operative, and 7 days post-operative periods as all being "excellent."

In summary, AD-57213 was generally well tolerated in hemophilia A and B patients without inhibitors. There were no SAEs and no thromboembolic events related to AD-57213 administration. In addition, the data demonstrate that AD-57213 has clinical activity in that once-monthly subcutaneous dosing at 50 mg and 80 mg achieves dose-dependent AT lowering of ~80% and thrombin generation levels approaching the lower end of normal range. Furthermore, exploratory post-hoc analysis of bleeding events in patients having Hemophilia A or B without inhibitors demonstrates that administration of AD-57213 reduced the median ABR to 1 and the median annualized spontaneous bleed rate (AsBR) to zero. Eight of sixteen (50%) patients were bleed-free and eleven of sixteen (69%) patients experienced zero spontaneous bleeds. Moreover, during the first surgical case of a subject having severe Hemophilia A and administered AD-57213, a significant reduction in replacement factor was utilized to maintain hemostasis in the subject.

We claim:

1. A method of preventing at least one hemophilia symptom in a human subject having hemophilia A or hemophilia B, comprising subcutaneously administering to the human subject in need thereof a dose of 50-90 mg of a double stranded ribonucleic acid (dsRNA) molecule about once a month, wherein the dsRNA molecule comprises a sense strand and an antisense strand;

wherein the sense strand comprises the sequence 5'-GfsgsUfuAfaCfaCfCfAfuUfuAfcUfuCfaAf-3' (SEQ ID NO:13) and the antisense strand comprises the sequence 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf and Uf are 2'-fluoro A, C, G, and U, respectively; and s is a phosphorothioate linkage; and wherein a ligand is conjugated to the 3' end of the sense strand as shown in the following schematic:

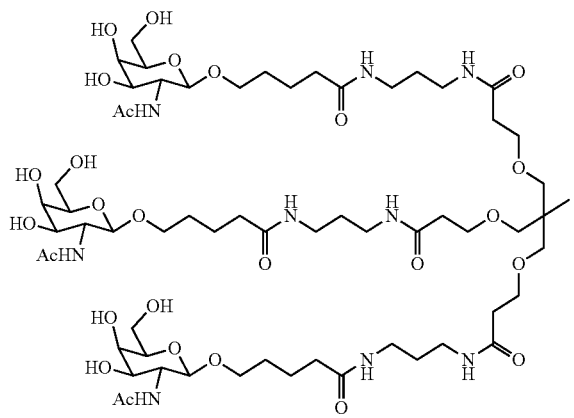

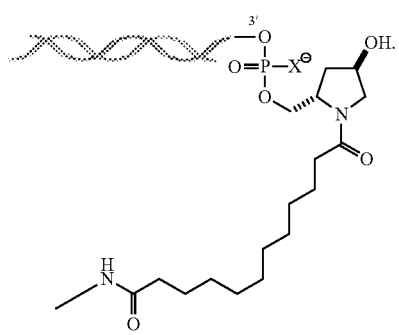

wherein X is O.

2. A method of treating a human subject having hemophilia A or hemophilia B, comprising subcutaneously administering to the human subject in need thereof a dose of 50-90 mg of a double stranded ribonucleic acid (dsRNA) molecule about once a month, wherein the dsRNA molecule comprises a sense strand and an antisense strand;

wherein the sense strand comprises the sequence 5'-GfsgsUfuAfaCfaCfCfAfuUfuAfcUfuCfaAf-3' (SEQ ID NO:13) and the antisense strand comprises the sequence 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein a ligand is conjugated to the 3' end of the sense strand as shown in the following schematic:

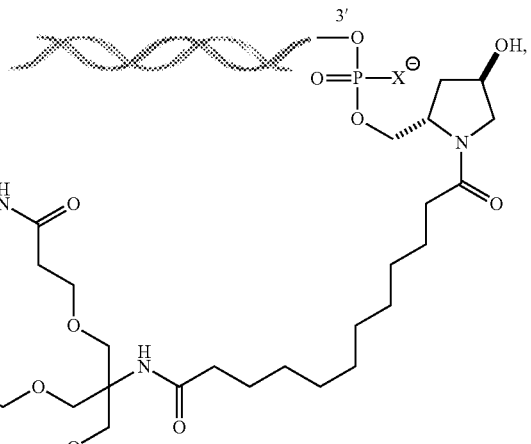

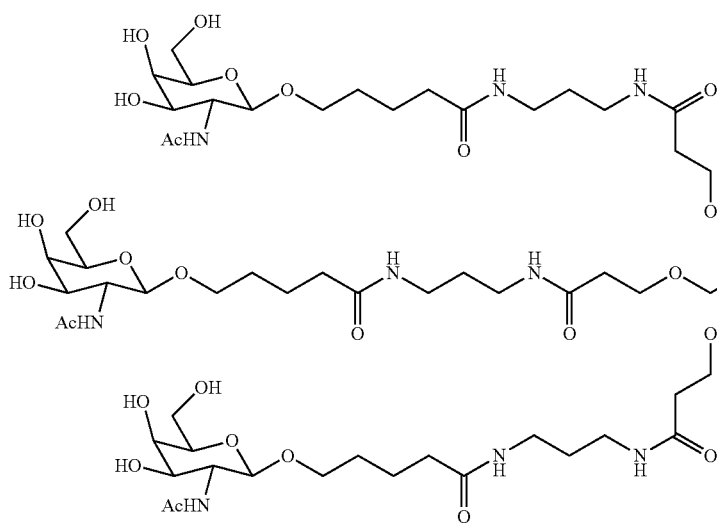

wherein X is O.

3. A method of preventing or reducing the frequency of bleeding episodes in a human subject having hemophilia A or hemophilia B, comprising subcutaneously administering to the human subject in need thereof a dose of 50-90 mg of a double stranded ribonucleic acid (dsRNA) molecule about once a month, wherein the dsRNA molecule comprises a sense strand and an antisense strand;

wherein the sense strand comprises the sequence 5'-GfsgsUfuAfaCfaCfCfAfuUfuAfcUfuCfaAf-3' (SEQ ID NO:13) and the antisense strand comprises the sequence 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein a ligand is conjugated to the 3' end of the sense strand as shown in the following schematic:

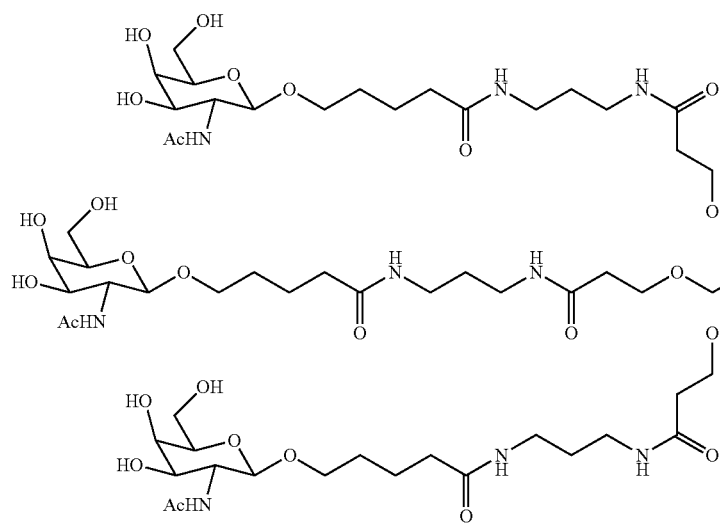

wherein X is O.

4. A method of reducing the annual bleeding rate (ABR) in a human subject having hemophilia A or hemophilia B, comprising subcutaneously administering to the human subject in need thereof a dose of 50-90 mg of a double stranded ribonucleic acid (dsRNA) molecule about once a month,
wherein the dsRNA molecule comprises a sense strand and an antisense strand;
wherein the sense strand comprises the sequence 5'-GfsgsUfuAfaCfaCfCfAfuUfuAfcUfuCfaAf-3' (SEQ ID NO:13) and the antisense strand comprises the sequence 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein a ligand is conjugated to the 3' end of the sense strand as shown in the following schematic:

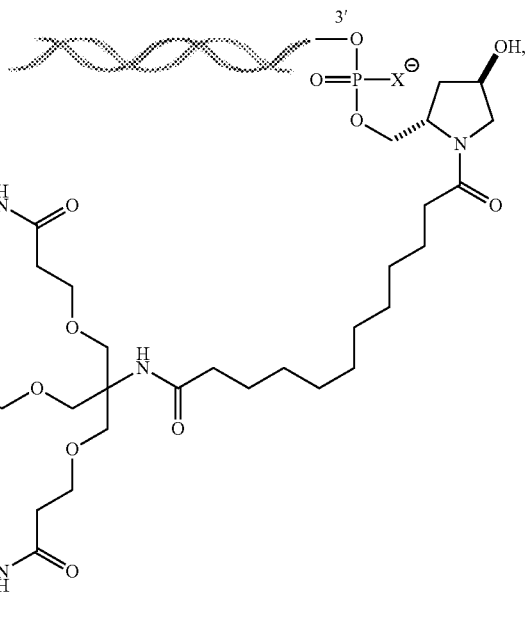

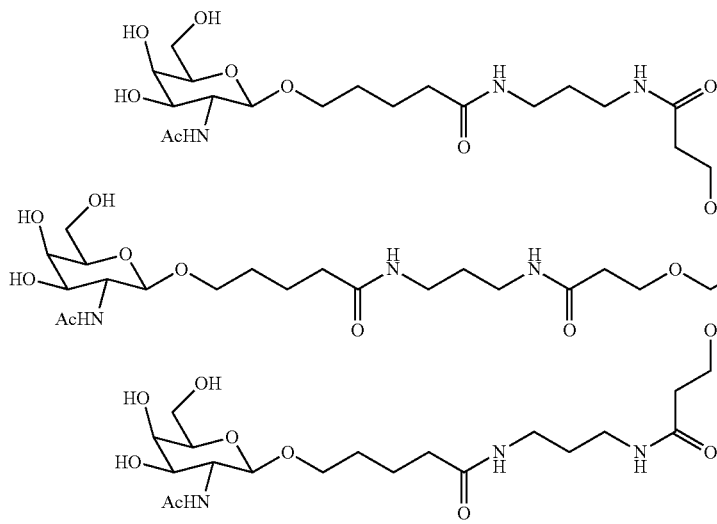

wherein X is O.

5. A method of reducing the annual spontaneous bleeding rate (AsBR) in a human subject having hemophilia A or hemophilia B, comprising subcutaneously administering to the human subject in need thereof a dose of 50-90 mg of a double stranded ribonucleic acid (dsRNA) molecule about once a month, wherein the dsRNA molecule comprises a sense strand and an antisense strand;

wherein the sense strand comprises the sequence 5'-GfsgsUfuAfaCfaCfCfAfuUfuAfcUfuCfaAf-3' (SEQ ID NO:13) and the antisense strand comprises the sequence 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein a ligand is conjugated to the 3' end of the sense strand as shown in the following schematic:

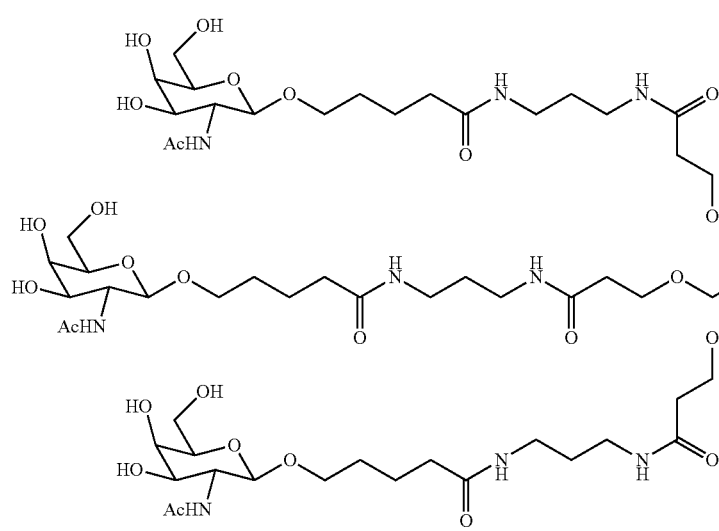
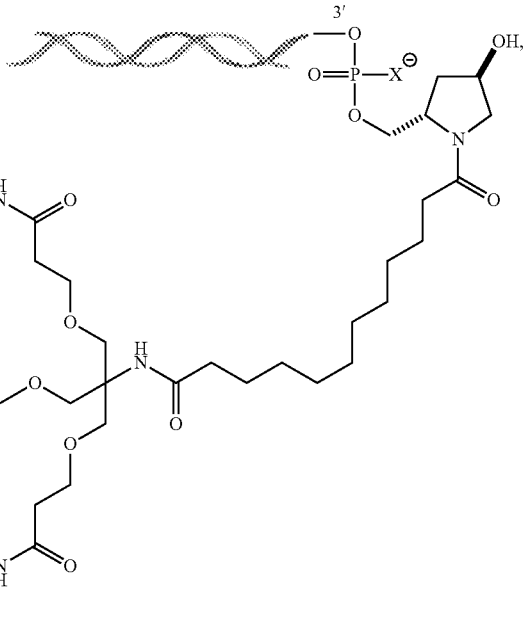

wherein X is O.

6. The method of claim 1, 2, 3, 4, or 5, wherein the dose of the dsRNA molecule is administered to the subject once a month.

7. The method of claim 1, 2, 3, 4, or 5, wherein the dsRNA molecule is administered to the subject at a dose of 80 mg.

8. The method of claim 1, 2, 3, 4, or 5, wherein the subject is a hemophilia A patient with inhibitors or a hemophilia B patient with inhibitors.

9. The method of claim 1, 2, 3, 4, or 5, wherein the subject is a hemophilia A patient without inhibitors or a hemophilia B patient without inhibitors.

10. The method of claim 1, 2, 3, 4, or 5, wherein administration of the dsRNA molecule to the subject lowers Serpinc1 activity in the subject by about 70% to about 95%.

11. The method of claim 1, 2, 3, 4, or 5, wherein administration of the dsRNA molecule to the subject increases peak thrombin levels in the subject to within the range of peak thrombin levels in a subject that does not have hemophilia A or hemophilia B.

12. The method of claim 1 or 2, wherein administration of the dsRNA molecule to the subject is sufficient to achieve peak thrombin generation levels in the subject to about the same level achieved by administration to the subject of Factor VIII.

13. The method of claim 1 or 2, wherein administration of the dsRNA molecule to the subject is sufficient to achieve peak thrombin generation levels of greater than about 40% in the subject.

14. The method of claim 1 or 2, wherein administration of the dsRNA molecule to the subject decreases the annual bleeding rate (ABR) of the subject by about 80 to about 95% as compared to the median historical on-demand ABR of subjects having the hemophilia and not administered the dsRNA molecule.

15. The method of claim 1 or 2, wherein the dsRNA molecule is administered to the subject in a buffered solution.

16. The method of claim 15, wherein the buffered solution is phosphate buffered saline.

17. The method of claim 1, 2, 3, 4, or 5, wherein the human subject is between about 19 and 61 years of age.

18. A method of preventing at least one hemophilia symptom in a human subject having hemophilia A or hemophilia B, comprising subcutaneously administering to the human subject in need thereof a dose of 80 mg of a double stranded ribonucleic acid (dsRNA) molecule about once a month, wherein the dsRNA molecule has a sense strand, an antisense strand, and a ligand;

wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein the ligand is conjugated to the 3' end of the sense strand as shown in the following schematic:

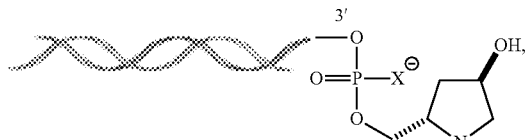
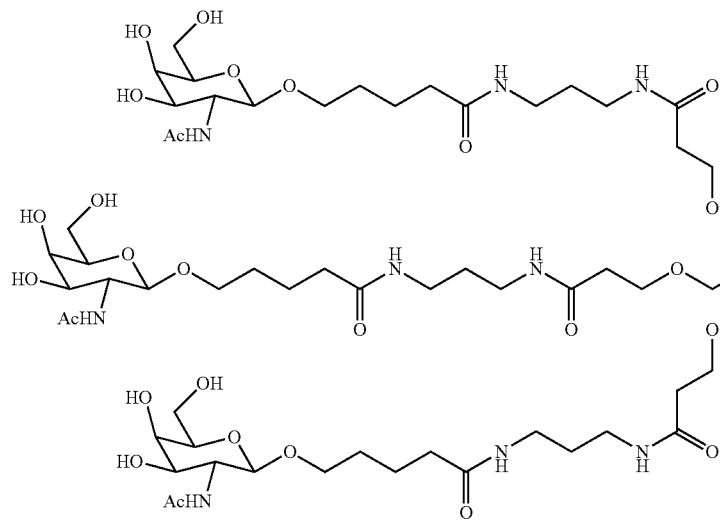

wherein X is O.

19. A method of treating a human subject having hemophilia A or hemophilia B, comprising subcutaneously administering to the human subject in need thereof a dose of 80 mg of a double stranded ribonucleic acid (dsRNA) molecule about once a month,
  wherein the dsRNA molecule has a sense strand, an antisense strand, and a ligand;
  wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
  wherein the ligand is conjugated to the 3' end of the sense strand as shown in the following schematic:

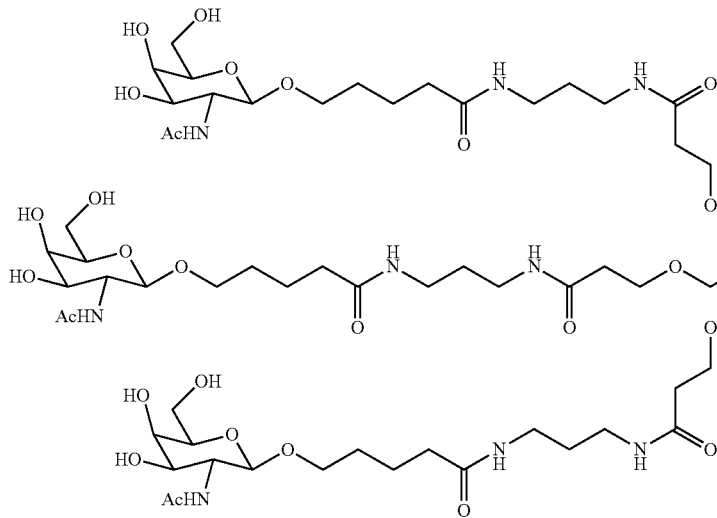

wherein X is O.

20. A method of preventing or reducing the frequency of bleeding episodes in a human subject having hemophilia A or hemophilia B, comprising subcutaneously administering to the human subject in need thereof a dose of 80 mg of a double stranded ribonucleic acid (dsRNA) molecule about once a month, wherein the dsRNA molecule has a sense strand, an antisense strand, and a ligand;

wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein the ligand is conjugated to the 3' end of the sense strand as shown in the following schematic:

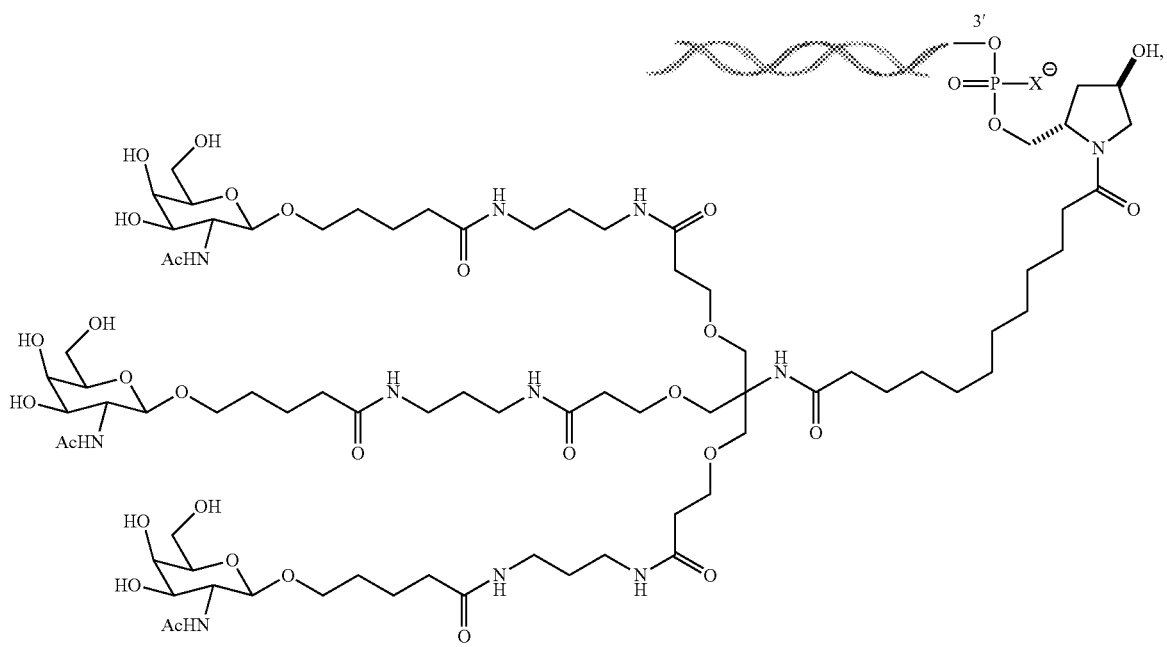

wherein X is O.

21. A method of reducing the annual bleeding rate (ABR) in a human subject having hemophilia A or hemophilia B, comprising subcutaneously administering to the human subject in need thereof a dose of 80 mg of a double stranded ribonucleic acid (dsRNA) molecule about once a month, wherein the dsRNA molecule has a sense strand, an antisense strand, and a ligand;

wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein the ligand is conjugated to the 3' end of the sense strand as shown in the following schematic:

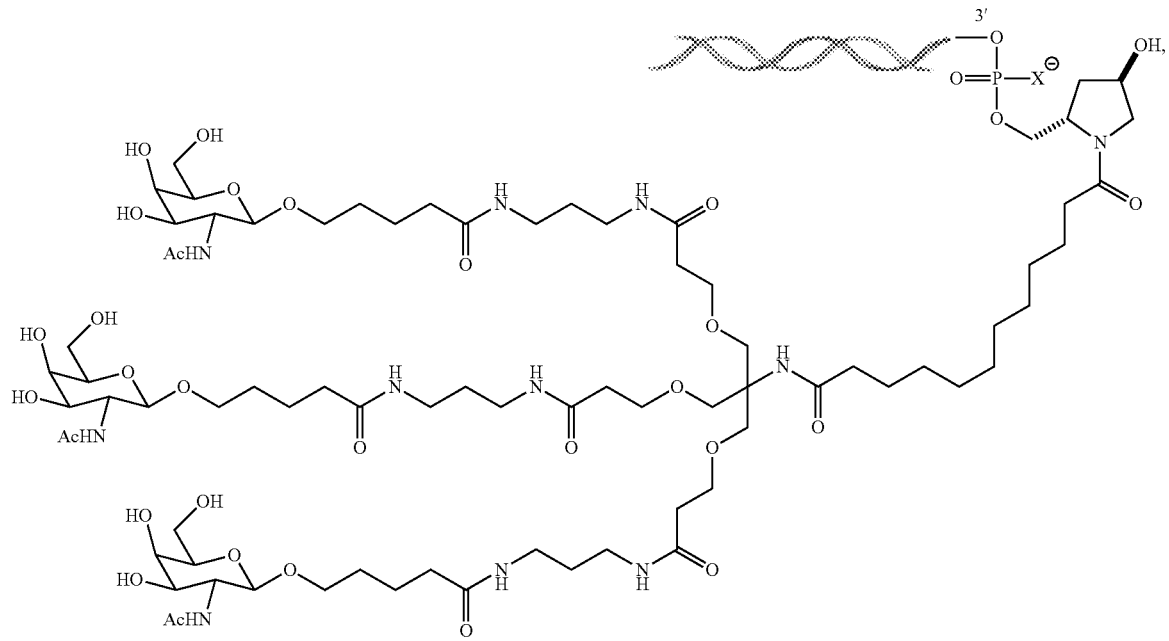

wherein X is O.

22. A method of reducing the annual spontaneous bleeding rate (AsBR) in a human subject having hemophilia A or hemophilia B, comprising subcutaneously administering to the human subject in need thereof a dose of 80 mg of a double stranded ribonucleic acid (dsRNA) molecule about once a month, wherein the dsRNA molecule has a sense strand, an antisense strand, and a ligand;

wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and wherein the ligand is conjugated to the 3' end of the sense strand as shown in the following schematic:

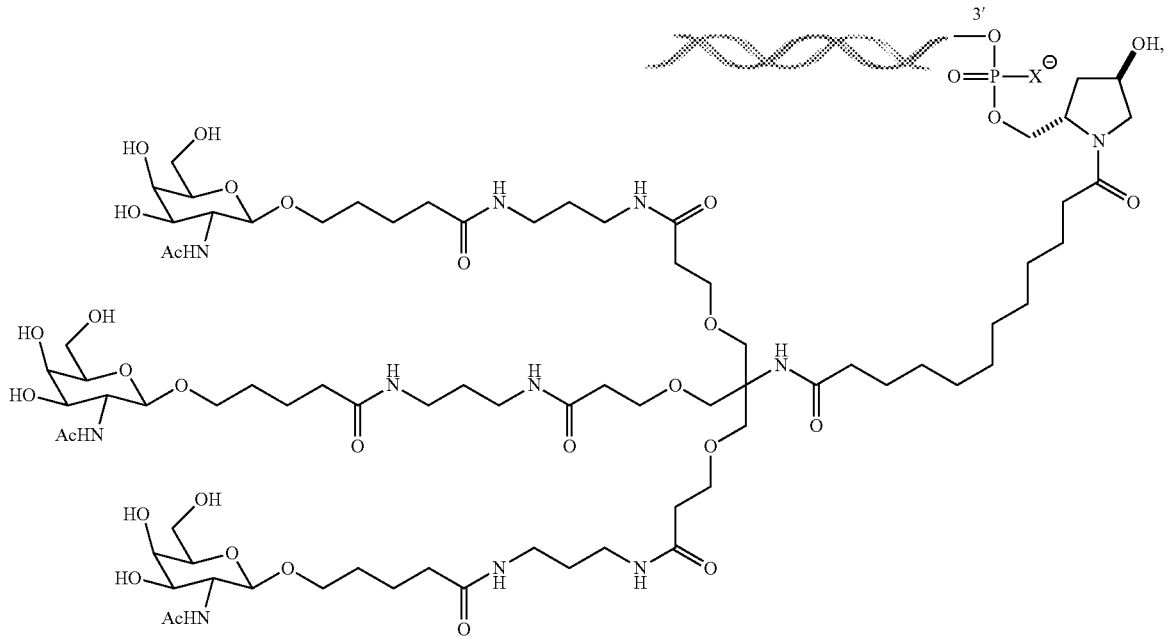

wherein X is O.

23. The method of claim 18, 19, 20, 21, or 22, wherein the dsRNA molecule is administered to the subject once a month.

24. The method of claim 23, wherein the subject is a hemophilia A patient with inhibitors or a hemophilia B patient with inhibitors.

25. The method of claim 23, wherein the subject is a hemophilia A patient without inhibitors or a hemophilia B patient without inhibitors.

26. The method of claim 4 or 21, wherein the administration reduces ABR of the subject to one or less.

27. The method of claim 5 or 22, wherein the administration reduces AsBR of the subject to zero.

28. The method of claim 1, 2, 3, 4, or 5, wherein the dsRNA molecule is administered to the subject at a dose of 50 mg.

29. A method of preventing at least one hemophilia symptom in a human subject having hemophilia A or hemophilia B, comprising subcutaneously administering to the human subject in need thereof a dose of 50 mg of a double stranded ribonucleic acid (dsRNA) molecule about once a month,
wherein the dsRNA molecule has a sense strand, an antisense strand, and a ligand;
wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
wherein the ligand is conjugated to the 3' end of the sense strand as shown in the following schematic:

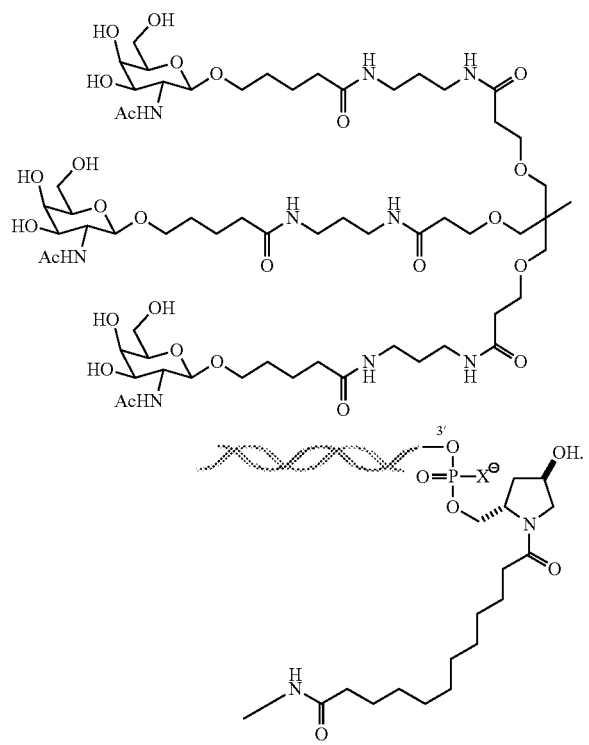

wherein X is O.

30. A method of treating a human subject having hemophilia A or hemophilia B, comprising subcutaneously administering to the human subject in need thereof a dose of 50 mg of a double stranded ribonucleic acid (dsRNA) molecule about once a month,
wherein the dsRNA molecule has a sense strand, an antisense strand, and a ligand;
wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
wherein the ligand is conjugated to the 3' end of the sense strand as shown in the following schematic:

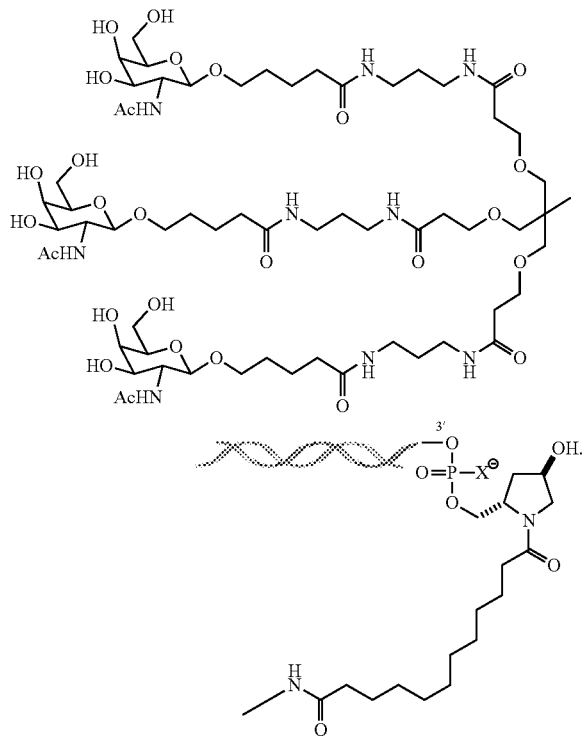

wherein X is O.

31. A method of preventing or reducing the frequency of bleeding episodes in a human subject having hemophilia A or hemophilia B, comprising subcutaneously administering to the human subject in need thereof a dose of 50 mg of a double stranded ribonucleic acid (dsRNA) molecule about once a month,
wherein the dsRNA molecule has a sense strand, an antisense strand, and a ligand;
wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuAfaCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
wherein the ligand is conjugated to the 3' end of the sense strand as shown in the following schematic:

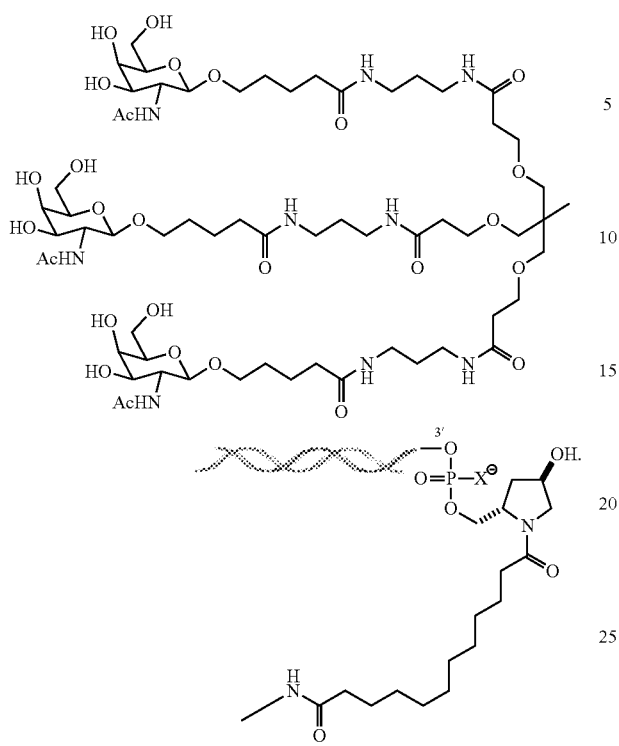

wherein X is O.

32. A method of reducing the annual bleeding rate (ABR) in a human subject having hemophilia A or hemophilia B, comprising subcutaneously administering to the human subject in need thereof a dose of 50 mg of a double stranded ribonucleic acid (dsRNA) molecule about once a month,
  wherein the dsRNA molecule has a sense strand, an antisense strand, and a ligand;
  wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
  wherein the ligand is conjugated to the 3' end of the sense strand as shown in the following schematic:

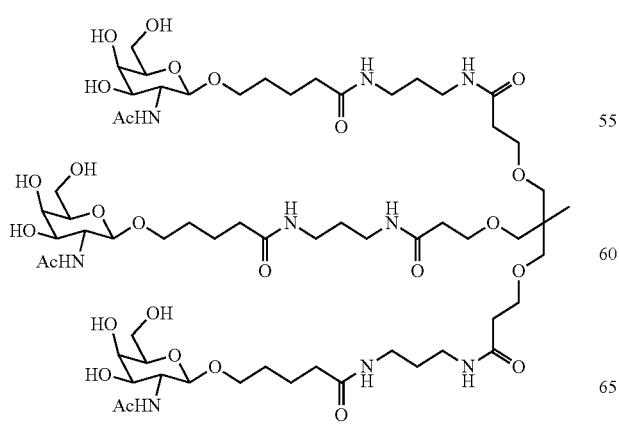

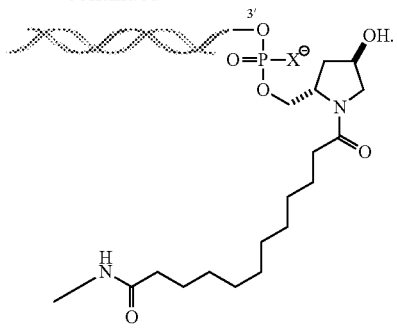

wherein X is O.

33. A method of reducing the annual spontaneous bleeding rate (AsBR) in a human subject having hemophilia A or hemophilia B, comprising subcutaneously administering to the human subject in need thereof a dose of 50 mg of a double stranded ribonucleic acid (dsRNA) molecule about once a month,
  wherein the dsRNA molecule has a sense strand, an antisense strand, and a ligand;
  wherein the sequence of the sense strand consists of 5'-GfsgsUfuAfaCfaCfCfAfuUfuAfcUfuCfaAf-3' (SEQ ID NO:13) and the sequence of the antisense strand consists of 5'-usUfsgAfaGfuAfaAfuggUfgUfuA-faCfcsasg-3' (SEQ ID NO:14), wherein a, c, g, and u are 2'-O-methyl (2'-OMe) A, C, G, and U, respectively; Af, Cf, Gf, and Uf are 2'-fluoro A, C, G, and U, respectively; and s is a phosphorothioate linkage; and
  wherein the ligand is conjugated to the 3' end of the sense strand as shown in the following schematic:

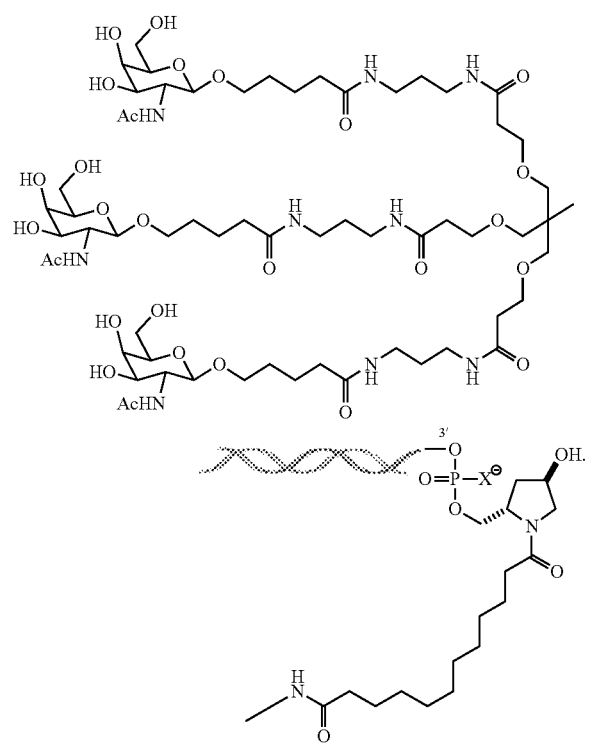

wherein X is O.

34. The method of claim 29, 30, 31, 32, or 33, wherein the dsRNA molecule is administered to the subject once a month.

35. The method of claim 34, wherein the subject is a hemophilia A patient with inhibitors or a hemophilia B patient with inhibitors.

36. The method of claim 34, wherein the subject is a hemophilia A patient without inhibitors or a hemophilia B patient without inhibitors.

37. The method of claim 32, wherein the administration reduces ABR of the subject to one or less.

38. The method of claim 33, wherein the administration reduces AsBR of the subject to zero.

* * * * *

SEQUENCE LISTING

```
<160> NUMBER OF SEQ ID NOS: 16

<210> SEQ ID NO 1
<211> LENGTH: 1599
<212> TYPE: DNA
<213> ORGANISM: Homo sapiens

<400> SEQUENCE: 1
tctgccccac cctgtcctct ggaacctctg cgagatttag aggaaagaac cagttttcag     60
gcggattgcc tcagatcaca ctatctccac ttgcccagcc ctgtggaaga ttagcggcca    120
tgtattccaa tgtgatagga actgtaacct ctggaaaaag gaaggtttat cttttgtcct    180
tgctgctcat tggcttctgg gactgcgtga cctgtcacgg gagccctgtg gacatctgca    240
cagccaagcc gcgggacatt cccatgaatc ccatgtgcat ttaccgctcc ccggagaaga    300
aggcaactga ggatgagggc tcagaacaga agatcccgga ggccaccaac cggcgtgtct    360
gggaactgtc caaggccaat tcccgctttg ctaccacttt ctatcagcac ctggcagatt    420
ccaagaatga caatgataac attttcctgt cacccctgag tatctccacg gcttttgcta    480
```

```
tgaccaagct gggtgcctgt aatgacaccc tccagcaact gatggaggta tttaagtttg    540
acaccatatc tgagaaaaca tctgatcaga tccacttctt ctttgccaaa ctgaactgcc    600
gactctatcg aaaagccaac aaatcctcca agttagtatc agccaatcgc cttttggag    660 acaaatccct taccttcaat gagacctacc aggacatcag tgagttggta tatggagcca    720
agctccagcc cctggacttc aaggaaaatg cagagcaatc cagagcggcc atcaacaaat    780
gggtgtccaa taagaccgaa ggccgaatca ccgatgtcat tccctcggaa gccatcaatg    840
agctcactgt tctggtgctg gttaacacca tttacttcaa gggcctgtgg aagtcaaagt    900
tcagccctga gaacacaagg aaggaactgt tctacaaggc tgatggagag tcgtgttcag    960
catctatgat gtaccaggaa ggcaagttcc gttatcggcg cgtggctgaa ggcacccagg   1020
tgcttgagtt gcccttcaaa ggtgatgaca tcaccatggt cctcatcttg cccaagcctg   1080
agaagagcct ggccaaggta gagaaggaac tcaccccaga ggtgctgcaa gagtggctgg   1140
atgaattgga ggagatgatg ctggtggtcc acatgccccg cttccgcatt gaggacggct   1200
tcagtttgaa ggagcagctg caagacatgg gccttgtcga tctgttcagc cctgaaaagt   1260
ccaaactccc aggtattgtt gcagaaggcc gagatgacct ctatgtctca gatgcattcc   1320
ataaggcatt tcttgaggta aatgaagaag gcagtgaagc agctgcaagt accgctgttg   1380
tgattgctgg ccgttcgcta aaccccaaca gggtgacttt caaggccaac aggcctttcc   1440
tggtttttat aagagaagtt cctctgaaca ctattatctt catgggcaga gtagccaacc   1500
cttgtgttaa gtaaaatgtt cttattcttt gcacctcttc ctattttggg tttgtgaaca   1560
gaagtaaaaa taaatacaaa ctacttccat ctcacatta                          1599

<210> SEQ ID NO 2
<211> LENGTH: 1545
<212> TYPE: DNA
<213> ORGANISM: Macaca mulatta

<400> SEQUENCE: 2
ggcacgagga ccatctccac ttgcccagcc ctgtggaaga ttagcgacca tgtattccaa     60
tgtgatagga accgtagcct ctggaaaaag gaaggtttat cttctgtcct tgctgctcat    120
tggcctctgg gactgtatga cctgtcacgg gagccctgtg gacatctgca cagccaagcc    180
gcgggacatt cccatgaatc ccatgtgcat ttaccgctcc ccggagaaga aggcaactga    240
ggatgagggc tcagaacaga gatccccga ggccaccaac cggcgcgtct gggaactgtc    300
caaggccaat tcccgctttg ctaccacttt ctatcagcac ctggcagatt ccaagaacga    360
caaggataac attttcctgt caccctgag tgtctccacg gcttttgcta tgaccaagct    420
gggtgcctgt aatgacaccc tcaagcaact gatggaggta tttaagtttg acaccatatc    480
tgagaaaaca tctgatcaga tccacttctt ctttgccaaa ctgaactgcc gactctatcg    540
aaaagccaac aaatcctcca agttagtatc agccaatcgc cttttggag acaaatccct    600 taccttcaat gagacctacc aggacatcag tgagttggta tacggagcca agctccagcc    660
cctggacttc aaggaaaatg cagagcaatc cagagcggcc atcaacaaat gggtgtccaa    720
taagaccgaa ggccgaatca ccgatgtcat tccccggaa gccatcaacg agctcactgt    780
tctggtgctg gttaacacca tttacttcaa gggcctgtgg aagtcaaagt ttagccctga    840
gaacacaagg atggaaccgt tctacaaggc tgatggagag tcgtgttcag cgtctatgat    900
gtaccaggaa ggcaagttct gttatcggcg cgtggctgaa ggcacccagg tgcttgagtt    960
```

| | |
|---|---|
| gcccttcaag ggtgatgaca tcaccatggt gctcatcctg cccaagcctg agaagagcct | 1020 |
| gaccaaggtg gagcaggaac tcaccccaga ggtgctgcag gagtggctgg atgagttgga | 1080 |
| ggagatgatg ctggtggttc acatgccccg cttccgcatt gaggacggct tcagtttgaa | 1140 |
| ggagcagctg caagacatgg gccttgtcga tctgttcagc cctgaaaagt ccaaactccc | 1200 |
| aggtattgtt gcagaaggcc gggatgacct ctatgtctcc gatgcattcc ataaggcatt | 1260 |
| tcttgaggta aatgaagaag gcagtgaagc agctgcaagt accgccattg ggattgctgg | 1320 |
| ccgttcgcta aaccccaaca gggtgacctt caaggccaac aggcctttcc tggtttttat | 1380 |
| aagagaagtt cctctgaaca ctattatctt catgggcaga gtagccaacc cttgtgtgag | 1440 |
| ctaaactgtt cttattcttt gtacctcttc ctattttggt ttgtgaatag aagtaaaaat | 1500 |
| aaatacaact actcccatct tacattaaaa aaaaaaaaaa aaaaa | 1545 |

<210> SEQ ID NO 3
<211> LENGTH: 2171
<212> TYPE: DNA
<213> ORGANISM: Mus musculus

<400> SEQUENCE: 3

| | |
|---|---|
| ataggtaatt ttagaaatag atctgatttg tatctgagac attttagtga agtggtgaga | 60 |
| tataagacat aatcagaaga catatctacc tgaagacttt aaggggagag ctccctcccc | 120 |
| cacctggcct ctggacctct cagatttagg ggaaagaacc agttttcgga gtgatcgtct | 180 |
| cagtcagcac catctctgta ggagcatcgg ccatgtattc ccctggggca ggaagtgggg | 240 |
| ctgctggtga gaggaagctt tgtctcctct ctctgctcct catcggtgcc ttgggctgtg | 300 |
| ctatctgtca cggaaaccct gtggacgaca tctgcatagc gaagccccga gacatccccg | 360 |
| tgaatccctt gtgcatttac cgctcccctg gaagaaggc caccgaggag gatggctcag | 420 |
| agcagaaggt tccagaagcc accaaccggc gggtctggga actgtccaag gccaattcgc | 480 |
| gatttgccac taacttctac cagcacctgg cagactccaa gaatgacaac gacaacattt | 540 |
| tcctgtcacc cttgagcatc tccactgctt ttgctatgac caagctgggt gcctgtaacg | 600 |
| acactctcaa gcagctgatg gaggttttta aatttgatac catctccgag aagacatccg | 660 |
| accagatcca cttcttcttt gccaaactga actgccgact ctatcgaaaa gccaacaagt | 720 |
| cctctgactt ggtatcagcc aaccgccttt ttggagacaa atccctcacc ttcaacgaga | 780 |
| gctatcaaga tgttagtgag gttgtctatg gagccaagct ccagcccctg gacttcaagg | 840 |
| agaatccgga gcaatccaga gtgaccatca caactgggt agctaataag actgaaggcc | 900 |
| gcatcaaaga tgtcatccca cagggcgcca ttaacgagct cactgccctg ttctggtta | 960 |
| acaccattta cttcaagggc ctgtggaagt caaagttcag ccctgagaac acaaggaagg | 1020 |
| aaccgttcta taaggtcgat gggcagtcat gcccagtgcc tatgatgtac caggaaggca | 1080 |
| aattcaaata ccggcgcgtg gcagagggca cccaggtgct agagctgccc ttcaaggggg | 1140 |
| atgacatcac catggtgctc atcctgccca gcctgagaa gagcctggcc aaggtggagc | 1200 |
| aggagctcac cccagagctg ctgcaggagt ggctggatga gctgtcagag actatgcttg | 1260 |
| tggtccacat gccccgcttc cgcaccgagg atggcttcag tctgaaggag cagctgcaag | 1320 |
| acatgggcct cattgatctc ttcagccctg aaaagtccca actcccaggg atcgttgctg | 1380 |
| gaggcaggga cgacctctat gtctccgacg cattccacaa agcatttctt gaggtaaatg | 1440 |
| aggaaggcag tgaagcagca gcgagtactt ctgtcgtgat tactgccggg tcactgaacc | 1500 |
| ccaataggggt gaccttcaag gccaacaggc ccttcctggt tcttataagg gaagttgcac | 1560 |

```
tgaacactat tatattcatg gggagagtgg ctaatccttg tgtgaactaa aatattctta    1620
atctttgcac cttttcctac tttggtgttt gtgaatagaa gtaaaaataa atacgactgc    1680
cacctcacga gaatggactt ttccacttga agacgagaga ctggagtaca gatgctacac    1740
cacttttggg caagtgaagg gggagcagcc agccacggtg gcacaaacct atatcctggt    1800
gcttttgaag gtagaagcag ggcggtcagg agttaaggcc agttgaggct gggctgcaga    1860
gtgaaagacc atgtctcaag atggtctttc tcctcccaa agtagaaaag aaaaccataa     1920
aaacaagagg taaatatatt actatttcat cttagaggat agcaggcatc ttgaaagggt    1980
agagggacct taaattctca ttattgcccc catactacaa actaaaaaac aaacccgaat    2040
caatctccca taaagacaga gattcaaata agagtattaa acgttttatt tctcaaacca    2100
ctcacatgca taatgttctt atacacagtg tcaaaataaa gagaaatgca tttttataca    2160
aaaaaaaaaa a                                                         2171

<210> SEQ ID NO 4
<211> LENGTH: 1561
<212> TYPE: DNA
<213> ORGANISM: Rattus norvegicus

<400> SEQUENCE: 4
cggagggatt gctcagcact gtctccacgg cttctctgca gaagcgtcca ccatgtattc      60
cccgggaata ggaagtgcgg ttgctggaga gaggaagctt tgtctcctct ctctgctact     120
cattggtgcc ttgggctgtg ctgtctgtca tggaaaccct gtggacgaca tctgcatagc     180
gaagccccga gacatccccg tgaaccccat gtgcatttac cgctcccctg cgaagaaggc     240
cacggaggag gatgtcctag agcagaaggt tccggaagcc accaaccggc gggtctggga     300
actgtccaag gccaattctc gatttgccac taacttctat cagcacctgg cagactccaa     360
gaacgacaac gacaacattt tcctgtcacc cttgagcatc tccacggcgt ttgctatgac     420
caagctgggt gcttgtaata caccctcaa gcagctgatg gaggttttta aatttgatac      480
catctccgag aagacatccg accagatcca cttcttcttt gccaaactga actgccgact     540
ctatcgaaaa gccaacaagt cctctaactt ggtgtcagcc aaccgccttt ttggagacaa     600
atcccttacc ttcaatgaga gctatcaaga cgttagtgag attgtctatg gagccaagct     660
tcagcccctg gacttcaagg agaatccgga gcaatccaga gtgaccatca caactgggt    720 agctaataag actgaaggcc gcatcaaaga cgtcatcccc caaggagcca ttgatgagct     780
cactgccctg gtgctggtta acaccattta cttcaagggc ctgtggaagt caaagttcag     840
ccctgagaac acaaggaagg aaccattcca caagttgat gggcagtcat gcctggtgcc    900
catgatgtac caggaaggca aattcaaata caggcgtgtg ggagagggta cccaggtgct     960
agagatgccc ttcaaggggg acgacatcac catggtgctc atcctgccca gcctgagaa    1020 gagcctggct aaggtggagc aggaactcac cccggagctg ctgcaggagt ggctggatga    1080
gctgtcggag gtcatgcttg tggtccacgt gccccgcttc cgcatcgagg acagcttcag    1140
tctgaaggag cagctgcaag acatgggcct tgttgatctc ttcagccctg agaagtccca    1200
actcccaggg atcattgctg aaggcaggga cgacctcttt gtctccgatg cattccacaa    1260
agcgtttctt gaggtaaatg aggaaggcag tgaagcagca gcgagtactt ctgtcgtgat    1320
tactggccgg tcactgaacc ccagtagggt gaccttcaag gccaacaggc ccttcctggt    1380
tcttataagg gaagtcgcac tgaacactat tatattcatg gggagagtgt ctaatccttg    1440
```

| | |
|---|---|
| tgtgaactaa aatattctta atctttgcac cttttcctat ctcggtgttt gttaatggaa | 1500 |
| gtaaaaataa atatgactgc cacctcaaaa aaaaaaaaaa aaaaaaaaaa aaaaaaaaaa | 1560 |
| a | 1561 |

<210> SEQ ID NO 5
<211> LENGTH: 1599
<212> TYPE: DNA
<213> ORGANISM: Homo sapiens

<400> SEQUENCE: 5

| | |
|---|---|
| taatgtgaga tggaagtagt ttgtatttat ttttacttct gttcacaaac caaaaatagg | 60 |
| aagaggtgca aagaataaga acattttact taacacaagg gttggctact ctgcccatga | 120 |
| agataatagt gttcagagga acttctctta taaaaaccag gaaaggcctg ttggccttga | 180 |
| aagtcaccct gttggggttt agcgaacggc cagcaatcac aacagcggta cttgcagctg | 240 |
| cttcactgcc ttcttcattt acctcaagaa atgccttatg gaatgcatct gagacataga | 300 |
| ggtcatctcg gccttctgca acaatacctg ggagtttgga cttttcaggg ctgaacagat | 360 |
| cgacaaggcc catgtcttgc agctgctcct tcaaactgaa gccgtcctca atgcggaagc | 420 |
| ggggcatgtg gaccaccagc atcatctcct ccaattcatc cagccactct gcagcacct | 480 |
| ctggggtgag ttccttctct accttggcca ggctcttctc aggcttgggc aagatgagga | 540 |
| ccatggtgat gtcatcacct tgaagggca actcaagcac ctgggtgcct cagccacgc | 600 |
| gccgataacg gaacttgcct tcctggtaca tcatagatgc tgaacacgac tctccatcag | 660 |
| ccttgtagaa cagttccttc cttgtgttct cagggctgaa ctttgacttc cacaggccct | 720 |
| tgaagtaaat ggtgttaacc agcaccagaa cagtgagctc attgatggct tccgagggaa | 780 |
| tgacatcggt gattcggcct tcggtcttat tggacaccca tttgttgatg ccgctctgg | 840 |
| attgctctgc attttccttg aagtccaggg gctggagctt ggctccatat accaactcac | 900 |
| tgatgtcctg gtaggtctca ttgaaggtaa gggatttgtc tccaaaaagg cgattggctg | 960 |
| atactaactt ggaggatttg ttggcttttc gatagagtcg gcagttcagt ttggcaaaga | 1020 |
| agaagtggat ctgatcagat gttttctcag atatggtgtc aaacttaaat acctccatca | 1080 |
| gttgctggag ggtgtcatta caggcaccca gcttggtcat agcaaaagcc gtggagatac | 1140 |
| tcagggtga caggaaaatg ttatcattgt cattcttgga atctgccagg tgctgataga | 1200 |
| aagtggtagc aaagcgggaa ttggccttgg acagttccca gacacgccgg ttggtggcct | 1260 |
| ccgggatctt ctgttctgag ccctcatcct cagttgcctt cttctccggg gagcggtaaa | 1320 |
| tgcacatggg attcatggga atgtcccgcg gcttggctgt gcagatgtcc acagggctcc | 1380 |
| cgtgacaggt cacgcagtcc cagaagccaa tgagcagcaa ggacaaaaga taaaccttcc | 1440 |
| tttttccaga ggttacagtt cctatcacat tggaatacat ggccgctaat cttccacagg | 1500 |
| gctgggcaag tggagatagt gtgatctgag gcaatccgcc tgaaaactgg ttctttcctc | 1560 |
| taaatctcgc agaggttcca gaggacaggg tggggcaga | 1599 |

<210> SEQ ID NO 6
<211> LENGTH: 1545
<212> TYPE: DNA
<213> ORGANISM: Macaca mulatta

<400> SEQUENCE: 6

| | |
|---|---|
| tttttttttt tttttttta atgtaagatg ggagtagttg tatttatttt tacttctatt | 60 |
| cacaaaccaa aataggaaga ggtacaaaga ataagaacag tttagctcac acaagggttg | 120 |

```
gctactctgc ccatgaagat aatagtgttc agaggaactt ctcttataaa aaccaggaaa      180
ggcctgttgg ccttgaaggt caccctgttg gggtttagcg aacggccagc aatcccaatg      240
gcggtacttg cagctgcttc actgccttct tcatttacct caagaaatgc cttatggaat      300
gcatcggaga catagaggtc atcccggcct tctgcaacaa tacctgggag tttggacttt      360
tcagggctga acagatcgac aaggcccatg tcttgcagct gctccttcaa actgaagccg      420
tcctcaatgc ggaagcgggg catgtgaacc accagcatca tctcctccaa ctcatccagc      480
cactcctgca gcacctctgg ggtgagttcc tgctccacct tggtcaggct cttctcaggc      540
ttgggcagga tgagcaccat ggtgatgtca tcacccttga agggcaactc aagcacctgg      600
gtgccttcag ccacgcgccg ataacagaac ttgccttcct ggtacatcat agacgctgaa      660
cacgactctc catcagcctt gtagaacggt tccatccttg tgttctcagg gctaaacttt      720
gacttccaca ggcccttgaa gtaaatggtg ttaaccagca ccagaacagt gagctcgttg      780
atggcttccg ggggaatgac atcggtgatt cggccttcgg tcttattgga cacccatttg      840
ttgatggccg ctctggattg ctctgcattt tccttgaagt ccaggggctg gagcttggct      900
ccgtatacca actcactgat gtcctggtag gtctcattga aggtaaggga tttgtctcca      960
aaaaggcgat tggctgatac taacttggag gatttgttgg cttttcgata gagtcggcag     1020
ttcagtttgg caaagaagaa gtggatctga tcagatgttt tctcagatat ggtgtcaaac     1080
ttaaatacct ccatcagttg cttgagggtg tcattacagg cacccagctt ggtcatagca     1140
aaagccgtgg agacactcag gggtgacagg aaaatgttat ccttgtcgtt cttggaatct     1200
gccaggtgct gatagaaagt ggtagcaaag cgggaattgg ccttggacag ttcccagacg     1260
cgccggttgg tggcctcggg gatcttctgt tctgagccct catcctcagt tgccttcttc     1320
tccggggagc ggtaaatgca catgggattc atgggaatgt cccgcggctt ggctgtgcag     1380
atgtccacag ggctcccgtg acaggtcata cagtcccaga ggccaatgag cagcaaggac     1440
agaagataaa ccttccttt tccagaggct acggttccta tcacattgga atacatggtc     1500
gctaatcttc cacagggctg ggcaagtgga gatggtcctc gtgcc                     1545
```

<210> SEQ ID NO 7
<211> LENGTH: 2171
<212> TYPE: DNA
<213> ORGANISM: Mus musculus

<400> SEQUENCE: 7

```
tttttttttt ttgtataaaa atgcatttct ctttatttg acactgtgta taagaacatt       60
atgcatgtga gtggtttgag aaataaaacg tttaatactc ttatttgaat ctctgtcttt      120
atgggagatt gattcgggtt tgttttttag tttgtagtat gggggcaata atgagaattt      180
aaggtccctc tacccttca agatgcctgc tatcctctaa gatgaaatag taatatattt       240
acctcttgtt tttatggttt tcttttctac tttggggagg agaaagacca tcttgagaca      300
tggtctttca ctctgcagcc cagcctcaac tggccttaac tcctgaccgc cctgcttcta      360
ccttcaaaag caccaggata taggtttgtg ccaccgtggc tggctgctcc cccttcactt      420
gcccaaaagt ggtgtagcat ctgtactcca gtctctcgtc ttcaagtgga aaagtccatt      480
ctcgtgaggt ggcagtcgta tttattttta cttctattca caaacaccaa agtaggaaaa      540
ggtgcaaaga ttaagaatat tttagttcac acaaggatta gccactctcc ccatgaatat      600
aatagtgttc agtgcaactt cccttataag aaccaggaag ggcctgttgg ccttgaaggt      660
```

| | |
|---|---|
| caccctattg gggttcagtg accggccagt aatcacgaca gaagtactcg ctgctgcttc | 720 |
| actgccttcc tcatttacct caagaaatgc tttgtggaat gcgtcggaga catagaggtc | 780 |
| gtccctgcct ccagcaacga tccctgggag ttgggacttt tcagggctga agagatcaat | 840 |
| gaggcccatg tcttgcagct gctccttcag actgaagcca tcctcggtgc ggaagcgggg | 900 |
| catgtggacc acaagcatag tctctgacag ctcatccagc cactcctgca gcagctctgg | 960 |
| ggtgagctcc tgctccacct tggccaggct cttctcaggc ttgggcagga tgagcaccat | 1020 |
| ggtgatgtca tcccccttga agggcagctc tagcacctgg gtgccctctg ccacgcgccg | 1080 |
| gtatttgaat ttgccttcct ggtacatcat aggcactggg catgactgcc catcgacctt | 1140 |
| atagaacggt tccttccttg tgttctcagg gctgaacttt gacttccaca ggcccttgaa | 1200 |
| gtaaatggtg ttaaccagaa ccagggcagt gagctcgtta atggcgccct gtgggatgac | 1260 |
| atctttgatg cggccttcag tcttattagc tacccagttg ttgatggtca ctctggattg | 1320 |
| ctccggattc tccttgaagt ccaggggctg gagcttggct ccatagacaa cctcactaac | 1380 |
| atcttgatag ctctcgttga aggtgaggga tttgtctcca aaaaggcggt tggctgatac | 1440 |
| caagtcagag gacttgttgg cttttcgata gagtcggcag ttcagtttgg caaagaagaa | 1500 |
| gtggatctgg tcggatgtct tctcggagat ggtatcaaat ttaaaaacct ccatcagctg | 1560 |
| cttgagagtg tcgttacagg cacccagctt ggtcatagca aaagcagtgg agatgctcaa | 1620 |
| gggtgacagg aaaatgttgt cgttgtcatt cttggagtct gccaggtgct ggtagaagtt | 1680 |
| agtggcaaat cgcgaattgg ccttggacag ttcccagacc cgccggttgg tggcttctgg | 1740 |
| aaccttctgc tctgagccat cctcctcggt ggccttcttc ccaggggagc ggtaaatgca | 1800 |
| caagggattc acggggatgt ctcggggctt cgctatgcag atgtcgtcca cagggtttcc | 1860 |
| gtgacagata gcacagccca aggcaccgat gaggagcaga gagaggagac aaagcttcct | 1920 |
| ctcaccagca gccccacttc ctgccccagg ggaatacatg gccgatgctc ctacagagat | 1980 |
| ggtgctgact gagacgatca ctccgaaaac tggttctttc ccctaaatct gagaggtcca | 2040 |
| gaggccaggt gggggaggga gctctcccct taaagtcttc aggtagatat gtcttctgat | 2100 |
| tatgtcttat atctcaccac ttcactaaaa tgtctcagat acaaatcaga tctatttcta | 2160 |
| aaattaccta t | 2171 |

<210> SEQ ID NO 8
<211> LENGTH: 1561
<212> TYPE: DNA
<213> ORGANISM: Rattus norvegicus

<400> SEQUENCE: 8

| | |
|---|---|
| tttttttttt tttttttttt tttttttttt ttttttgaggt ggcagtcata tttattttta | 60 |
| cttccattaa caaacaccga gataggaaaa ggtgcaaaga ttaagaatat tttagttcac | 120 |
| acaaggatta gacactctcc ccatgaatat aatagtgttc agtgcgactt cccttataag | 180 |
| aaccaggaag ggcctgttgg ccttgaaggt caccctactg gggttcagtg accggccagt | 240 |
| aatcacgaca gaagtactcg ctgctgcttc actgccttcc tcatttacct caagaaacgc | 300 |
| tttgtggaat gcatcggaga caaagaggtc gtccctgcct tcagcaatga tccctgggag | 360 |
| ttgggacttc tcagggctga agagatcaac aaggcccatg tcttgcagct gctccttcag | 420 |
| actgaagctg tcctcgatgc ggaagcgggg cacgtggacc acaagcatga cctccgacag | 480 |
| ctcatccagc cactcctgca gcagctccgg ggtgagttcc tgctccacct tagccaggct | 540 |
| cttctcaggc ttgggcagga tgagcaccat ggtgatgtcg tcccccttga agggcatctc | 600 |

-continued

```
tagcacctgg gtaccctctc ccacacgcct gtatttgaat ttgccttcct ggtacatcat    660
gggcaccagg catgactgcc catcaacttt gtggaatggt tccttccttg tgttctcagg    720
gctgaacttt gacttccaca ggcccttgaa gtaaatggtg ttaaccagca ccagggcagt    780
gagctcatca atggctcctt gggggatgac gtctttgatg cggccttcag tcttattagc    840
tacccagttg ttgatggtca ctctggattg ctccggattc tccttgaagt ccaggggctg    900
aagcttggct ccatagacaa tctcactaac gtcttgatag ctctcattga aggtaaggga    960
tttgtctcca aaaaggcggt tggctgacac caagttagag gacttgttgg cttttcgata   1020
gagtcggcag ttcagtttgg caaagaagaa gtggatctgg tcggatgtct tctcggagat   1080
ggtatcaaat ttaaaaacct ccatcagctg cttgagggtg ttattacaag cacccagctt   1140
ggtcatagca aacgccgtgg agatgctcaa gggtgacagg aaaatgttgt cgttgtcgtt   1200
cttggagtct gccaggtgct gatagaagtt agtggcaaat cgagaattgg ccttggacag   1260
ttcccagacc cgccggttgg tggcttccgg aaccttctgc tctaggacat cctcctccgt   1320
ggccttcttc gcagggagc ggtaaatgca catgggttc acggggatgt ctcggggctt      1380
cgctatgcag atgtcgtcca cagggtttcc atgacagaca gcacagccca aggcaccaat   1440
gagtagcaga gagaggagac aaagcttcct ctctccagca accgcacttc ctattcccgg   1500
ggaatacatg gtggacgctt ctgcagagaa gccgtggaga cagtgctgag caatccctcc   1560
g                                                                    1561
```

```
<210> SEQ ID NO 9
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      RFGF peptide"

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 10

Ala Ala Leu Leu Pro Val Leu Leu Ala Ala Pro
1               5                   10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Arg Pro Pro Gln
1               5                   10
```

```
<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gguuaacacc auuuacuuca a                                            21

<210> SEQ ID NO 14
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
uugaaguaaa ugguguuaac cag                                          23

<210> SEQ ID NO 15
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
uugaaguaaa ugguguuaac cag                                          23

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gguuaacacc auuuacuuca a                                            21
```